US010610861B2

(12) United States Patent
Meissonnier et al.

(10) Patent No.: US 10,610,861 B2
(45) Date of Patent: Apr. 7, 2020

(54) SYSTEMS, COMPOSITIONS AND METHODS FOR DETECTING A BIOLOGICAL CONDITION

(71) Applicant: ACCELLIX LTD., Jerusalem (IL)

(72) Inventors: Julien Meissonnier, Jerusalem (IL); Harvey Lee Kasdan, Jerusalem (IL); Yoav Zuta, Jerusalem (IL); Bruce Davis, Clifton, ME (US); Micha Rosen, Jerusalem (IL); Yael Himmel, Jerusalem (IL); Yehoshua Broder, Jerusalem (IL); Boaz Giron, Jerusalem (IL); Zion Botesazan, Jerusalem (IL); Eliezer Blasberg, Jerusalem (IL); Ilan Semmel, Jerusalem (IL); Jacques Aschkenasy, Jerusalem (IL); Bruce Goldman, Jerusalem (IL)

(73) Assignee: ACCELLIX LTD., Jerusalem (IL)

( * ) Notice: Subject to any disclaimer, the term of this patent is extended or adjusted under 35 U.S.C. 154(b) by 353 days.

(21) Appl. No.: 14/108,437

(22) Filed: Dec. 17, 2013

(65) Prior Publication Data
US 2014/0170680 A1 Jun. 19, 2014
Related U.S. Application Data

(63) Continuation-in-part of application No. 13/716,246, filed on Dec. 17, 2012, now abandoned.
(Continued)

(51) Int. Cl.
B01L 3/00 (2006.01)
G01N 33/569 (2006.01)

(52) U.S. Cl.
CPC ........ B01L 3/502 (2013.01); G01N 33/56972 (2013.01); B01L 2200/10 (2013.01);
(Continued)

(58) Field of Classification Search
CPC .......... G01N 33/56972; G01N 2800/26; B01L 3/502; B01L 2300/0867; B01L 2300/0816; B01L 2200/10; B01L 2400/0481
See application file for complete search history.

(56) References Cited

U.S. PATENT DOCUMENTS 3,241,432 A   3/1966   Skeggs et al.
4,233,029 A   11/1980  Columbus
(Continued)

FOREIGN PATENT DOCUMENTS

CN    1717280 A    1/2006
CN    101082621 A  12/2007
(Continued)

OTHER PUBLICATIONS

Adams, L. R., & Kamentsky, L. A. (1971). Machine characterization of human leukocytes by acridine orange fluorescence. Acta cytologica, 15(3), 289.
(Continued)

Primary Examiner — Melanie Brown
(74) Attorney, Agent, or Firm — Mark S. Cohen; Pearl Cohen Zedek Latzer Baratz LLP

(57) ABSTRACT

Determining a biological condition in a mammal by using a cartridge, having fluidic open channels, sealable after receiving a fluid specimen, passing any of the specimen through any of the channels, contacting any reagent stored in a chamber with the specimen in a reaction chamber inducing a reaction and forming a reaction product, a mechanical controller including first urging means applying a force externally onto the chamber to release the reagent, second urging means applying a removable force onto the channels thereby inducing fluidic movement in a first direction in the channels and upon removal of the force causing fluidic movement in an opposite direction, alignment means aligning a reading channel on the cartridge for a detection to take place, an optical reader detecting the reaction product in the reading channel, and a processor receiving data from the optical reader and processing the data to determine the biological condition.

30 Claims, 26 Drawing Sheets

Related U.S. Application Data

(60) Provisional application No. 61/737,854, filed on Dec. 17, 2012, provisional application No. 61/737,856, filed on Dec. 17, 2012.

(52) U.S. Cl.
CPC ............... *B01L 2300/0816* (2013.01); *B01L 2300/0867* (2013.01); *B01L 2400/0481* (2013.01); *G01N 2800/26* (2013.01)

(56) References Cited

U.S. PATENT DOCUMENTS

| | | | |
|---|---|---|---|
| 4,376,820 A | 3/1983 | Giannini et al. | |
| 4,400,370 A | 8/1983 | Kass | |
| 4,444,879 A | 4/1984 | Foster et al. | |
| 4,554,257 A | 11/1985 | Aladjem et al. | |
| 4,660,971 A | 4/1987 | Sage et al. | |
| 4,684,252 A | 8/1987 | Makiguchi et al. | |
| 4,730,899 A | 3/1988 | Kime et al. | |
| 4,745,285 A | 5/1988 | Recktenwald et al. | |
| 4,882,284 A | 11/1989 | Kirchanski et al. | |
| 5,126,276 A | 6/1992 | Fish et al. | |
| 5,304,487 A | 4/1994 | Wilding et al. | |
| 5,311,426 A | 5/1994 | Donohue et al. | |
| 5,408,314 A | 4/1995 | Perry et al. | |
| 5,627,040 A | 5/1997 | Bierre et al. | |
| 5,627,041 A | 5/1997 | Shartle et al. | |
| 5,631,734 A | 5/1997 | Stern | |
| 5,716,852 A | 2/1998 | Yager et al. | |
| 5,726,404 A * | 3/1998 | Brody | B01L 3/502738 137/261 |
| 5,747,349 A | 5/1998 | van den Engh et al. | |
| 5,837,115 A | 11/1998 | Austin et al. | |
| 5,932,100 A | 8/1999 | Yager et al. | |
| 5,972,710 A | 10/1999 | Weigl et al. | |
| 5,981,956 A | 11/1999 | Stern | |
| 6,136,610 A | 10/2000 | Polito et al. | |
| 6,168,948 B1 * | 1/2001 | Anderson | B01F 11/0266 366/DIG. 3 |
| 6,274,323 B1 | 8/2001 | Bruchez et al. | |
| 6,280,148 B1 | 8/2001 | Zengerle et al. | |
| 6,372,516 B1 | 4/2002 | Sun | |
| 6,382,228 B1 | 5/2002 | Cabuz et al. | |
| 6,399,952 B1 | 6/2002 | Maher et al. | |
| 6,426,230 B1 | 7/2002 | Feistel | |
| 6,540,895 B1 | 4/2003 | Spence et al. | |
| 6,541,213 B1 | 4/2003 | Weigl et al. | |
| 6,551,841 B1 | 4/2003 | Wilding et al. | |
| 6,635,163 B1 | 10/2003 | Han et al. | |
| 6,636,623 B2 | 10/2003 | Nelson et al. | |
| 6,637,463 B1 | 10/2003 | Lei et al. | |
| 6,674,058 B1 | 1/2004 | Miller | |
| 6,674,525 B2 | 1/2004 | Bardell et al. | |
| 6,852,284 B1 | 2/2005 | Holl et al. | |
| 6,897,954 B2 | 5/2005 | Bishop et al. | |
| 7,024,316 B1 | 4/2006 | Ellison et al. | |
| 7,105,355 B2 | 9/2006 | Kurabayashi et al. | |
| 7,109,459 B2 | 9/2006 | Kam et al. | |
| 7,192,560 B2 | 3/2007 | Parthasarathy | |
| 7,217,573 B1 * | 5/2007 | Oshida | G01N 21/6428 250/347 |
| 7,247,274 B1 | 7/2007 | Chow | |
| 7,277,166 B2 | 10/2007 | Padmanabhan et al. | |
| 7,347,976 B2 | 3/2008 | Parthasarathy et al. | |
| 7,473,529 B1 | 1/2009 | Porter et al. | |
| 7,553,453 B2 | 6/2009 | Gu et al. | |
| 7,569,373 B2 | 8/2009 | Mori et al. | |
| 7,718,421 B2 | 5/2010 | Chen et al. | |
| 7,995,202 B2 | 8/2011 | Lundquist et al. | |
| 8,116,984 B2 | 2/2012 | Davis et al. | |
| D669,191 S | 10/2012 | Handique | |
| 8,318,109 B2 | 11/2012 | Saltsman et al. | |
| 8,364,418 B2 | 1/2013 | Davis et al. | |
| 8,518,705 B2 | 8/2013 | Chan et al. | |
| 8,945,913 B2 | 2/2015 | Kasdan et al. | |
| 9,029,158 B2 | 5/2015 | Tai et al. | |
| 9,207,239 B2 | 12/2015 | Kasdan et al. | |
| 9,234,884 B2 | 1/2016 | Tai et al. | |
| 9,354,176 B2 | 5/2016 | Nishikawa | |
| 9,535,059 B2 | 1/2017 | Tai et al. | |
| 9,757,729 B2 | 9/2017 | Tai et al. | |
| 9,989,523 B2 | 6/2018 | Kasdan et al. | |
| 2001/0008760 A1 | 7/2001 | King et al. | |
| 2001/0027745 A1 | 10/2001 | Weigl et al. | |
| 2001/0030290 A1 | 10/2001 | Stern | |
| 2001/0049689 A1 * | 12/2001 | Mentzer | G06F 19/28 |
| 2002/0028519 A1 | 3/2002 | Yguerabide et al. | |
| 2002/0031255 A1 | 3/2002 | Kasdan et al. | |
| 2002/0037520 A1 | 3/2002 | Nikiforov et al. | |
| 2002/0090644 A1 | 7/2002 | Weigl et al. | |
| 2002/0113961 A1 | 8/2002 | Gamble et al. | |
| 2002/0164636 A1 * | 11/2002 | Pruitt | C12N 15/1034 435/6.14 |
| 2002/0168784 A1 | 11/2002 | Sundrehagen et al. | |
| 2002/0177174 A1 | 11/2002 | Zock et al. | |
| 2003/0002037 A1 | 1/2003 | Kasdan et al. | |
| 2003/0073089 A1 | 4/2003 | Mauze et al. | |
| 2003/0103981 A1 | 6/2003 | Spancake et al. | |
| 2003/0153844 A1 | 8/2003 | Smith et al. | |
| 2003/0170881 A1 | 9/2003 | Davis et al. | |
| 2003/0175990 A1 * | 9/2003 | Hayenga | G01N 15/1404 436/180 |
| 2003/0194752 A1 | 10/2003 | Anderson et al. | |
| 2003/0212424 A1 * | 11/2003 | Briggs | A61B 5/14546 606/181 |
| 2003/0233827 A1 | 12/2003 | Kuo et al. | |
| 2004/0053290 A1 | 3/2004 | Terbrueggen et al. | |
| 2004/0115838 A1 | 6/2004 | Quake et al. | |
| 2004/0126008 A1 | 7/2004 | Chapoulaud et al. | |
| 2004/0155309 A1 | 8/2004 | Sorin et al. | |
| 2004/0191783 A1 * | 9/2004 | Leclercq | C12Q 1/6837 506/16 |
| 2004/0217256 A1 | 11/2004 | Ortyn et al. | |
| 2004/0248205 A1 | 12/2004 | Stern et al. | |
| 2005/0069958 A1 * | 3/2005 | Mills | G01N 33/54313 435/7.2 |
| 2005/0105077 A1 * | 5/2005 | Padmanabhan | G01N 15/1484 356/39 |
| 2005/0118723 A1 | 6/2005 | Padmanabhan | |
| 2005/0121596 A1 | 6/2005 | Kam et al. | |
| 2005/0148093 A1 | 7/2005 | Chien | |
| 2005/0154268 A1 | 7/2005 | Hwang et al. | |
| 2005/0181466 A1 | 8/2005 | Dambinova et al. | |
| 2005/0221281 A1 | 10/2005 | Ho | |
| 2005/0255001 A1 | 11/2005 | Padmanabhan et al. | |
| 2005/0255600 A1 | 11/2005 | Padmanabhan et al. | |
| 2005/0261560 A1 | 11/2005 | Ridder et al. | |
| 2005/0275839 A1 | 12/2005 | Robinson et al. | |
| 2006/0011539 A1 | 1/2006 | Lee et al. | |
| 2006/0011862 A1 | 1/2006 | Bernstein et al. | |
| 2006/0134712 A1 | 6/2006 | Stromgren et al. | |
| 2006/0205012 A1 | 9/2006 | DeBad et al. | |
| 2006/0215155 A1 | 9/2006 | Weber | |
| 2006/0246575 A1 | 11/2006 | Lancaster et al. | |
| 2006/0263888 A1 | 11/2006 | Fritz et al. | |
| 2006/0269446 A1 | 11/2006 | Gilbert et al. | |
| 2007/0031289 A1 | 2/2007 | Cox et al. | |
| 2007/0059685 A1 | 3/2007 | Kohne | |
| 2007/0098594 A1 | 5/2007 | Elkin et al. | |
| 2007/0183935 A1 * | 8/2007 | Clemmens | B01F 11/0071 422/400 |
| 2007/0190525 A1 | 8/2007 | Gu et al. | |
| 2007/0227890 A1 | 10/2007 | Ramsey et al. | |
| 2007/0253868 A1 | 11/2007 | Beebe et al. | |
| 2007/0281311 A1 | 12/2007 | Roth et al. | |
| 2007/0292941 A1 | 12/2007 | Handique et al. | |
| 2008/0038873 A1 | 2/2008 | Tanida et al. | |
| 2008/0101993 A1 | 5/2008 | Andersson et al. | |
| 2008/0176253 A1 | 7/2008 | Christodoulides et al. | |
| 2008/0212102 A1 | 9/2008 | Nuzzo et al. | |
| 2008/0213854 A1 * | 9/2008 | Wirth | G01N 27/44756 435/173.6 |

(56) References Cited

U.S. PATENT DOCUMENTS

| | | |
|---|---|---|
| 2009/0042241 A1 | 2/2009 | Yu-Chong et al. |
| 2009/0117605 A1 | 5/2009 | Davis et al. |
| 2009/0148847 A1 | 6/2009 | Kokoris et al. |
| 2009/0181411 A1 | 7/2009 | Battrell et al. |
| 2009/0233300 A1 | 9/2009 | Saavedra et al. |
| 2010/0051124 A1 | 3/2010 | Imran |
| 2010/0056383 A1 | 3/2010 | Ririe et al. |
| 2010/0093019 A1 | 4/2010 | Ditcham et al. |
| 2010/0120083 A1 | 5/2010 | Ritzen et al. |
| 2010/0255473 A1 | 10/2010 | Ermantraut et al. |
| 2011/0094577 A1 | 4/2011 | Chatterjee et al. |
| 2011/0184537 A1 | 7/2011 | Kasdan et al. |
| 2012/0071342 A1 | 3/2012 | Lochhead et al. |
| 2012/0164036 A1* | 6/2012 | Stern .................. B01L 3/50273 422/502 |
| 2012/0164627 A1 | 6/2012 | Battrell et al. |
| 2012/0177543 A1 | 7/2012 | Battrell et al. |
| 2012/0187117 A1 | 7/2012 | Weber |
| 2012/0275972 A1 | 11/2012 | Schoen et al. |
| 2012/0280143 A1 | 11/2012 | Kim et al. |
| 2012/0329878 A1 | 12/2012 | Coussens et al. |
| 2013/0065269 A1 | 3/2013 | Nitta |
| 2013/0102087 A1 | 4/2013 | Kasdan et al. |
| 2013/0115607 A1* | 5/2013 | Nielsen .................. C12Q 1/68 435/6.12 |
| 2013/0130262 A1 | 5/2013 | Battrell et al. |
| 2013/0130400 A1 | 5/2013 | Harbers et al. |
| 2013/0137135 A1 | 5/2013 | Tai et al. |
| 2013/0177543 A1 | 7/2013 | Patel et al. |
| 2013/0230867 A1 | 9/2013 | Davis et al. |
| 2013/0314705 A1 | 11/2013 | Tanabe et al. |
| 2013/0323737 A1 | 12/2013 | Zenhausern et al. |
| 2013/0323825 A1 | 12/2013 | Sekino et al. |
| 2014/0033809 A1 | 2/2014 | Bransky et al. |
| 2014/0170678 A1 | 6/2014 | Kasdan et al. |
| 2014/0194305 A1 | 7/2014 | Kayyem et al. |
| 2014/0273188 A1 | 9/2014 | Mohan et al. |
| 2014/0287435 A1 | 9/2014 | Kasdan et al. |
| 2014/0377742 A1 | 12/2014 | Tai et al. |
| 2015/0004717 A1 | 1/2015 | McDevitt et al. |
| 2015/0132776 A1 | 5/2015 | Kasdan et al. |
| 2015/0309011 A1 | 10/2015 | Tai et al. |
| 2015/0338401 A1 | 11/2015 | Ram |
| 2016/0146793 A1 | 5/2016 | Kasdan et al. |
| 2017/0136463 A1 | 5/2017 | Tai et al. |

FOREIGN PATENT DOCUMENTS

| | | |
|---|---|---|
| CN | 101300478 A | 11/2008 |
| CN | 101389947 A | 3/2009 |
| CN | 101765462 A | 6/2010 |
| CN | 101848765 A | 9/2010 |
| CN | 102513168 A | 6/2012 |
| EP | 1263533 A2 | 12/2002 |
| EP | 1846159 A2 | 10/2007 |
| JP | 2008544214 A | 12/2008 |
| JP | 2008545141 A | 12/2008 |
| JP | 2009529883 A | 8/2009 |
| JP | 2012508879 A | 4/2012 |
| JP | 2012132879 A | 7/2012 |
| WO | WO/2001/068238 A2 | 9/2001 |
| WO | WO/2006/055816 A2 | 5/2006 |
| WO | WO/2006/079082 A2 | 7/2006 |
| WO | WO/2006/118586 A2 | 11/2006 |
| WO | WO/2007/076549 A2 | 7/2007 |
| WO | WO/2008/121828 A2 | 10/2008 |
| WO | WO/2008/124589 A2 | 10/2008 |
| WO | WO/2009/003493 A2 | 1/2009 |
| WO | WO/2009/144660 A1 | 12/2009 |
| WO | WO/2011/094577 A2 | 8/2011 |
| WO | WO/2011/128893 A2 | 10/2011 |
| WO | WO/2012/019599 A2 | 2/2012 |
| WO | WO/2012/020257 A1 | 2/2012 |
| WO | WO/2012/092010 A2 | 7/2012 |
| WO | WO/2012/120506 A2 | 9/2012 |
| WO | WO/2012/170711 A1 | 12/2012 |
| WO | WO/2014/097286 A1 | 6/2014 |
| WO | WO/2014/097287 A1 | 6/2014 |

OTHER PUBLICATIONS

Adams, L. R., & Kamentsky, L. A. (1974). Fluorometric characterization of six classes of human leukocytes. Acta cytologica, 18(5), 389.

Altendorf, E., Zebert, D., Holl, M., & Yager, P. (Jun. 1997). Differential blood cell counts obtained using a microchannel based flow cytometer. In Proceedings of International Solid State Sensors and Actuators Conference (Transducers' 97) (vol. 1, pp. 531-534). IEEE.

Aouani, H., Deiss, F., Wenger, J., Ferrand, P., Sojic, N., & Rigneault, H. (2009). Optical-fiber-microsphere for remote fluorescence correlation spectroscopy. Optics express, 17(21), 19085-19092.

Assicot, M., Bohuon, C., Gendrel, D., Raymond, J., Carsin, H., & Guilbaud, J. (1993). High serum procalcitonin concentrations in patients with sepsis and infection. The Lancet, 341(8844), 515-518.

Aulesa, C., Pastor, I., Naranjo, D., Piqueras, J., & Galimany, R. (2003). Validation of the Coulter LH 750 in a hospital reference laboratory. Laboratory Hematology, 9, 15-28.

Ault, K. A. (1993). Flow Cytometric Measurement of Platelet Function and Reticulated Platelets: Brief Description of Platelets. Annals of the New York Academy of Sciences, 677(1), 293-308.

Bellows—definition from the Columbia Electronic EncyclopediaCopyright 2013, Columbia University Press. Licensed from Columbia University Press. All rights reserved, www.cc.columbia.edu/cu/cup/.

Bhattacharya, S., Datta, A., Berg, J. M., & Gangopadhyay, S. (2005). Studies on surface wettability of poly (dimethyl) siloxane (PDMS) and glass under oxygen-plasma treatment and correlation with bond strength. Journal of microelectromechanical systems, 14(3), 590-597.

Björnsson, S., Wahlstrom, S., Norström, E., Bernevi, I., O'Neill, U., Johansson, E., . . . & Simonsson, P. (2008). Total nucleated cell differential for blood and bone marrow using a single tube in a five-color flow cytometer. Cytometry Part B: Clinical Cytometry, 74(2), 91-103.

Blajchman, M. A., Beckers, E. A., Dickmeiss, E., Lin, L., Moore, G., & Muylle, L. (2005). Bacterial detection of platelets: current problems and possible resolutions. Transfusion medicine reviews, 19(4), 259-272.

Bodensteiner, D. C. (1989). A flow cytometric technique to accurately measure post-filtration white blood cell counts. Transfusion, 29(7), 651-653.

Buhlmann, C., Preckel, T., Chan, S., Luedke, G., & Valer, M. (2003). A new tool for routine testing of cellular protein expression: integration of cell staining and analysis of protein expression on a microfluidic chip-based system. Journal of biomolecular techniques: JBT, 14(2), 119.

Chen, H. T., & Wang,Y. N. (2008). Fluorescence detection in a micro flow cytometer without on-chip fibers. Microfluidics and nanofluidics, 5(5), 689-694.

Cheson, B. D., Bennett, J. M., Greyer, M., Kay, N., Keating, M. J., O'Brien, S., & Rai, K. R. (1996). National Cancer Institute-sponsored Working Group guidelines for chronic lymphocytic leukemia: revised guidelines for diagnosis and treatment. Blood, 87(12), 4990-4997.

Christ-Crain, M., Jaccard-Stolz, D., Bingisser, R., Gencay, M. M., Huber, P. R., Tamm, M., & Müller, B. (2004). Effect of procalcitonin-guided treatment on antibiotic use and outcome in lower respiratory tract infections: cluster-randomised, single-blinded intervention trial. The Lancet, 363(9409), 600-607.

Cristofanilli, M., Budd, G. T., Ellis, M. J., Stopeck, A., Matera, J., Miller, M. C., . . . & Hayes, D. F. (2004). Circulating tumor cells, disease progression, and survival in metastatic breast cancer. New England Journal of Medicine, 351(8), 781-791.

(56) References Cited

OTHER PUBLICATIONS

Cui, L., Zhang, T., & Morgan, H. (2001). Optical particle detection integrated in a dielectrophoretic lab-on-a-chip. Journal of Micromechanics and Microengineering, 12(1), 7.
Davis, B. H., Olsen, S. H., Ahmad, E., & Bigelow, N. C. Neutrophil CD64 is an Improved Indicator of Infection or Sepsis in Emergency Room Patients.
Dieye, T. N., Vereecken, C., Diallo, A. A., Ondoa, P., Diaw, P. A., Camara, M., . . . & Kestens, L. (2005). Absolute CD4 T-cell counting in resource-poor settings: direct volumetric measurements versus bead-based clinical flow cytometry instruments. JAIDS Journal of Acquired Immune Deficiency Syndromes, 39(1), 32-37.
Dittrich, P. S., & Manz, A. (2005). Single-molecule fluorescence detection in microfluidic channels—the Holy Grail in µTAS?. Analytical and bioanalytical chemistry, 382(8), 1771-1782.
Dittrich, P. S., & Schwille, P. (2003). An integrated microfluidic system for reaction, high-sensitivity detection, and sorting of fluorescent cells and particles. Analytical chemistry, 75(21), 5767-5774.
Divers, S. G., Kannan, K., Stewart, R. M., Betzing, K. W., Dempsey, D., Fukuda, M., . . . & Holcombe, R. F. (1995). Quantitation of CD62, soluble CD62, and lysosome-associated membrane proteins 1 and 2 for evaluation of the quality of stored platelet concentrates. Transfusion, 35(4), 292-297.
Drexler, H. G., Menon, M., Gignac, S. M., Misra, B., & Minowada, J. (1986). Diagnostic value of immunological leukemia phenotyping. Acta haematologica, 76(1), 1-8.
Dziegiel, M. H., Nielsen, L. K., & Berkowicz, A. (2006). Detecting fetomaternal hemorrhage by flow cytometry. Current opinion in hematology, 13(6), 490-495.
Ernst, D., Bolton, G., Recktenwald, D., Cameron, M. J., Danesh, A., Persad, D., . . . & Gaur, A. (2006). Bead-based flow cytometric assays: A multiplex assay platform with applications in diagnostic microbiology. In Advanced techniques in diagnostic microbiology (pp. 427-443). Springer, Boston, MA.
European Search Report dated Jan. 29, 2019 for corresponding European Patent Application No. EP18194844.9, filed Dec. 17, 2013.
European Search Report dated Mar. 1, 2016 for corresponding European Patent Application No. EP11768557.8, filed Apr. 11, 2011.
European Search Report dated Oct. 28, 2016 for corresponding European Patent Application No. EP13864008.1, filed Dec. 17, 2013.
European Search Report dated Sep. 19, 2017 for corresponding European Patent Application No. EP17173498.1, filed Apr. 11, 2011.
European Search Report dated Sep. 21, 2016 for corresponding European Patent Application No. EP13865771.3, filed Dec. 17, 2013.
Ferris, M. M., McCabe, M. O., Doan, L. G., & Rowlen, K. L. (2002). Rapid enumeration of respiratory viruses. Analytical chemistry, 74(8), 1849-1856.
Fischer, J. C., Quenzel, E. M., Moog, R., Wenzel, F., Riethmacher, R., Tutschek, B., & Giers, G. (2011). Reducing costs in flow-cytometric counting of residual white blood cells in blood products: utilization of a single-platform bead-free flow-rate calibration method. Transfusion, 51(7), 1431-1438.
Frengen, J., Kierulf, B., Schmid, R., Lindmo, T., & Nustad, K. (1994). Demonstration and minimization of serum interference in flow cytometric two-site immunoassays. Clinical chemistry, 40(3), 420-425.
Frengen, J., Schmid, R., Kierulf, B., Nustad, K., Paus, E., Berge, A., & Lindmo, T. (1993). Homogeneous immunofluorometric assays of alpha-fetoprotein with macroporous, monosized particles and flow cytometry. Clinical chemistry, 39(10), 2174-2181.
Fujimoto, K. (1999). Principles of measurement in hematology analyzers manufactured by Sysmex Corporation. Sysmex Journal International, 9(1; SEAS SUM), 31-44.

Gawad, S., Schild, L., & Renaud, P. (2001). Micromachined impedance spectroscopy flow cytometer for cell analysis and particle sizing. Lab on a Chip, 1(1), 76-82.
Gmitro, A. F., & Aziz, D. (1993). Confocal microscopy through a fiber-optic imaging bundle. Optics letters, 18(8), 565-567.
Gosling, J. P. (1990). A decade of development in immunoassay methodology. Clinical chemistry, 36(8), 1408-1427.
Graff, J., Klinkhardt, U., Schini-Kerth, V. B., Harder, S., Franz, N., Bassus, S., & Kirchmaier, C. M. (2002). Close relationship between the platelet activation marker CD62 and the granular release of platelet-derived growth factor. Journal of Pharmacology and Experimental Therapeutics, 300(3), 952-957.
Groselj-Grenc, M., Ihan, A., & Derganc, M. (2008). Neutrophil and monocyte CD64 and CD163 expression in critically ill neonates and children with sepsis: comparison of fluorescence intensities and calculated indexes. Mediators of inflammation, 2008.
Guerti, K., Vertessen, F., Daniëls, L., & Van Der Planken, M. (2009). Performance evaluation of the PENTRA 60C+ automated hematology analyzer and comparison with the ADVIA 2120. International journal of laboratory hematology, 31(2), 132-141.
Hammatsu Photonics K.K. Electron Tube Division. Photon Counting Using Photomultiplier Tubes [online]. Jul. 2005 (See bottom right of last page) [retrieve on Sep. 13, 2011], Retrieved from the Internet: <http://sales.hamamatsu.com/assets/applications/ETD/PhotonCounting_TPH09001E04.pdf>: table.1-2; p. 1, Introduction, p. 2, Fig. 2, p. 9, Section 3-1 and p. 14, col. 1.
Hawkins, R. C. (2007). Laboratory turnaround time. The Clinical Biochemist Reviews, 28(4), 179.
Hayenga, J., Bardell, R., Morris, C., Graham, P., Kesler, N., Lancaster, C., . . . & Saltsman, P. (2002). Enabling Technologies for a Personal Flow Cytometer, Part II: Integrated Analysis Cartridges. In Micro Total Analysis Systems 2002 (pp. 207-209). Springer, Dordrecht.
Hershman, M. J., Cheadle, W. G., Wellhausen, S. R., Davidson, P. F., & Polk Jr, H. C. (1990). Monocyte HLA-DR antigen expression characterizes clinical outcome in the trauma patient. British Journal of Surgery, 77(2), 204-207.
Hilfrich, R., & Hariri, J. (2008). Prognostic relevance of HPV L1 capsid protein detection within mild to moderate dysplastic lesions of the cervix uteri in combination with a second biomarker p. 16. Anal Quant Cytol Histol, 30(2), 78-82.
Hillier, S. L., Martius, J., Krohn, M., Kiviat, N., Holmes, K. K., & Eschenbach, D. A. (1988). A case-control study of chorioamnionic infection and histologic chorioamnionitis in prematurity. New England Journal of Medicine, 319(15), 972-978.
Hoffmann, J. J. (2011). Neutrophil CD64 as a sepsis biomarker. Biochemia medica: Biochemia medica, 21(3), 282-290.
Holmes, D., Morgan, H., & Green, N. G. (2006). High throughput particle analysis: Combining dielectrophoretic particle focussing with confocal optical detection. Biosensors and Bioelectronics, 21(8), 1621-1630.
Holmes, D., Pettigrew, D., Reccius, C. H., Gwyer, J. D., van Berkel, C., Holloway, J., . . . & Morgan, H. (2009). Leukocyte analysis and differentiation using high speed microfluidic single cell impedance cytometry. Lab on a Chip, 9(20), 2881-2889.
Hughes-Jones, N. C., Norley, I., Young, J. M., & England, J. M. (1974). Differential white cell counts by frequency distribution analysis of cell volumes. Journal of clinical pathology, 27(8), 623-625.
International Preliminary Report on Patentability—Chapter I issued Oct. 16, 2012 for PCT/IL2011/000296 filed Apr. 11, 2011.
International Preliminary Report on Patentability—Chapter I issued Jun. 23, 2015 for PCT/IL2013/000092 filed Dec. 17, 2013.
International Preliminary Report on Patentability—Chapter I issued Jun. 23, 2015 for PCT/IL2013/000093 filed Dec. 17, 2013.
International Search Report dated Jan. 3, 2012 for PCT/IL2011/000296 filed Apr. 11, 2011.
International Search Report dated Apr. 1, 2014 for PCT/IL2013/000092 filed Dec. 17, 2013.
International Search Report dated Apr. 2, 2014 for PCT/IL2013/000093 filed Dec. 17, 2013.
Jackson, J. F. (1961). Supravital blood studies, using acridine orange fluorescence. Blood, 17(5), 643-649.

(56) References Cited

OTHER PUBLICATIONS

Kass, L. (1981). Chlorazol black E: A new stain for granulocytic cells. Am J Clin Pathol, 76, 810-812.

Kass, L. (1988). Identification of lymphocyte subpopulations with a polymethine dye. Journal of Histochemistry & Cytochemistry, 36(7), 711-715.

Kibe, S., Adams, K., & Barlow, G. (2011). Diagnostic and prognostic biomarkers of sepsis in critical care. Journal of antimicrobial chemotherapy, 66(suppl_2), ii33-ii40.

Kostner, S., & Vellekoop, M. J. (2008). Cell analysis in a microfluidic cytometer applying a DVD pickup head. Sensors and Actuators B: Chemical, 132(2), 512-517.

Krogmeier, J. R. Schaefer, I. Seward, G. Yantz, G. R., & Larson, J. W. (2007). An integrated optics microfluidic device for detecting single DNA molecules. Lab on a Chip, 7(12), 1767-1774.

Kunst B. H., Schots, A., & Visser, A. J. (2004). Design of a confocal microfluidic particle sorter using fluorescent photon burst detection. Review of scientific instruments, 75(9), 2892-2898.

LaRosa, S. P., & Opal, S. M. (2011). Biomarkers: the future. Critical care clinics, 27(2), 407-419.

Lee, D. W., Yi, S., & Cho, Y. H. (Jan. 2005). A flow-rate independent cell counter using a fixed control vol. between double electrical sensing zones. In 18th IEEE International Conference on Micro Electro Mechanical Systems, 2005. MEMS 2005. (pp. 678-681). IEEE.

Lee, G. B., Lin, C. H., & Chang, S. C. (2004). Micromachine-based multi-channel flow cytometers for cell/particle counting and sorting. Journal of Micromechanics and Microengineering, 15(3), 447.

Lin et al. ("Microfluidic Immunoassays," JALA, 2010, 15, 253-275).

Liu, N. I. N. G., Wu, A. H., & Wong, S. S. (1993). Improved quantitative Apt test for detecting fetal hemoglobin in bloody stools of newborns. Clinical chemistry, 39(11), 2326-2329.

Liu, P., Seo, T. S., Beyor, N., Shin, K. J., Scherer, J. R., & Mathies, R. A. (2007). Integrated portable polymerase chain reaction-capillary electrophoresis microsystem for rapid forensic short tandem repeat typing. Analytical chemistry, 79(5), 1881-1889.

Lotan, Y., Elias, K., Svatek, R. S., Bagrodia, A., Nuss, G., Moran, B., & Sagalowsky, A. I. (2009). Bladder cancer screening in a high risk asymptomatic population using a point of care urine based protein tumor marker. The Journal of urology, 182(1), 52-58.

Masse, M., Naegelen, C., Pellegrini, N., Segier, J. M., Marpaux, N., & Beaujean, F. (1992). Validation of a simple method to count very low white cell concentrations in filtered red cells or platelets. Transfusion, 32(6), 565-571.

Matic, G. B., Chapman, E. S., Zaiss, M., Rothe, G., & Schmitz, G. (1998). Whole blood analysis of reticulated platelets: improvements of detection and assay stability. Cytometry: The Journal of the International Society for Analytical Cytology, 34(5), 229-234.

McDonald, C. P., Colvin, J., Robbins, S., & Barbara, J. A. J. (2005). Use of a solid-phase fluorescent cytometric technique for the detection of bacteria in platelet concentrates. Transfusion Medicine, 15(3), 175-183.

Michelson, A. D. (1996). Flow cytometry: a clinical test of platelet function. Open Access Articles, 290.

Miller, E. M., Freire, S., & Wheeler, A. R. (2008). Proteomics in Microfluidic Devices. Encyclopedia of Microfluidics and Nanofluidics, 1749-1758.

Morgan, H., Holmes, D., & Green, N. G. (2006). High speed simultaneous single particle impedance and fluorescence analysis on a chip. Current Applied Physics, 6(3), 367-370.

Moriyama, Y., Takano, T., & Ohkuma, S. (1982). Acridine orange as a fluorescent probe for lysosomal proton pump. The Journal of Biochemistry, 92(4), 1333-1336.

Moro, R., Tcherkassova, J., Song, E., Shen, G., Moro, R., Schmid, R., . . . & Chen, C. (2005). A new broad-spectrum cancer marker. Vitro Diagnostic Technology.

Niehren, S., Kinzelbach, W., Seeger, S., & Wolfrum, J. (1995). An all-solid-state flow cytometer for counting fluorescent microspheres. Analytical Chemistry, 67(15), 2666-2671.

Oberjat, T. E., Zucker, R. M., & Cassen, B. (1970). Rapid and reliable differential counts on dilute leukocyte suspensions. The Journal of laboratory and clinical medicine, 76(3), 518-522.

Ozanich Jr, R. M., Bruckner-Lea, C. J., Warner, M. G., Miller, K., Antolick, K. C., Marks, J. D., . . . & Grate, J. W. (2009). Rapid multiplexed flow cytometric assay for botulinum neurotoxin detection using an automated fluidic microbead-trapping flow cell for enhanced sensitivity. Analytical chemistry, 81(14), 5783-5793.

Pál, J., Pálinkás, L., Nyárády, Z., Czömpöly, T., Marczinovits, I., Lustyik, G., . . . & Pár, A. (2005). Sandwich type ELISA and a fluorescent cytometric microbead assay for quantitative determination of hepatitis B virus X antigen level in human sera. Journal of immunological methods, 306(1-2), 183-192.

Patibandla, P. K., Estrada, R., Kannan, M., & Sethu, P. (2014). A microfluidics-based technique for automated and rapid labeling of cells for flow cytometry. Journal of Micromechanics and Microengineering, 24(3), 034002.

Perry, S. E., Mostafa, S. M., Wenstone, R., Shenkin, A., & McLaughlin, P. J. (2003). Is low monocyte HLA-DR expression helpful to predict outcome in severe sepsis?. Intensive care medicine, 29(8), 1245-1252.

Piyasena, M. E., & Graves, S. W. (2014). The intersection of flow cytometry with microfluidics and microfabrication. Lab on a Chip, 14(6), 1044-1059.

Preckel, T., Luedke, G., Chan, S. D., Wang, B. N., Dubrow, R., & Buhlmann, C. (2002). Detection of cellular parameters using a microfluidic chip-based system. JALA: Journal of the Association for Laboratory Automation, 7(4), 85-89.

Ramakumar, S., Bhuiyan, J., Besse, J. A., Roberts, S. G., Wollan, P. C., Blute, M. L., & O'kane, D. J. (1999). Comparison of screening methods in the detection of bladder cancer. The Journal of urology, 161(2), 388-394.

Rawstron, A. C., Kennedy, B., Evans, P. A., Davies, F. E., Richards, S. J., Haynes, A. P., . . . & Hillmen, P. (2001). Quantitation of minimal disease levels in chronic lymphocytic leukemia using a sensitive flow cytometric assay improves the prediction of outcome and can be used to optimize therapy. Blood, 98(1), 29-35.

Rodriguez, W. R., Christodoulides, N., Floriano, P. N., Graham, S., Mohanty, S., Dixon, M., . . . & Romanovicz, D. (2005). A microchip CD4 counting method for HIV monitoring in resource-poor settings. PLoS medicine, 2(7), e182.

Rylatt, D. B., Blake, A. S., Cottis, L. E., Massingham, D. A., Fletcher, W. A., Masci, P. P., . . . & Wyatt, D. (1983). An immunoassay for human D dimer using monoclonal antibodies. Thrombosis research, 31(6), 767-778.

Sacks, D. B., Bruns, D. E., Goldstein, D. E., Maclaren, N. K., McDonald, J. M., & Parrott, M. (2002). Guidelines and recommendations for laboratory analysis in the diagnosis and management of diabetes mellitus. Clinical chemistry, 48(3), 436-472.

Satake, D., Ebi, H., Oku, N., Matsuda, K., Takao, H., Ashiki, M., & Ishida, M. (2002). A sensor for blood cell counter using MEMS technology. Sensors and Actuators B: Chemical, 83(1-3), 77-81.

Schwartz, M. K., Bethune, V. G., Fleisher, M., Pennacchia, G., Menendez-Botet, C. J., & Lehman, D. (1974). Chemical and Clinical Evaluation of the Continuous-flow Analyzer"SMAC". Clinical chemistry, 20(8), 1062-1070.

Segal, H. C., Briggs, C., Kunka, S., Casbard, A., Harrison, P., Machin, S. J., & Murphy, M. F. (2005). Accuracy of platelet counting haematology analysers in severe thrombocytopenia and potential impact on platelet transfusion. British journal of haematology, 128(4), 520-525.

Shapiro, H. M. & Perlmutter, N. G. (2006). Personal cytometers: slow flow or no flow?. Cytometry part A, 69(7), 620-630.

Shapiro, H. M., Schildkraut, E. R., Curbelo, R., Laird, C. W., Turner, B., & Hirschfeld, T. (1976). Combined blood cell counting and classification with fluorochrome stains and flow instrumentation. Journal of Histochemistry & Cytochemistry, 24(1), 396-401.

Shapiro, H. M., Schildkraut, E. R., Curbelo, R., Turner, R. B., Webb, R. H., Brown, D. C., & Block, M. J. (1977). Cytomat-R: a computer-controlled multiple laser source multiparameter flow cytophotometer system. Journal of Histochemistry & Cytochemistry, 25(7), 836-844.

(56) References Cited

OTHER PUBLICATIONS

Sheehan, H. L., & Storey, G. W. (1947). An improved method of staining leucocyte granules with Sudan black B. The Journal of pathology and bacteriology, 59(1-2), 336-337.

Simonnet, C., & Groisman, A. (2006). High-throughput and high-resolution flow cytometry in molded microfluidic devices. Analytical chemistry, 78(16), 5653-5663.

Skeggs, L. T., & Hochstrasser, H. (1964). Multiple automatic sequential analysis. Clinical Chemistry, 10(10), 918-936.

Smal, I., Draegestein, K., Galjart, N., Niessen, W., & Meijering, E. (2008). Particle filtering for multiple object tracking in dynamic fluorescence microscopy images: Application to microtubule growth analysis. IEEE transactions on medical imaging, 27(6), 789-804.

Stein, P. D., Hull, R. D., Patel, K. C., & Gould, M. K. (2004). Review: of the various D-dimer assays, negative ELISA results are most useful for excluding a diagnosis of deep venous thrombosis or pulmonary embolism/Commentary. ACP Journal Club, 141(3), 77.

Stein, P. D., Hull, R. D., Patel, K. C., Olson, R. E., Ghali, W. A., Brant, R., . . . & Kalra, N. K. (2004). D-dimer for the exclusion of acute venous thrombosis and pulmonary embolism: a systematic review. Annals of internal medicine, 140(8), 589-602.

Steinkamp, J. A., Romero, A., & Van, M. D. (1973). Multiparameter cell sorting: identification of human leukocytes by acridine orange fluorescence. Acta cytologica, 17(2), 113-117.

Sutherland, D. R., Anderson, L., Keeney, M., Nayar, R., & Chin-Yee, I. A. N. (1996). The ISHAGE guidelines for CD34+ cell determination by flow cytometry. Journal of hematotherapy, 5(3), 213-226.

Tatsumi, N., Tsuda, I., Furota, A., Takubo, T., Hayashi, M., & Matsumoto, H. (1999). Principle of blood cell counter-development of electric impedance method. Sysmex Journal International, 9(1; SEAS SUM), 8-20.

Tibbe, A. G., de Grooth, B. G., Greve, J., Liberti, P. A., Dolan, G. J., & Terstappen, L. W. (1999). Optical tracking and detection of immunomagnetically selected and aligned cells. Nature biotechnology, 17(12), 1210.

Tung, Y. C., Zhang, M., Lin, C. T., Kurabayashi, K., & Skerlos, S. J. (2004). PDMS-based opto-fluidic micro flow cytometer with two-color, multi-angle fluorescence detection capability using PIN photodiodes. Sensors and Actuators B: Chemical, 98(2-3), 356-367.

Van Dilla, M. A., Fulwyler, M. J., & Boone, I. U. (1967). Volume distribution and separation of normal human leucocytes. Proceedings of the Society for Experimental Biology and Medicine, 125(2), 367-370.

Wang, C., Smith, B. R., Ault, K. A., & Rinder, H. M. (2002). Reticulated platelets predict platelet count recovery following chemotherapy. Transfusion, 42(3), 368-374.

Weigl, B. H., Bardell, R., Schulte, T., Battrell, F., & Hayenga, J. (2001). Design and rapid prototyping of thin-film laminate-based microfluidic devices. Biomedical Microdevices, 3(4), 267-274.

Westgard, J. O., Carey, R. N., Feldbruegge, D. H., & Jenkins, L. M. (1976). Performance studies on the Technicon"SMAC" analyzer: Precision and comparison of values with methods in routine laboratory service. Clinical chemistry, 22(4), 489-496.

Witten Opinion of the International Search Authority dated Jan. 3, 2012 for PCT/IL2011/000296 filed Apr. 11, 2011.

Witten Opinion of the International Search Authority dated Jan. 3, 2012 for PCT/IL2013/000092 filed Dec. 17, 2013.

Witten Opinion of the International Search Authority dated Apr. 2, 2014 for PCT/IL2013/000093 filed Dec. 17, 2013.

Yang, S. Y., Hsiung, S. K., Hung, Y. C., Chang, C. M., Liao, T. L., & Lee, G. B. (2006). A cell counting/sorting system incorporated with a microfabricated flow cytometer chip. Measurement Science and Technology, 17(7), 2001.

Zhong, C. F., Ye, J. Y., Myc, A., Cao, Z., Kukowska, J., Baker, J. R., & Norris, T. B. (Oct. 2004). In vivo flow cytometry. In Frontiers in Optics (p. FTuE5). Optical Society of America.

\* cited by examiner

SYSTEMS, COMPOSITIONS AND METHODS FOR DETECTING A BIOLOGICAL CONDITION

CROSS-REFERENCE TO RELATED APPLICATIONS

This application is a continuation-in-part of U.S. patent application Ser. No. 13/716,246, filed on Dec. 17, 2012, and claims priority from U.S. Provisional Patent Application Nos. 61/737,854, to Kasdan, et al., filed on Dec. 17, 2012, and 61/737,856, to Kasdan, et al., filed on Dec. 17, 2012, the disclosures of which are incorporated herein by reference in their entirety.

FIELD OF THE INVENTION

The present invention relates generally to apparatus and methods for detecting a biological condition, and more specifically to methods and apparatus for detecting a biological condition in small fluid samples.

BACKGROUND OF THE INVENTION

There are numerous medical conditions which are hard to diagnose. Often diagnosis by a physician is based on the physician's observation of combinations of symptoms in a patient. This sometimes leads to misdiagnosis. Furthermore, the patient's response to a treatment, whether drug or other modality is often followed up by physician's observation.

Many laboratory tests are performed in the diagnostic arena on a bodily specimen or fluid to determine a biological condition in a patient. However, these tests are performed off-line in diagnostic laboratories. Often, the laboratory services are only provided during a single 8-hour shift during the day and tend to be labor intensive. Some prior art publications in the field include, inter alia, U.S. Pat. No. 8,116,984, US2006215155 and US2012187117.

Despite the inventions mentioned hereinabove, there still remains an unmet need to provide improved apparatus and methods for detecting and diagnosing biological conditions in a patient.

SUMMARY OF THE INVENTION

It is an object of some aspects of the present invention to provide improved apparatus and methods for detecting and diagnosing biological conditions in a patient.

In some embodiments of the present invention, improved methods, apparatus and systems are provided for detecting and diagnosing a biological condition in a patient.

In other embodiments of the present invention, a method and system is described for providing rapid detection of biological moieties in a sample from a patient.

In further embodiments of the present invention, a method and system is disclosed for providing detection of biological moieties in a small fluid sample from a patient.

There is thus provided according to an embodiment of the present invention, a system for determining a biological condition, the system including;

a) a cartridge including a plurality of fluidic open channels, all the channels in liquid communication with each other, the cartridge being adapted to be sealed after receiving a fluid specimen and to pass a predetermined quantity of the specimen through at least part of the plurality of fluidic open channels; and further to vigorously contact at least one reagent stored in a sealed on-board chamber (termed herein "a blister") with the predetermined quantity of the specimen in a reaction chamber to induce a reaction and form a reaction product;

b) a mechanical controller including;
  i. a first urging means adapted to apply a force externally onto the chamber thereby breaking a frangible seal on the chamber and to release the at least one reagent;
  ii. at least one second urging means adapted to apply a removable force onto plurality of fluidic open channels thereby inducing fluidic movement in a first direction in the plurality of fluidic open channels and upon removal of the force causing fluidic movement in an opposite direction to the first direction;
  iii. an alignment means adapted to align a reading channel on the cartridge for a detection to take place;

c) an optical reader adapted to detect the reaction product in the reading channel of the sealed cartridge; and d) a processor adapted to receive data from the optical reader and to process the data to determine the biological condition;

wherein the cartridge further includes an inflatable deformable elastic chamber (termed herein "a bellows") adapted to apply at least one of a negative pressure and a positive pressure in the fluidic channels.

Additionally, according to an embodiment of the present invention, the plurality of fluidic open channels is of a cross-section of 0.1 to 2 $mm^2$.

Furthermore, according to an embodiment of the present invention, the fluid specimen is of a volume of 10 to 500 microliters.

Importantly, according to an embodiment of the present invention, the cartridge is valveless.

Moreover, according to an embodiment of the present invention, the cartridge limits processing of the fluid specimen to a fixed volume that is a fraction of the input volume.

Further, according to an embodiment of the present invention, the cartridge is a closed system after sealing.

Yet further, according to an embodiment of the present invention, the cartridge is adapted to contact a plurality of on-board reagents with at least one of the specimen and the reaction product.

Additionally, according to an embodiment of the present invention, the cartridge is adapted to induce cascaded sequential reactions of the on-board reagents with at least one of the specimen and the reaction product.

Furthermore, according to an embodiment of the present invention, the reaction chamber is of a volume of 200 to 10000 microliters.

Moreover, according to an embodiment of the present invention, the system further includes a temperature control device external to the cartridge, the device being adapted to control wherein the cartridge is adapted to contact a temperature of the reaction.

Importantly, according to an embodiment of the present invention, the cartridge has a shelf-life of 6 to 24 months.

Notably, according to an embodiment of the present invention, the cartridge is static within the system.

Additionally, according to an embodiment of the present invention, the fluid specimen is introduced to the cartridge via capillary action.

Furthermore, according to an embodiment of the present invention, the cartridge includes at least one of the following elements;
i. a reservoir;
ii. a pump;
iii. a conduit;

iv. a miniaturized flow cell;
v. a transport channel;
vi. a reading channel;
vii. a microfluidic element;
viii. a compressed gas holding element
ix. a compressed gas releasing element;
x. a nozzle element;
xi. a mixing element;
xii. a bellows element.
xiii. software adapted to activate the elements according to a specific sequence; and
xiv. hardware to activate the elements according to a specific sequence.

Further, according to an embodiment of the present invention, the cartridge includes several of the above-mentioned elements.

Yet further, according to an embodiment of the present invention, the cartridge includes all of the above-mentioned elements.

Additionally, according to an embodiment of the present invention, the at least one composition disposed in the cartridge includes at least one of;
 a. at least one target antibody;
 b. at least one positive control identifying antibody; and
 c. at least one negative control identifying detection moiety.

Additionally, according to an embodiment of the present invention, the at least one composition disposed in the cartridge includes two of:
 a. at least one target antibody;
 b. at least one positive control identifying detection moiety; and
 c. at least one negative control identifying detection moiety.

In some cases, according to an embodiment of the present invention, the at least one composition disposed in the cartridge includes all of:
 a. at least one target antibody;
 b. at least one positive control identifying detection moiety; and
 c. at least one negative control identifying detection moiety.

Additionally, according to an embodiment of the present invention, the at least one composition disposed in the cartridge includes at least one reference composition including at least one of;
 d. a target signal reference composition; and
 e. a reference identifier composition.

Furthermore, according to an embodiment of the present invention, the at least one composition disposed in the cartridge includes at least one of;
 f. a positive control moiety; and
 g. a negative control moiety.

Moreover, according to an embodiment of the present invention, the at least one composition disposed in the cartridge includes a sepsis biomarker.

Additionally, according to an embodiment of the present invention, the biomarker includes at least one of CD64 and CD163.

There is thus provided according to an additional embodiment of the present invention, a method for determining a biological condition in a subject, the method including;
 a. incubating a specimen from the subject in the system of as described herein for a predetermined period of time; and
 b. receiving an indication responsive to the at least one reporter element thereby providing the indication of the biological condition in the subject.

Additionally, according to an embodiment of the present invention, the biological condition is selected from blood diseases such as leukemia, thrombocytopenia, immune system disorders, local infections, urinary tract disorders, autoimmune diseases and sepsis.

Importantly, according to an embodiment of the present invention, the indication is quantitative.

Additionally, according to an embodiment of the present invention, the method is completed within twenty minutes.

Notably, according to an embodiment of the present invention, the system is a flow cytometer system.

There is thus provided according to an additional embodiment of the present invention, a method for determining a biological condition in a mammalian subject, the method including;
 a. incubating a specimen from the subject with at least one composition in a system for a predetermined period of time to form at least one reaction product, when the subject has the biological condition; and
 b. receiving an indication of the at least one reaction product responsive to at least one reporter element in the system thereby providing the indication of the biological condition in the subject.

There is thus provided according to an additional embodiment of the present invention, an automated method of determining the presence or absence of sepsis in a subject, including;
 a. contacting a blood sample from the subject with a fluorescently-labeled binding moiety specific to a sepsis marker, wherein the volume of the blood sample is 50 μL or smaller;
 b. detecting the presence, absence or level of the binding moiety in the sample, thereby determining the presence or absence of sepsis in the subject within twenty minutes.

Additionally, according to an embodiment of the present invention, the sepsis marker is CD64.

Furthermore, according to an embodiment of the present invention, the sepsis marker is CD163.

Moreover, according to an embodiment of the present invention, the method further includes contacting the blood sample with a second fluorescently-labeled binding moiety specific for a second sepsis marker.

Additionally, according to an embodiment of the present invention, the sepsis marker is CD64 and the second sepsis marker is CD163.

There is thus provided according to an embodiment of the present invention, a system for evaluating a biological condition in a patient, the system comprising;
 a) a disposable element for receiving a biological specimen and for combining said specimen with at least one composition;
 b) at least one composition comprising at least one detector moiety adapted to react with said specimen to form a reaction product, when said patient has said biological condition; and
 c) at least one reporter element adapted to provide an indication of reaction product thereby providing the indication of the biological condition.

Additionally, according to an embodiment of the present invention, the system further comprises;
 d) instructions for using the system.

Furthermore, according to an embodiment of the present invention, the disposable element is a disposable cartridge.

Moreover, according to an embodiment of the present invention, the disposable cartridge is a disposable microfluidics cartridge.

Additionally, according to an embodiment of the present invention, the disposable microfluidics cartridge comprises at least one of the following elements:
- a) a reservoir;
- b) a pump;
- c) a valve;
- d) a conduit;
- e) a motor;
- f) a miniaturized flow cell;
- g) a transport channel;
- h) a microfluidic element;
- i) a compressed gas holding element;
- j) a compressed gas releasing element;
- k) a nozzle element;
- l) a mixing element;
- m) a bellows element;
- n) software adapted to activate said elements according to a specific sequence; and
- o) hardware to activate said elements according to a specific sequence.

Additionally, according to an embodiment of the present invention, the disposable microfluidics cartridge comprises at least two of the elements.

Additionally, according to an embodiment of the present invention, the disposable microfluidics cartridge comprises at least three of the elements.

Additionally, according to an embodiment of the present invention, the disposable microfluidics cartridge comprises at least four of the elements.

Additionally, according to an embodiment of the present invention, the disposable microfluidics cartridge comprises at least five of the elements.

Additionally, according to an embodiment of the present invention, the disposable microfluidics cartridge comprises at least ten of the elements.

Additionally, according to an embodiment of the present invention, the disposable microfluidics cartridge comprises at least twenty of the elements.

Additionally, according to an embodiment of the present invention, the disposable microfluidics cartridge comprises at least thirty of the elements.

According to an embodiment of the present invention, the microfluidics system is configured to provide the rapid indication with one hour.

According to another embodiment of the present invention, the microfluidics system is configured to provide the rapid indication with thirty minutes.

According to another embodiment of the present invention, the microfluidics system is configured to provide the rapid indication with fifteen minutes.

According to another embodiment of the present invention, the microfluidics system is configured to provide the rapid indication with ten minutes.

According to another embodiment of the present invention, the microfluidics system is configured to provide the rapid indication with five minutes.

According to another embodiment of the present invention, the microfluidics system is configured to provide the rapid indication with one minute.

According to another embodiment of the present invention, the microfluidics system is configured to provide the rapid indication with thirty seconds.

According to another embodiment of the present invention, the microfluidics system is configured to provide the rapid indication with ten seconds.

According to another embodiment of the present invention, the microfluidics system is configured to provide the rapid indication with one second.

There is thus provided according to an embodiment of the present invention, a microfluidics assay system for performing a rapid biological assay, the system comprising;
- a) a disposable element comprising a reactant, the disposable element being adapted to receive a sample comprising a biological entity and for combining said reactant with said biological entity to form a reaction product; and
- b) at least one reporter element adapted to provide a rapid indication of disappearance of said reactant thereby providing rapid assay of the biological entity.

There is thus provided according to an embodiment of the present invention, a microfluidics assay system for performing a rapid assay of a biological entity, the system comprising;
- a) a disposable element comprising a reactant, the disposable element being adapted to receive a sample comprising the biological entity and for combining said reactant with said biological entity to form a reaction product; and
- b) at least one reporter element adapted to provide a rapid indication of appearance of said reaction product thereby providing rapid assay of the biological entity.

There is thus provided according to an embodiment of the present invention, a composition for evaluating a biological condition, the composition comprising;
- a. a sample composition comprising at least one of;
  - i. a bodily specimen comprising a target moiety;
  - ii. a positive control moiety; and
  - iii. a negative control moiety;
- b. a detection composition comprising at least one of;
  - i. at least one target antibody;
  - ii. at least one positive control identifying antibody; and
  - iii. at least one negative control identifying detection moiety or characteristic; and
- c. at least one reference composition comprising at least one of;
  - i. a target signal reference composition; and
  - ii. a reference identifier composition.

There is thus provided according to another embodiment of the present invention a composition for evaluating a biological condition, the composition comprising;
- a. a sample composition comprising at least one of;
  - i. a bodily specimen comprising a target moiety;
  - ii. a positive control moiety; and
  - iii. a negative control moiety;
- b. an antibody composition comprising at least one of;
  - i. at least one target antibody (CD64 antibody);
  - ii. at least one positive control identifying antibody (CD 163); and
  - iii. at least one negative control identifying antibody or characteristic; and
- c. at least one reference composition comprising at least one of;
  - i. a target signal reference composition; and
  - ii. a reference identifier composition.

Additionally, according to an embodiment of the present invention, the composition further comprises at least one conditioning moiety comprising;
- d. at least one lysis reagent; and
- e. at least one diluent.

Furthermore, according to an embodiment of the present invention, the biological condition is selected from a group consisting of blood diseases such as leukemia, thrombocytopenia immune system disorders, local infections, urinary tract disorders, autoimmune diseases and sepsis.

Moreover, according to an embodiment of the present invention the bodily specimen is selected from a group consisting of blood, serum, plasma, urine, saliva, cerebrospinal fluid (CSF), serous fluid, peritoneal fluid and synovial fluid.

According to another embodiment of the present invention, the target moiety includes a CD64 surface antigen on neutrophils.

Additionally, according to a further embodiment of the present invention, the positive control moiety includes monocytes and the negative control includes lymphocytes.

Additionally, according to an embodiment of the present invention, the target moiety is CD64 on neutrophils, the positive control moiety includes CD64 expression on monocytes, and the negative control moiety includes lymphocytes without CD64 expression.

Further, according to an embodiment of the present invention, the target indicator is bound to a signaling moiety on the at least one target antibody.

Yet further, according to an embodiment of the present invention, the at least one reference composition includes beads.

Additionally, according to an embodiment of the present invention, the beads include polystyrene microbeads.

Moreover, according to an embodiment of the present invention, the target antibody reference composition includes a first fluorescent signal and the reference identifier composition includes a second fluorescent signal.

Furthermore, according to an embodiment of the present invention, the first fluorescent signal includes FITC and the second fluorescent signal includes Starfire Red fluor.

There is thus provided according to an embodiment of the present invention, a method of quantifying a biomarker in a sample, comprising;
  a. contacting the sample with a fluorescently-labeled binding moiety that specifically binds to the biomarker;
  b. detecting a first fluorescent signal from at least a portion of the labeled sample;
  c. detecting a second fluorescent signal from a population of fluorescently-labeled particles, wherein the population includes a known fluorescent intensity over a fixed time; and
  d. normalizing the first fluorescent signal to the second fluorescent signal, thereby quantifying the biomarker, wherein the normalizing includes using a device comprising software capable of comparing the first and second fluorescent signal.

Furthermore, according to an embodiment of the present invention, the biomarker is a sepsis biomarker.

Moreover, according to an embodiment of the present invention, the biomarker is CD64 or CD163.

Additionally, according to an embodiment of the present invention, the sample is a blood sample.

According to another embodiment of the present invention, the fluorescent label of the binding moiety and the fluorescent label of the particles is the same fluorescent label.

Further, according to an embodiment of the present invention, the binding moiety is an antibody.

According to an embodiment of the present invention, the software is capable of recognizing a specific lot of fluorescently-labeled particles.

Moreover, according to an embodiment of the present invention, the individual fluorescent signals include at least one first fluorescent signal and at least one second fluorescent signal.

Additionally, according to an embodiment of the present invention the fluorescently-labeled binding moiety targets a first cell population and a second cell population in the sample.

According to another embodiment of the present invention the detection of binding of the binding moiety to the second cell population provides an internal positive control for the sample.

Furthermore, according to an embodiment of the present invention, the binding moiety is anti-CD64 antibody and the first cell population includes neutrophil leukocytes.

Yet further, according to an embodiment of the present invention, the second cell population includes monocytes.

According to an embodiment of the present invention, the method further comprises the step of determining the presence of at least one cell population in the sample that is not bound by the binding moiety, thus providing an internal negative control for the sample.

There is thus provided according to another embodiment of the present invention, a composition for evaluating a biological condition, the composition comprising;
  a. a sample comprising at least one of;
    i. a bodily specimen comprising a target moiety;
    ii. a positive control moiety; and
    iii. a negative control moiety;
  b. an antibody composition comprising at least one of;
    i. at least one target antibody;
    ii. at least one positive control identifying antibody; and
    iii. at least one negative control identifying antibody or characteristic; and
  c. at least one reference composition comprising at least one of;
    i. a target antibody reference composition; and
    ii. a reference identifier composition.

According to an embodiment of the present invention, the composition further comprises at least one conditioning moiety comprising;
  a) at least one lysis reagent; and
  b) at least one diluent.

There is thus provided according to another embodiment of the present invention, a method of determining the presence or absence of sepsis in a subject, the method including;
  a) contacting a blood sample from the subject with a fluorescently-labeled binding moiety specific to a sepsis marker, wherein the volume of the blood sample is 50 µL or smaller; and
  b) detecting the presence, absence or level of the binding moiety in the sample, thereby determining the presence or absence of sepsis in the subject.

There is thus provided according to another embodiment of the present invention, a method of quantifying a biomarker in a sample, comprising;
  a) contacting the sample with a fluorescently-labeled binding moiety that specifically binds to the biomarker;
  b) detecting a first fluorescent signal from at least a portion of the labeled sample;
  c) detecting a second fluorescent signal from a population of fluorescently-labeled particles, wherein the population includes a known fluorescent intensity over a fixed time; and d) normalizing the first fluorescent signal to the second fluorescent signal, thereby quantifying the biomarker, wherein the normalizing includes using a device comprising software capable of comparing the first and second fluorescent signal.

According to some embodiments, the sample may be liquid, according to other embodiments, the sample may be a colloid or suspension. According to further embodiments, the sample may be a solid, such as in a powder or crystal form.

Typical turnaround times for diagnostic prior art assays are 30-120 minutes. Often, the time lost in waiting for laboratory results can lead to a further deterioration in a patient, and sometimes death. In some cases, the physician has to act without having the laboratory results. This can lead to providing the patient with the wrong treatment. The present invention provides rapid assays to save lives and provide fast correct treatments to a patient.

There is thus provided according to an embodiment of the present invention automated method of determining the presence or absence of sepsis in a subject, including;
a) contacting a blood sample from the subject with a fluorescently-labeled binding moiety specific to a sepsis marker, wherein the volume of the blood sample is 50 µL or smaller; and
b) detecting the presence, absence or level of the binding moiety in the sample, thereby determining the presence or absence of sepsis in the subject within twenty minutes.

Importantly, according to an embodiment of the present invention, the method is a flow cytometric method.

Additionally, according to an embodiment of the present invention, the sepsis marker is CD64.

Furthermore, according to an embodiment of the present invention, a second sepsis marker is CD163.

Moreover, according to an embodiment of the present invention, the method further includes contacting the blood sample with a second fluorescently-labeled binding moiety specific for a second sepsis marker.

Further, according to an embodiment of the present invention, the sepsis marker is CD64 and the second sepsis marker is CD163.

Additionally, according to an embodiment of the present invention, the binding moiety is an antibody.

Moreover, according to an embodiment of the present invention, the detecting step is performed in a device capable of receiving the sample and capable of detecting the binding moiety.

Additionally, according to an embodiment of the present invention, the method further includes the step of calibrating the device by detecting a population of the fluorescently-labeled particles.

According to another embodiment of the present invention, the particles include the same fluorescent label as the fluorescently-labeled binding moiety.

Additionally, according to an embodiment of the present invention, the method further includes a second population of particles that include the same fluorescent label as the second fluorescently-labeled binding moiety.

Moreover, according to an embodiment of the present invention, the method further includes performing an internal calibration after the detecting the fluorescently-labeled binding moiety.

Notably, according to an embodiment of the present invention, the calibration is completed in less than 5 minutes.

According to some embodiments, the particles are microbeads.

Additionally, according to an embodiment of the present invention, the method is performed in less than 15 minutes.

Furthermore, according to an embodiment of the present invention, the method, further includes the step of determining the presence of at least one cell population in the sample that is not bound by the binding moiety, thus providing an internal negative control for the sample.

The present invention will be more fully understood from the following detailed description of the preferred embodiments thereof, taken together with the drawings.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a simplified schematic illustration showing an apparatus for detecting a biological condition, in accordance with an embodiment of the present invention;

FIG. 2 is a simplified flow chart of a method for detecting a biological condition, in accordance with an embodiment of the present invention;

FIG. 3 is a simplified schematic illustration showing a methodology for detecting a biological condition associated with a CD64 cell surface antigen, in accordance with an embodiment of the present invention;

FIG. 4 is a simplified flow chart of a method for detecting a biological condition associated with a CD64 cell surface antigen, in accordance with an embodiment of the present invention;

FIG. 5A is a graphical output of a fluorescent detection assay of a non-activated neutrophil signature associated with the method of FIGS. 3-4, in accordance with an embodiment of the present invention;

FIG. 5B is a graphical output of a fluorescent detection assay of an activated neutrophil signature, associated with the method of FIGS. 3-4, in accordance with an embodiment of the present invention;

FIG. 5C is a graphical output of a fluorescent detection assay of a monocyte signature, associated with the method of FIGS. 3-4, in accordance with an embodiment of the present invention; FIG. 5D is a graphical output of a fluorescent detection assay of a reference bead signature, associated with the method of FIGS. 3-4, in accordance with an embodiment of the present invention;

FIG. 6 is a simplified flow chart of a method for differentiating between different particles, in accordance with an embodiment of the present invention;

FIG. 7 is a graphical output of fluorescence from reference beads in eight wavebands, in accordance with an embodiment of the present invention;

FIG. 8 is a graphical output of data from FIG. 7 after a first mathematical manipulation, in accordance with an embodiment of the present invention;

FIG. 9 is a graphical output of data from FIG. 7 after a second mathematical manipulation, in accordance with an embodiment of the present invention;

Figure 7:
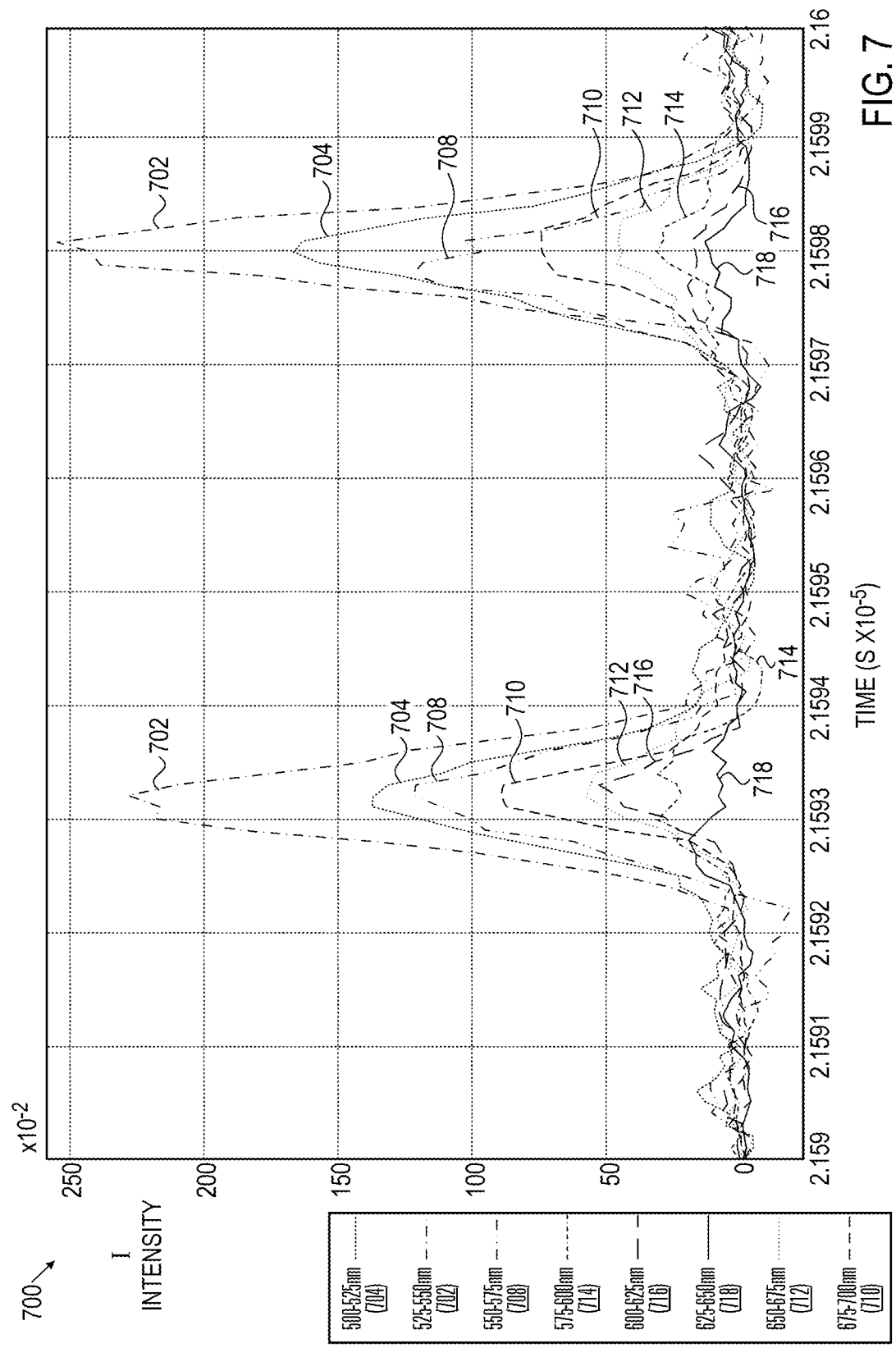
Figure 8:
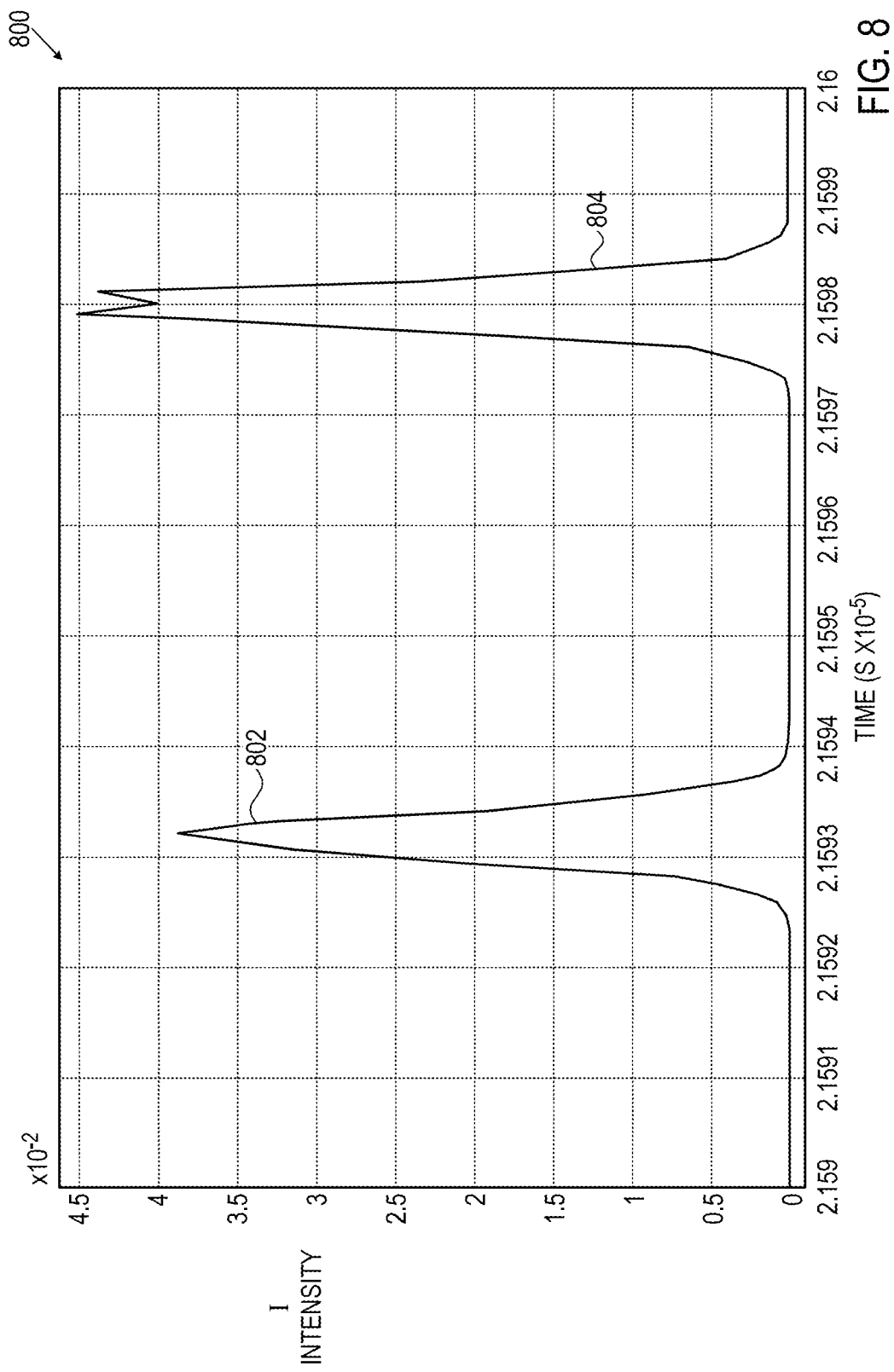
Figure 9:
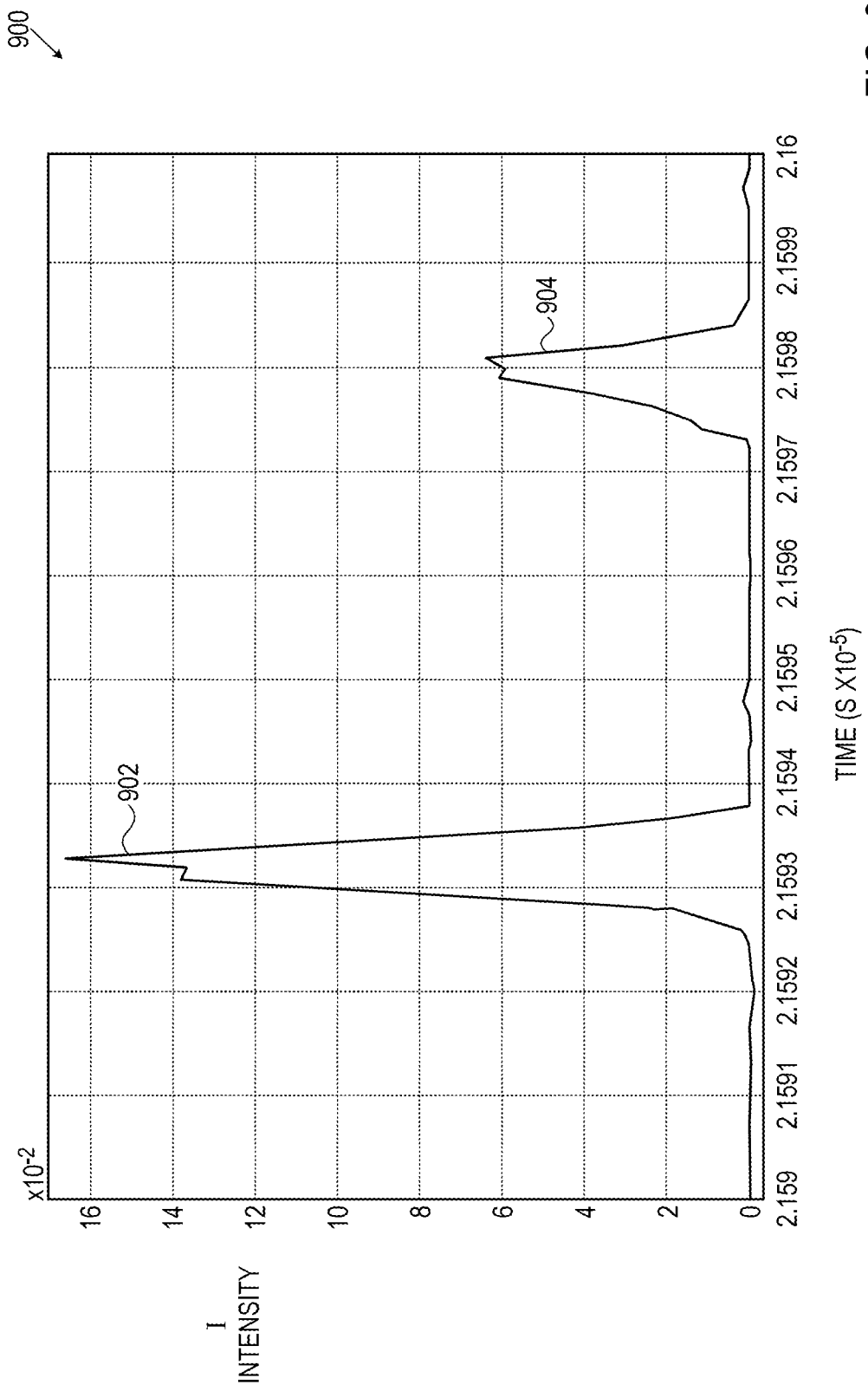
Figure 10:
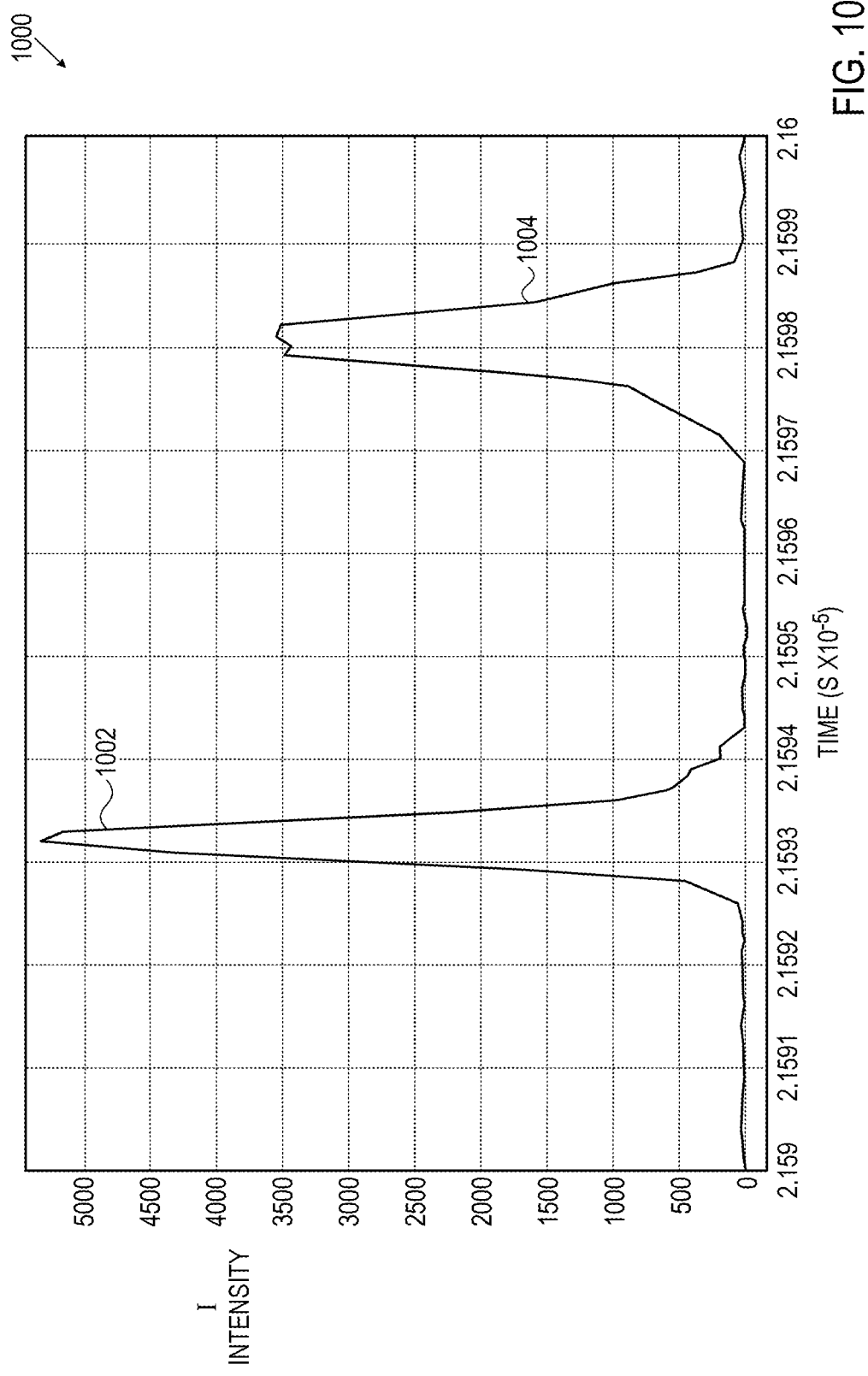
Figure 11:
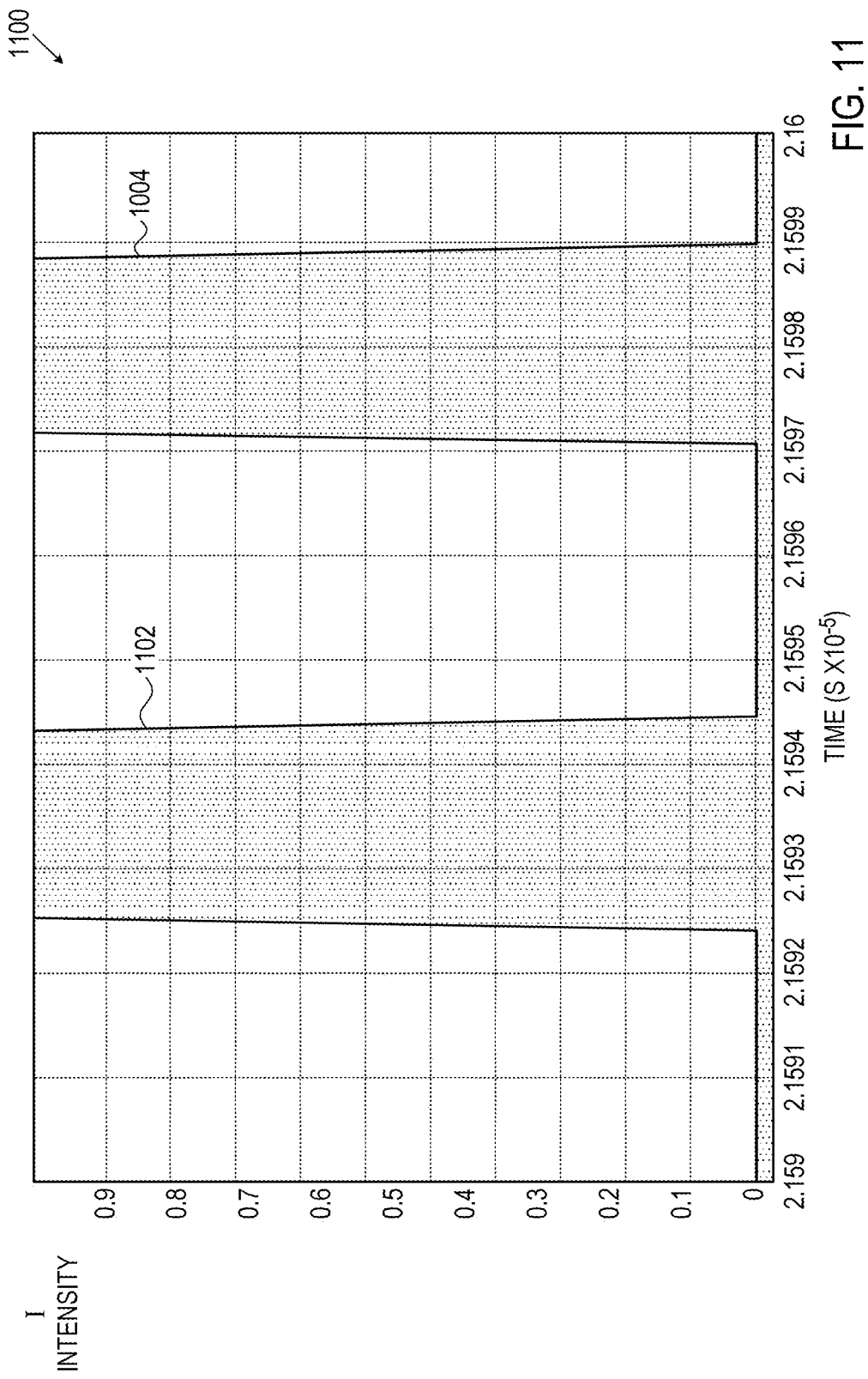
Figure 12:
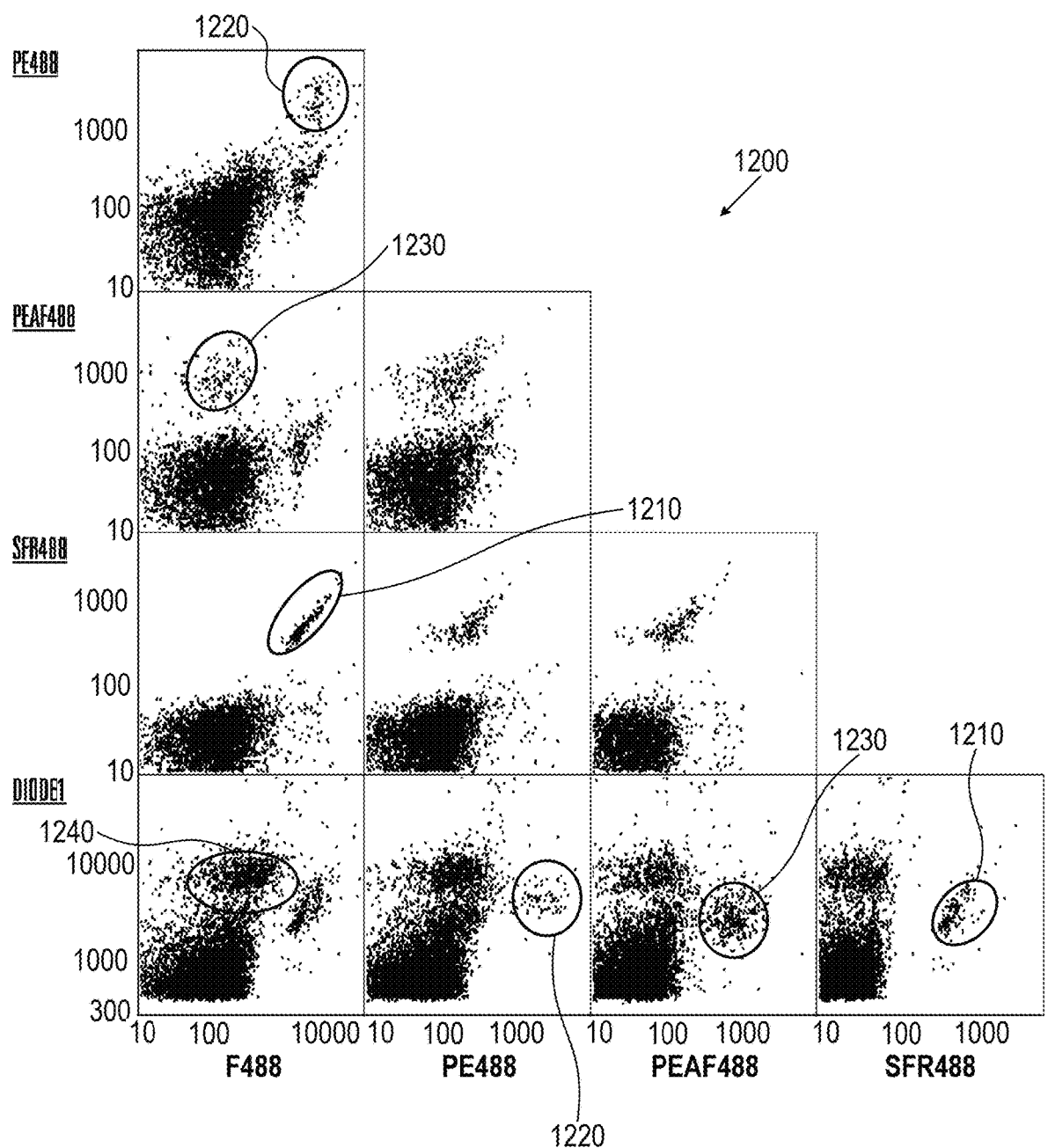
Figure 13A:
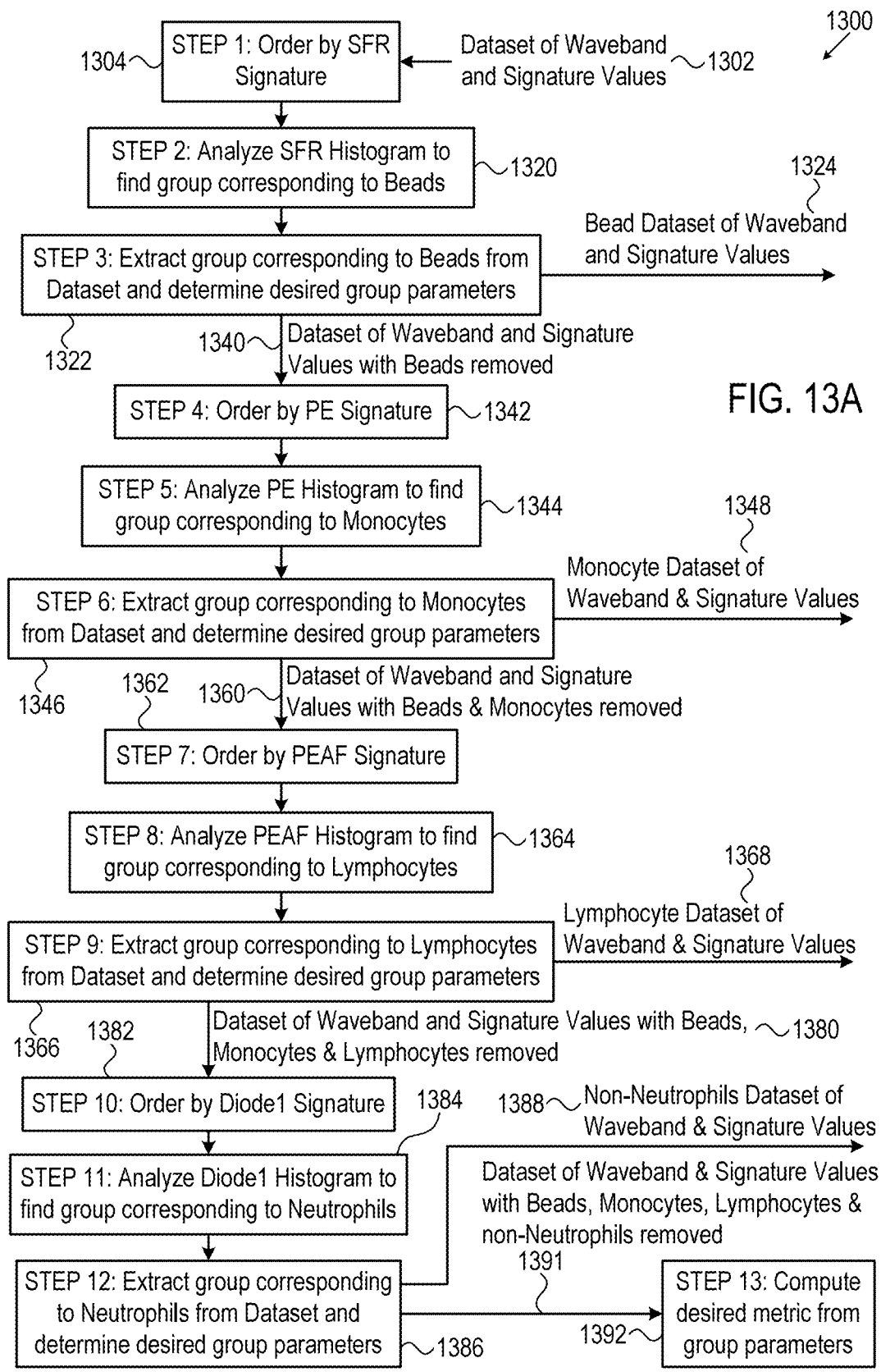
Figure 13B:
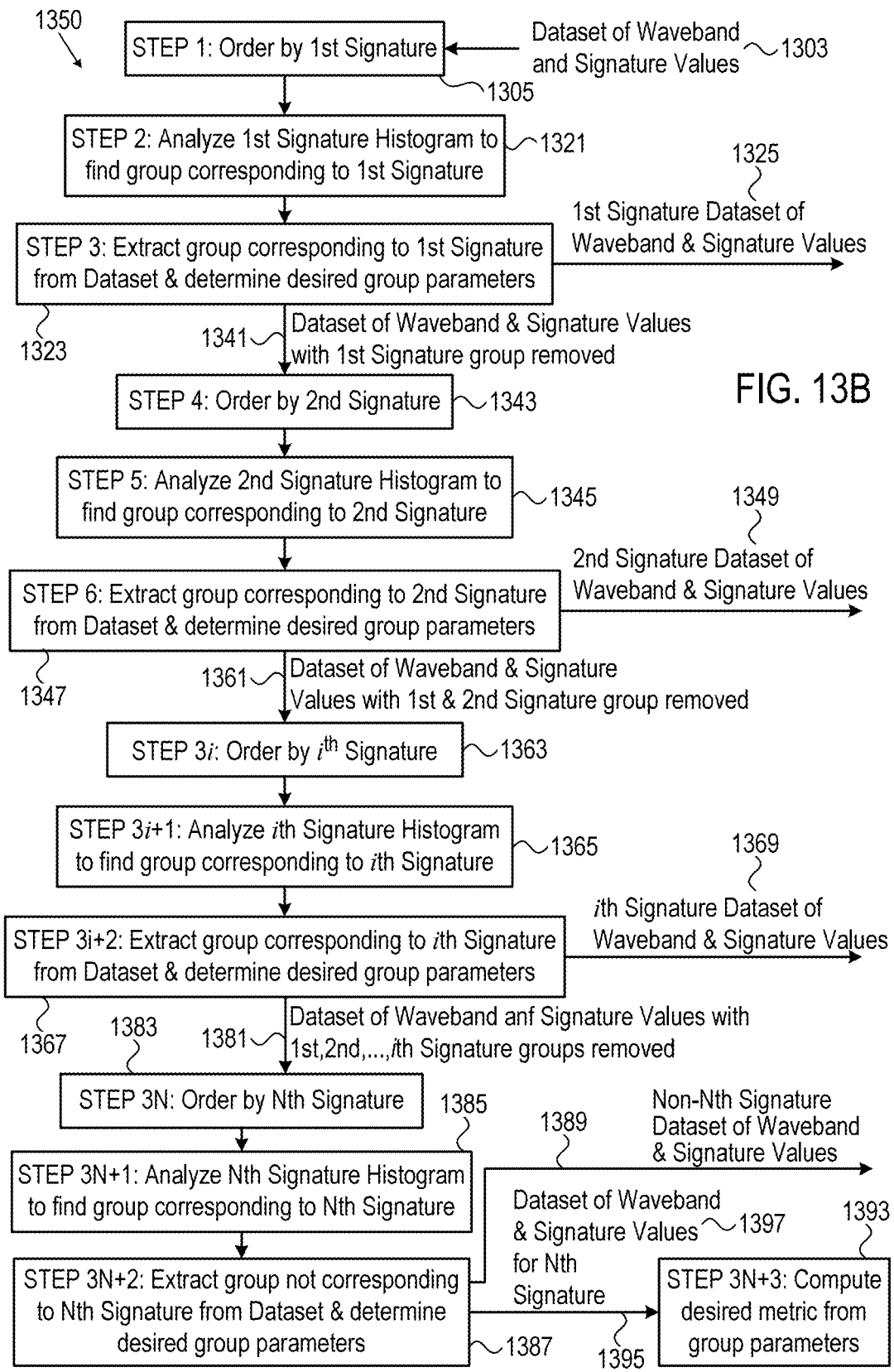
Figure 14A:
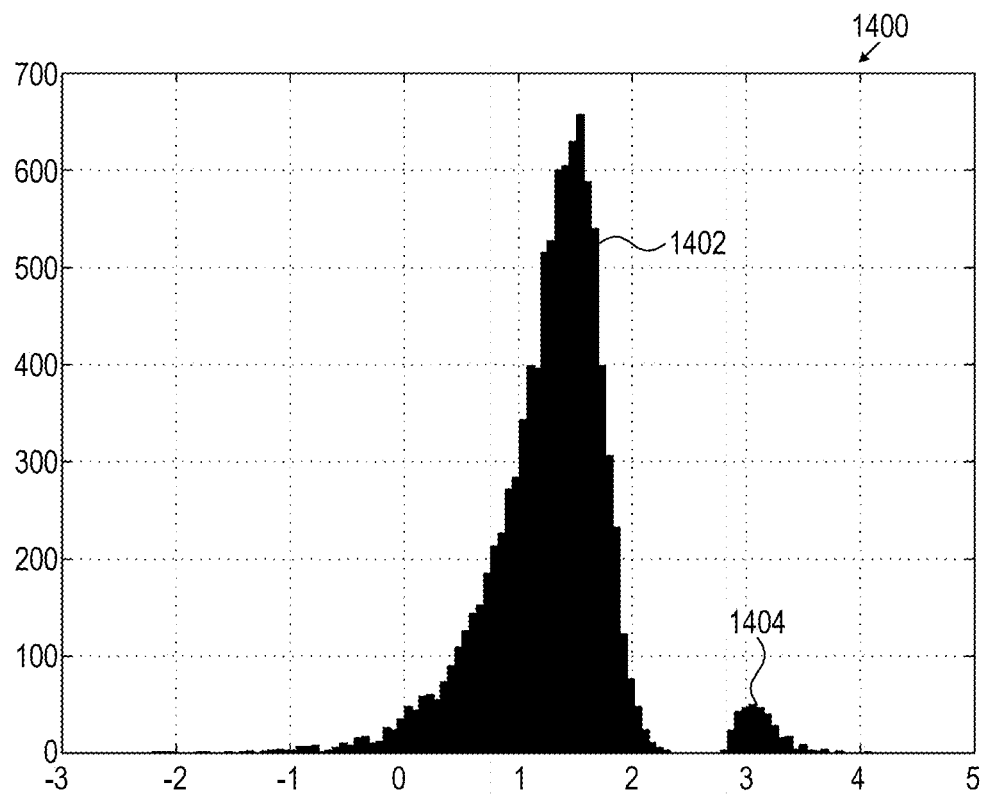
Figure 14B:
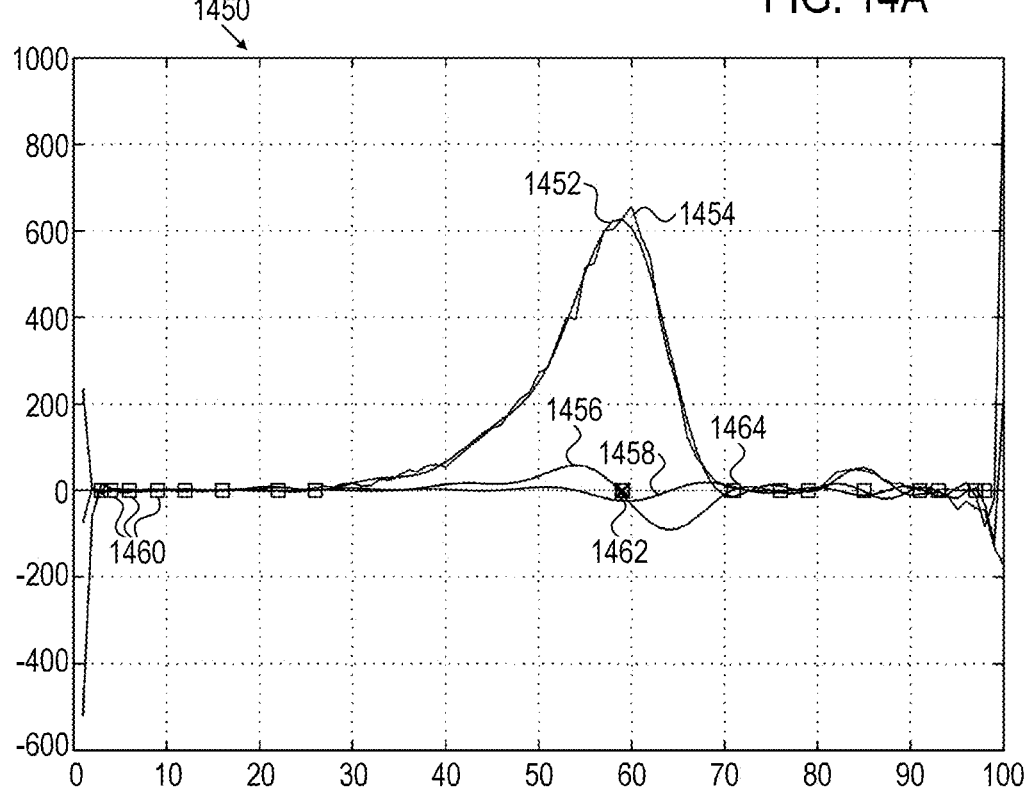
Figure 15A:
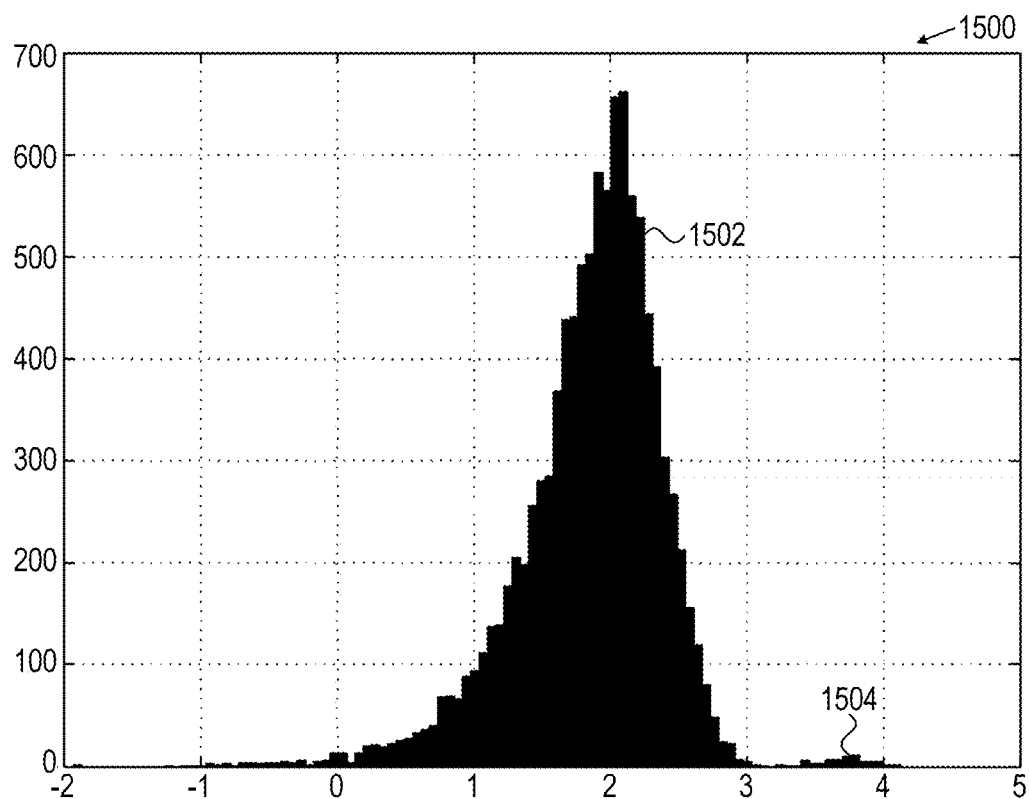
Figure 15B:
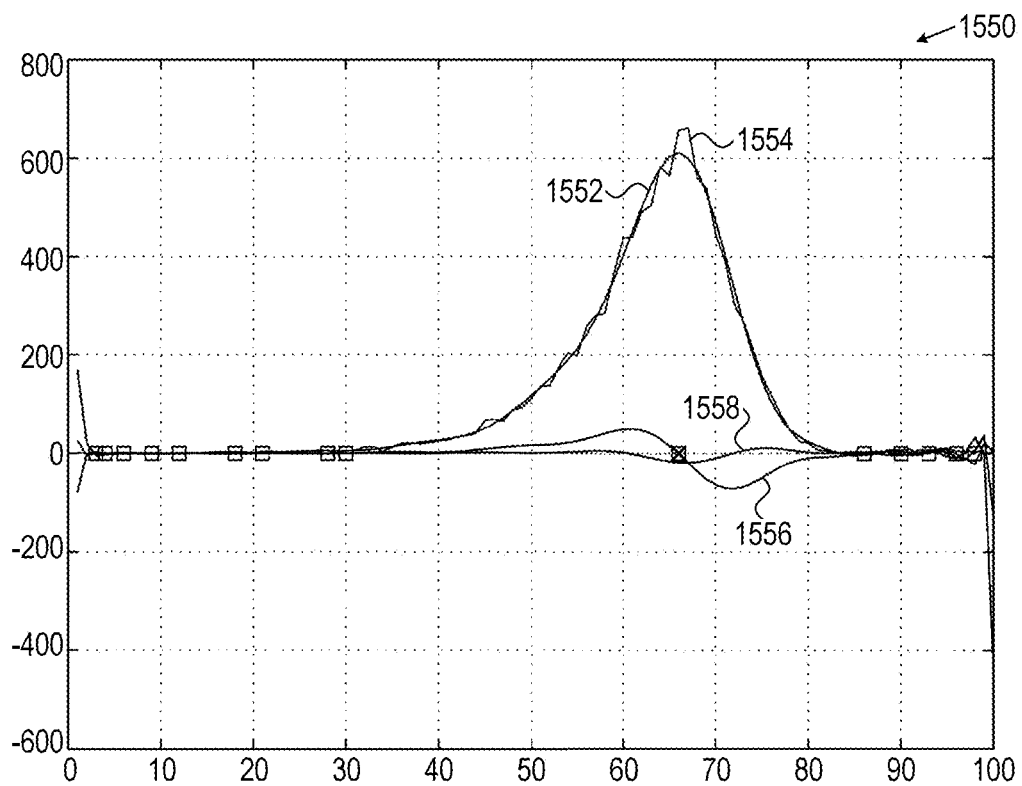
Figure 16A:
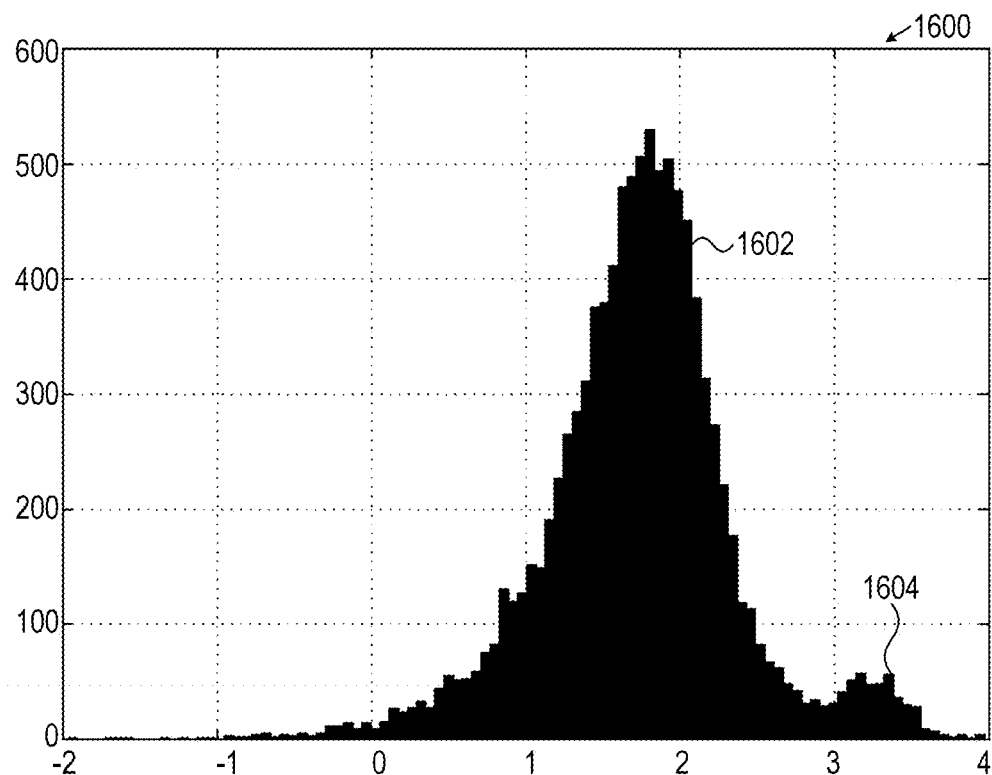
Figure 16B:
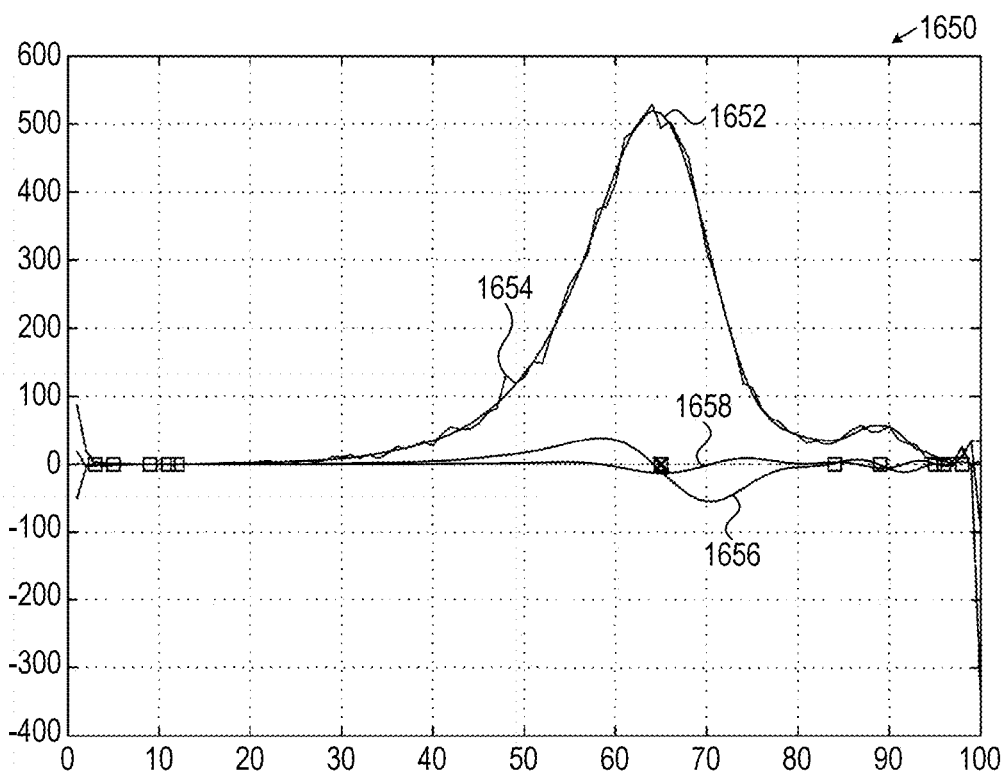

FIG. 10 is a graphical output of data from FIG. 7 after a third mathematical manipulation, in accordance with an embodiment of the present invention;

FIG. 11 is a graphical output of an event locator, based on data from FIG. 8-10, in accordance with an embodiment of the present invention;

FIG. 12 is a scatterplot matrix of the four fluors signatures showing four distinct event groups, in accordance with an embodiment of the present invention;

FIG. 13A is a flowchart of a specific implementation of an algorithm for selecting groups of data from a scatterplot, in accordance with an embodiment of the present invention;

FIG. 13B is a flowchart of a general implementation of an algorithm for selecting groups of data from a scatterplot, in accordance with an embodiment of the present invention;

FIG. 14A is a histogram of data of Starfire Red (SFR) signature values, in accordance with an embodiment of the present invention;

FIG. 14B is a plot of a polynomial and first and second derivative thereof of the histogram shown in FIG. 14A, in accordance with an embodiment of the present invention;

FIG. 15A is a histogram of data of PE488 signature values, in accordance with an embodiment of the present invention;

FIG. 15B shows a polynomial fitted to the histogram in FIG. 15A as well as corresponding first and second derivatives, in accordance with an embodiment of the present invention;

FIG. 16A is a histogram of data of PEAF488 signature values, in accordance with an embodiment of the present invention;

FIG. 16B shows a polynomial fitted to the histogram in FIG. 16A as well as corresponding first and second derivatives, in accordance with an embodiment of the present invention.

Figure 17A:
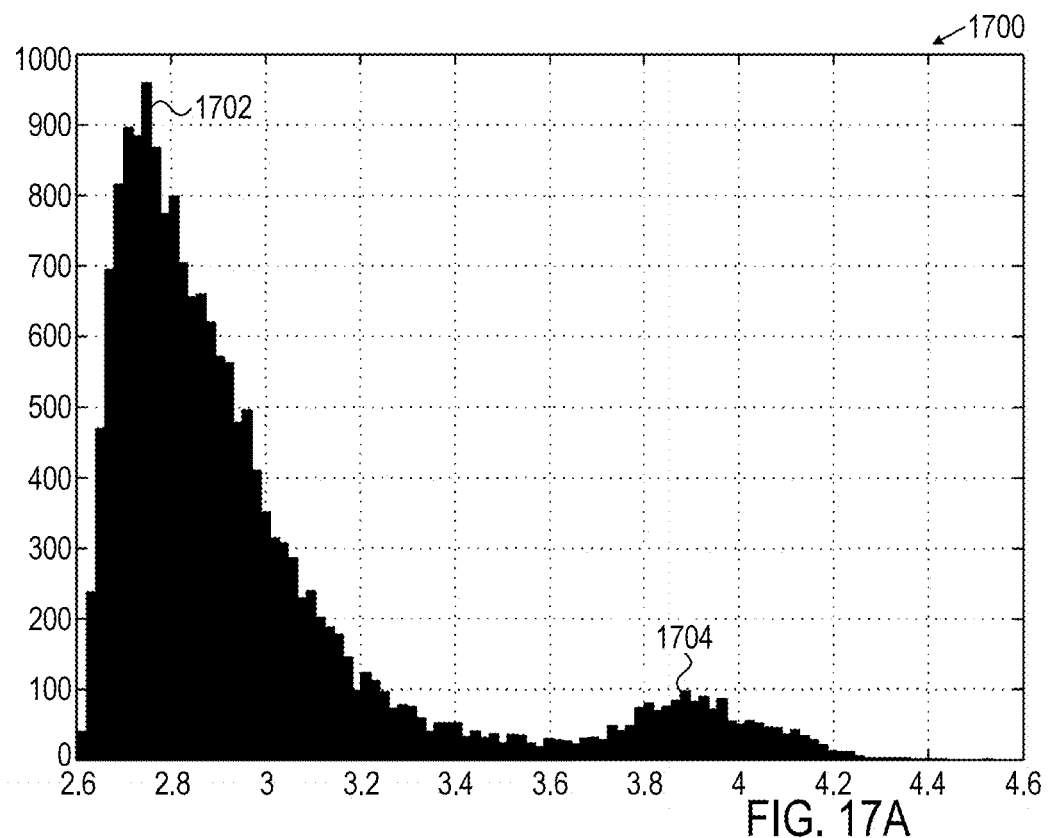
Figure 17B:
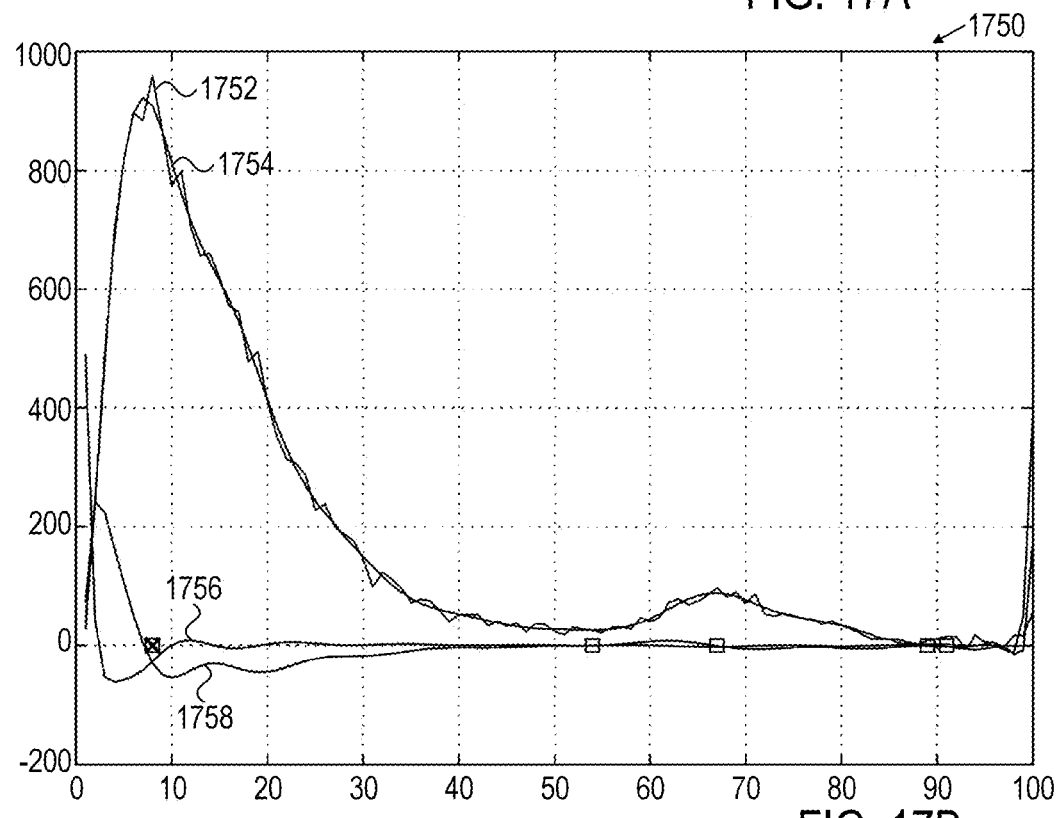
Figure 18A:
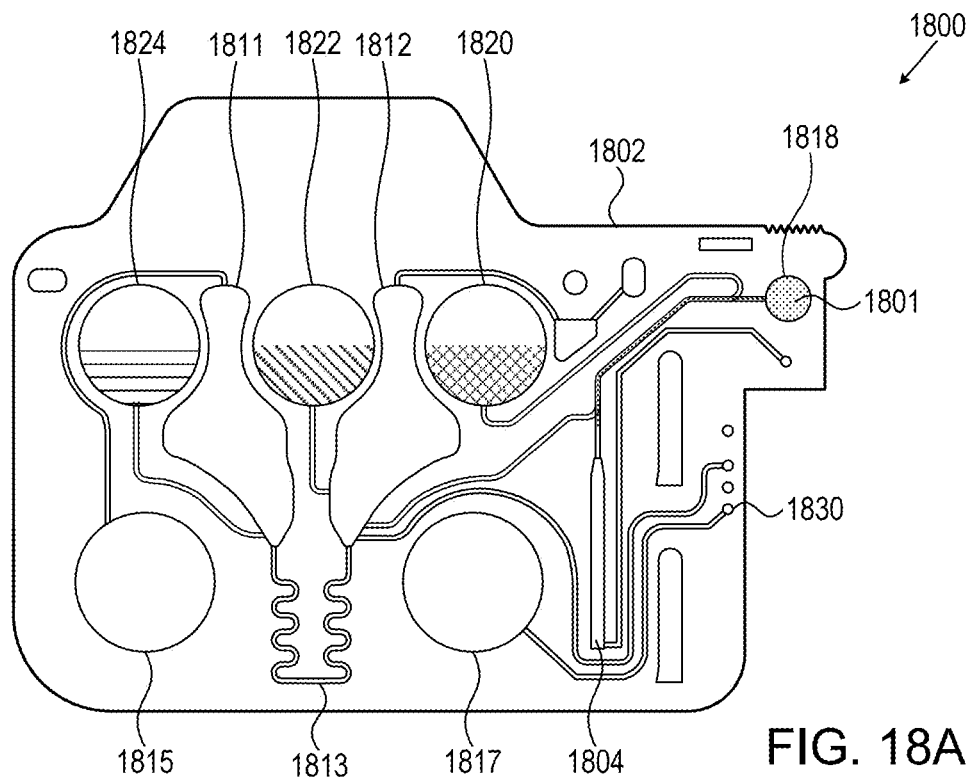
Figure 18B:
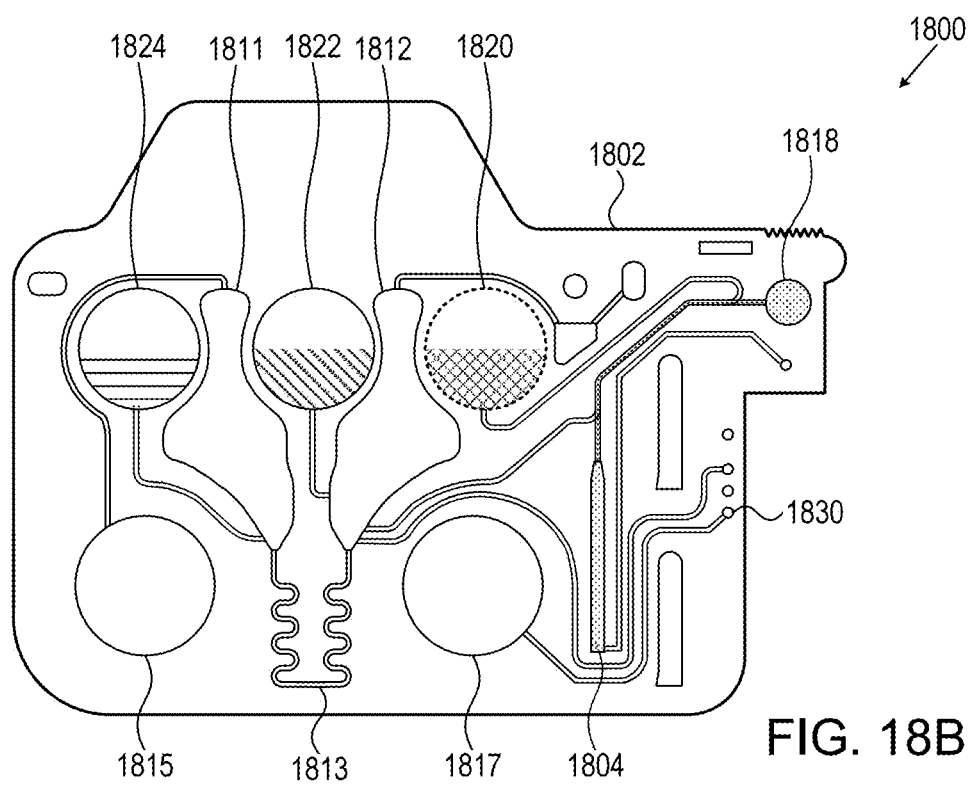
Figure 18C:
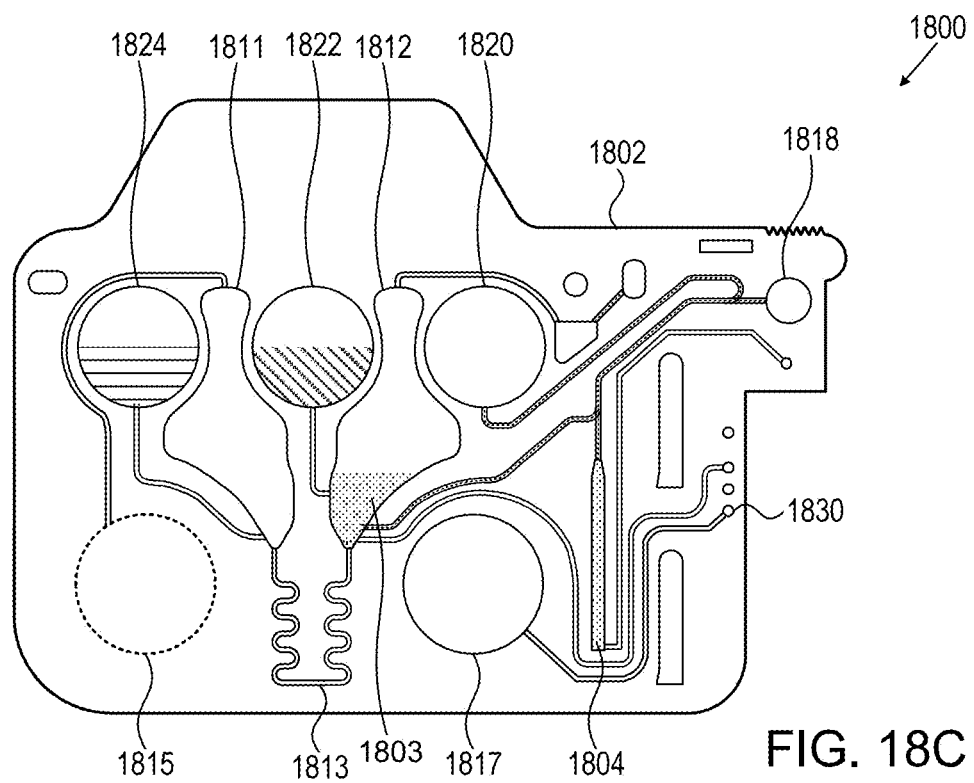
Figure 18D:
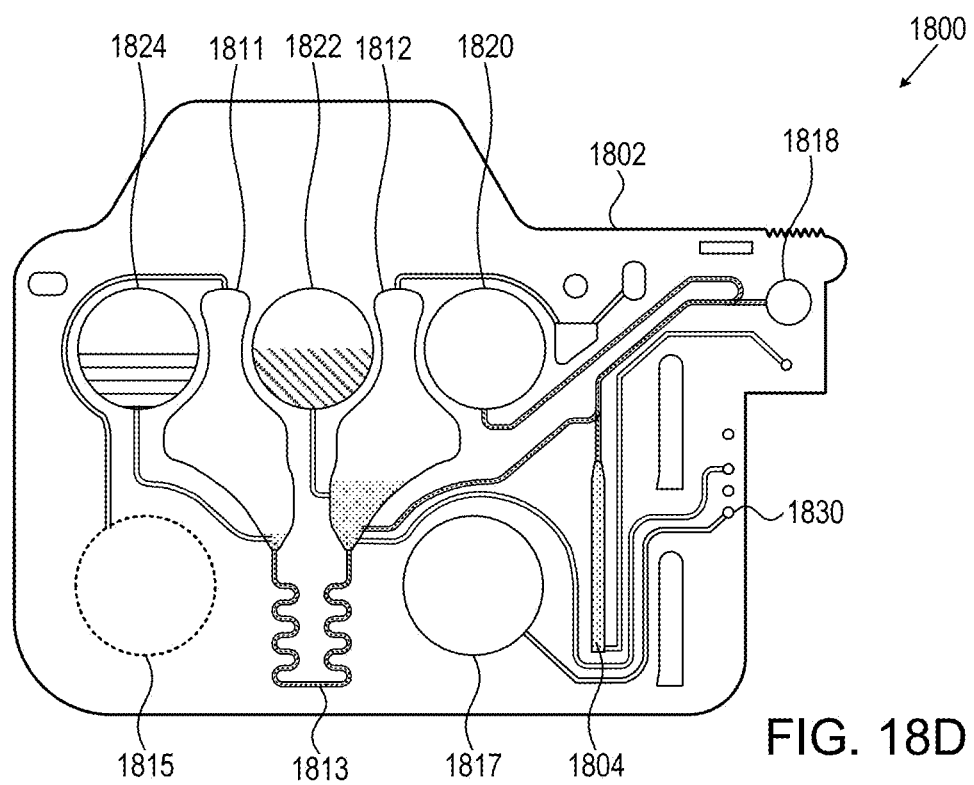
Figure 18E:
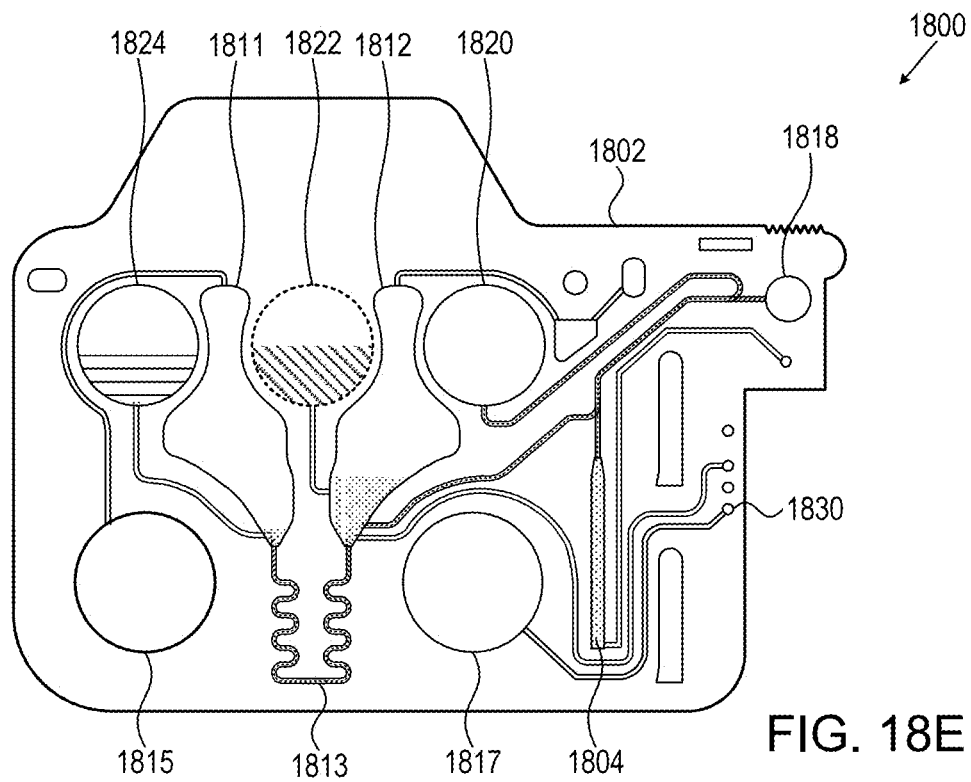
Figure 18F:
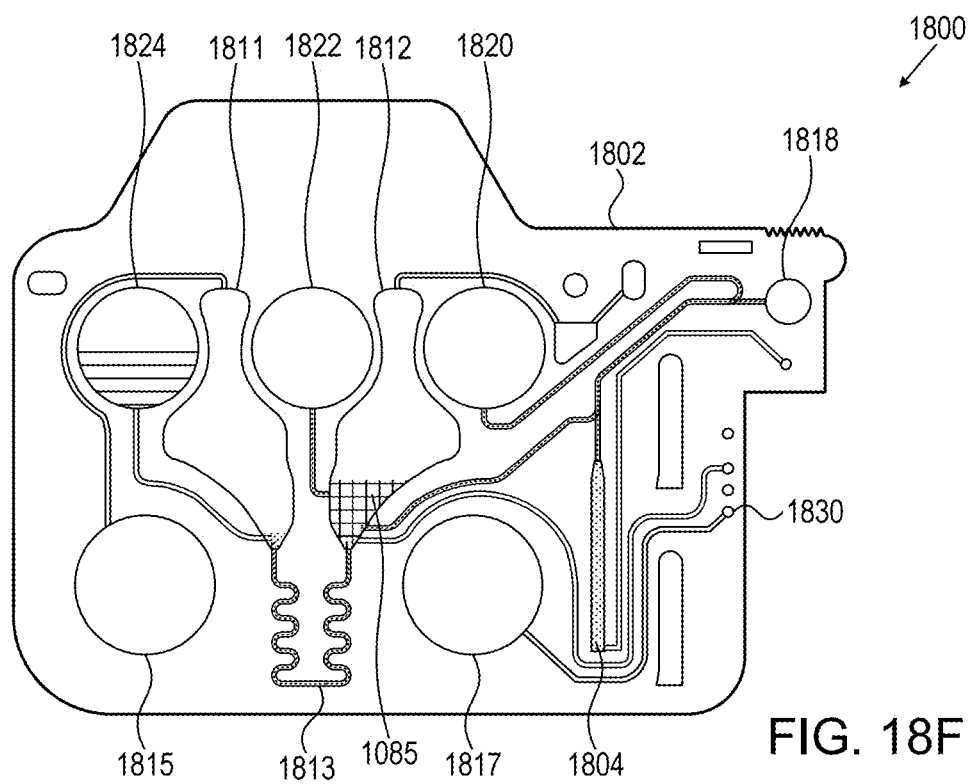
Figure 18G:
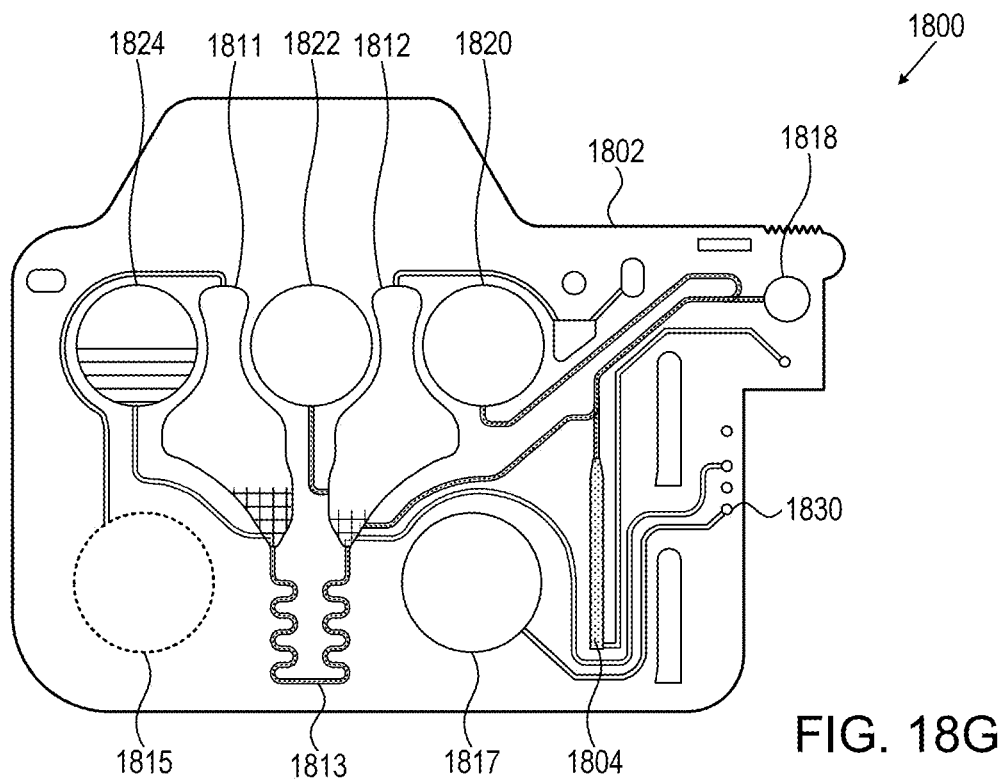
Figure 18H:
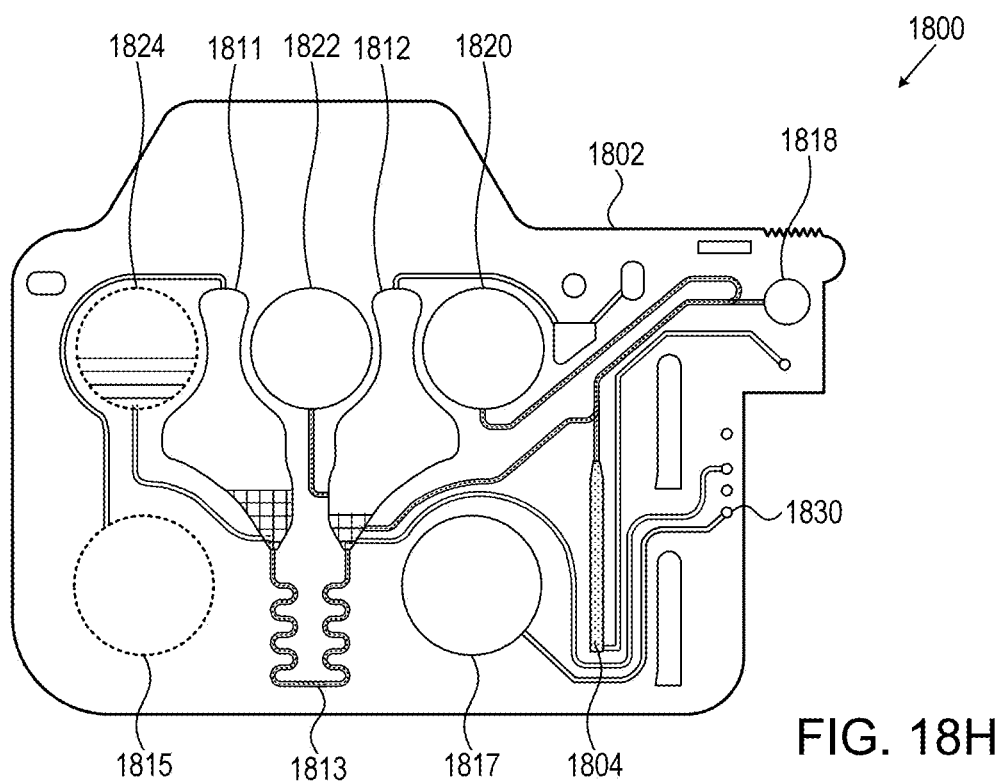
Figure 18I:
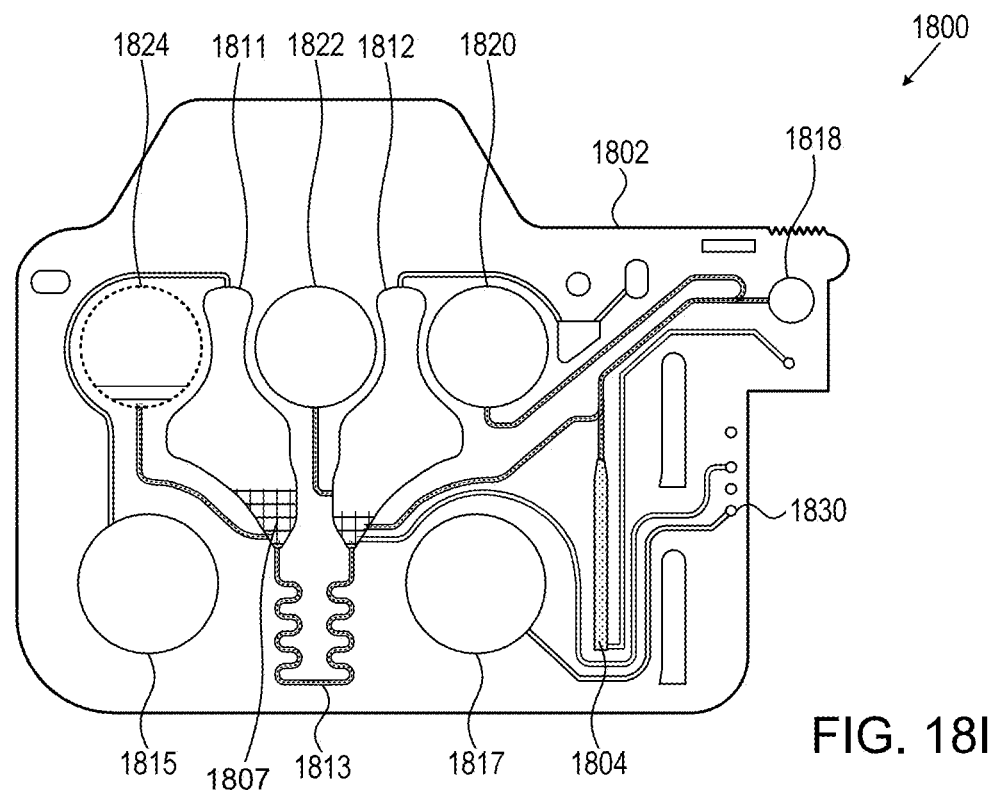
Figure 18J:
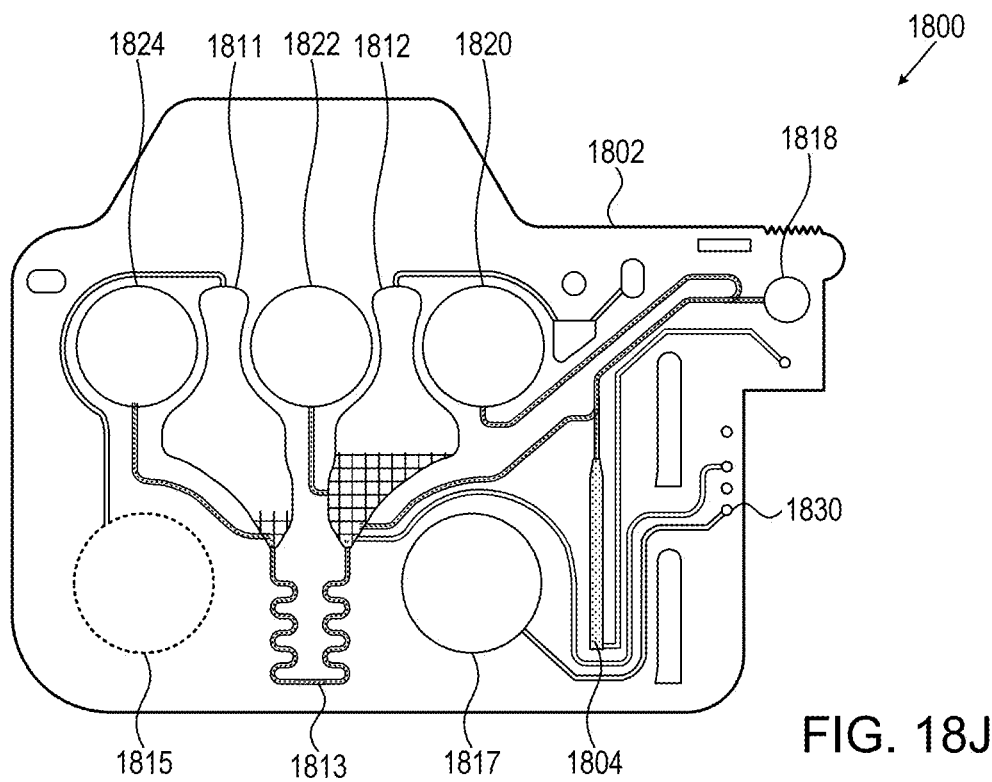
Figure 18K:
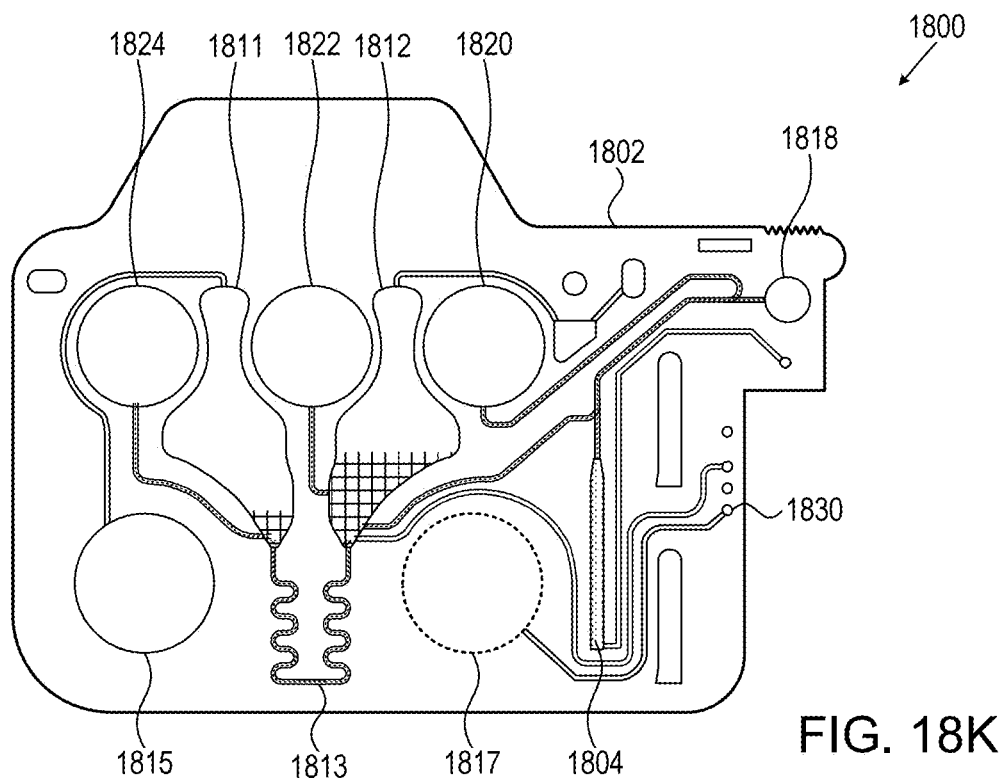
Figure 18L:
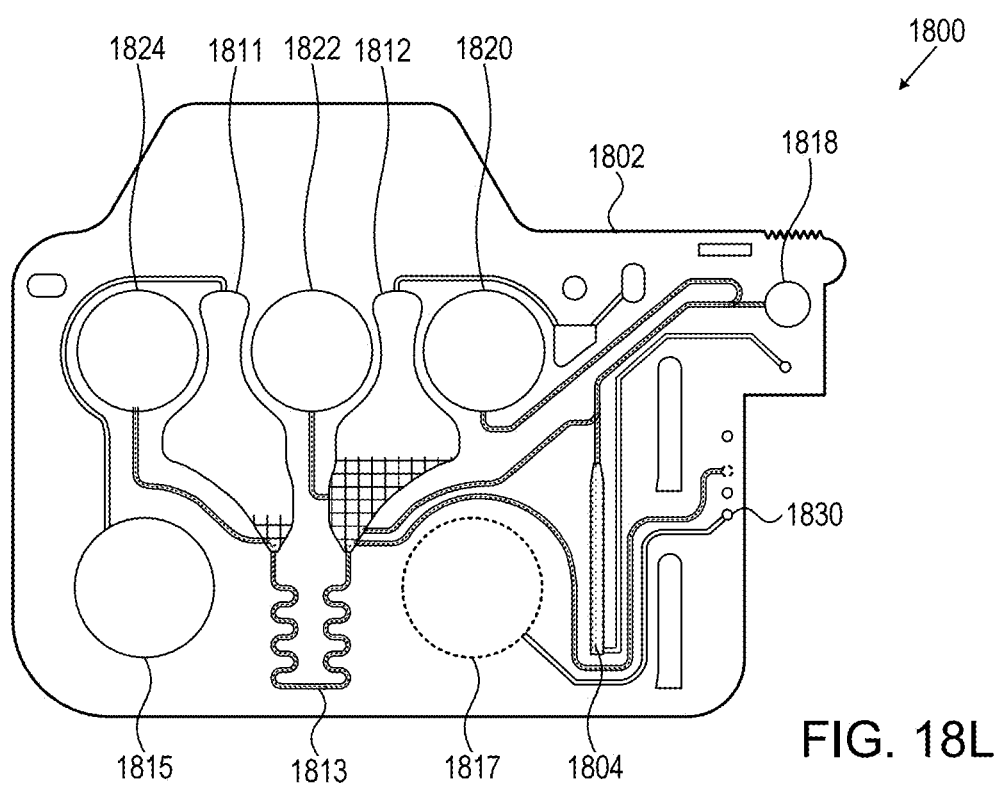
Figure 18M:
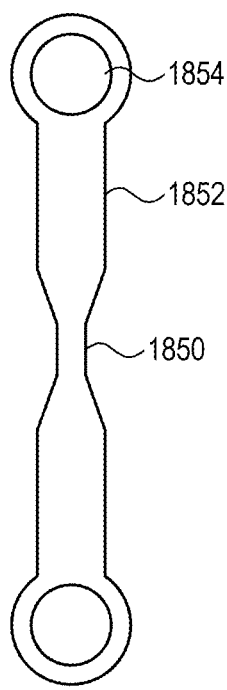
Figure 18N:
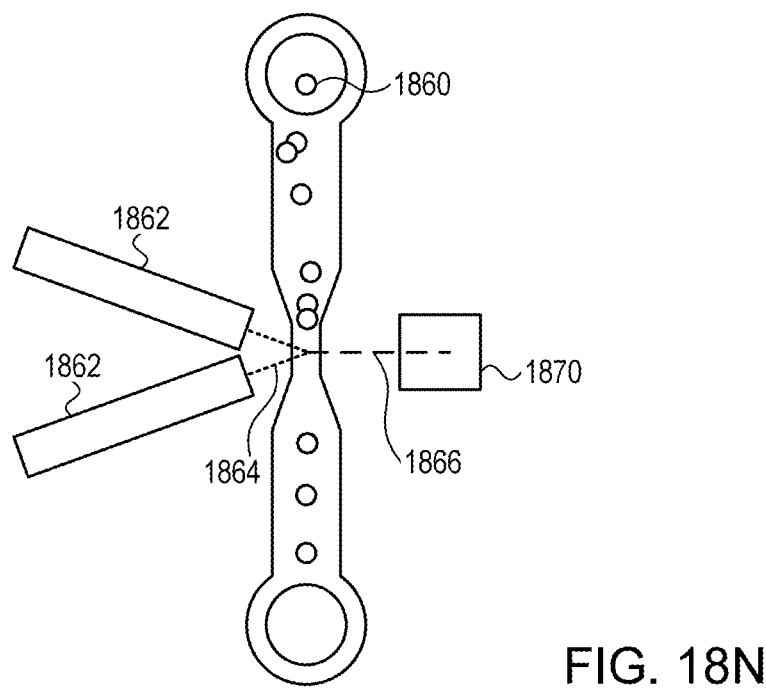
Figure 19:
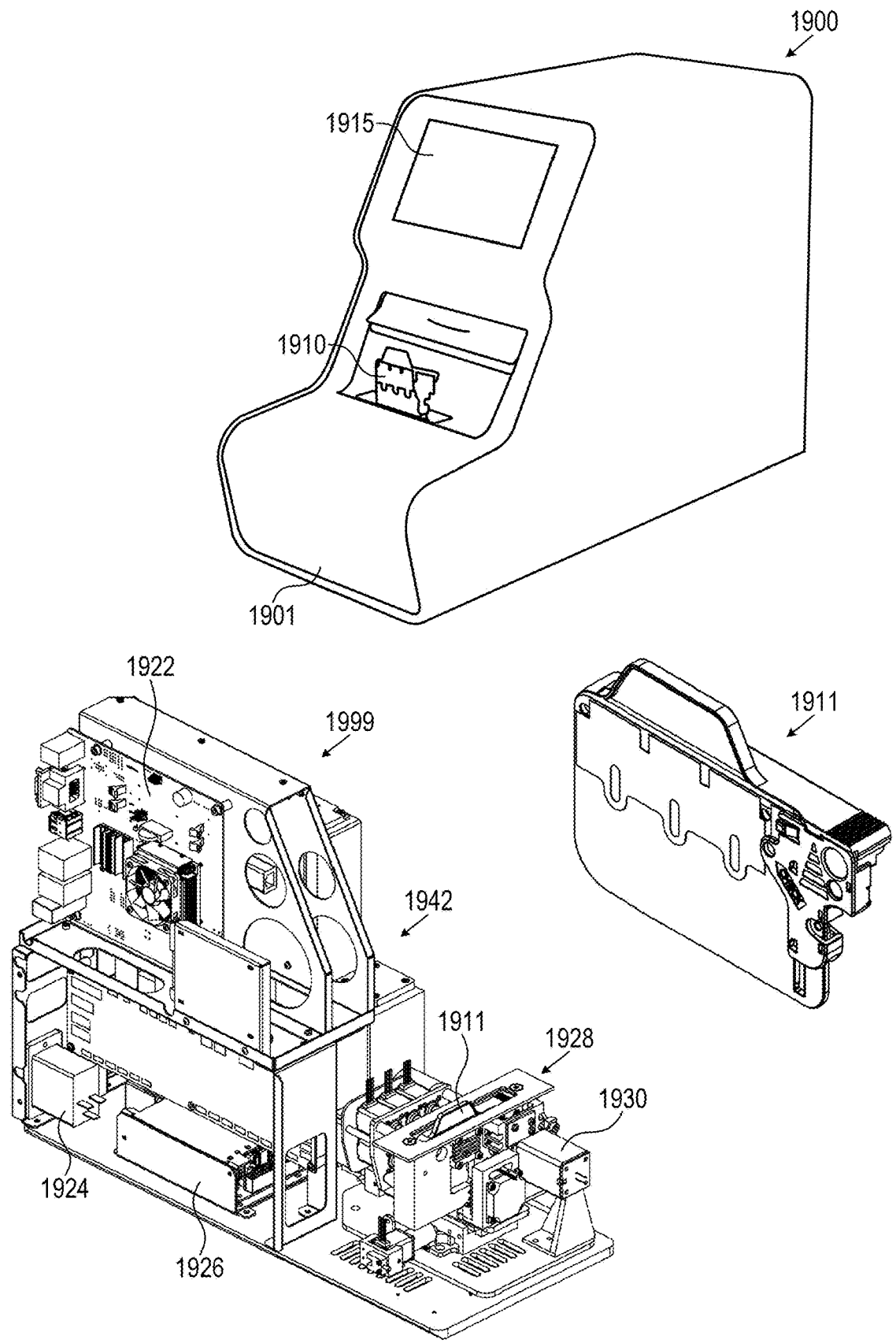

FIG. 17A is a histogram of data of Diode 1 channel signature values, in accordance with an embodiment of the present invention;

FIG. 17B shows the polynomial fitted to the histogram in FIG. 17A as well as the corresponding first and second derivatives, in accordance with an embodiment of the present invention;

FIG. 18A-18N is a sequential set of schematic drawings of the operation of an apparatus (FIG. 1) for detecting a biological condition, in accordance with an embodiment of the present invention; and FIG. 19 is a simplified three dimensional front view of a system, comprising a reader assembly and a cartridge, for detecting a biological condition, in accordance with an embodiment of the present invention.

In all the figures similar reference numerals identify similar parts.

DETAILED DESCRIPTION OF THE INVENTION

In the detailed description, numerous specific details are set forth in order to provide a thorough understanding of the invention. However, it will be understood by those skilled in the art that these are specific embodiments and that the present invention may be practiced also in different ways that embody the characterizing features of the invention as described and claimed herein.

International patent application publication no. WO2011/128893 to Kasdan et al., describes a device, system and method for rapid determination of a medical condition and is incorporated herein by reference.

The microfluidic cartridges of the present invention may be any suitable cartridge as shown in the figures or any of the prior art cartridges described or cited herein, such as, but not limited to, those described in U.S. Pat. No. D669,191 S1, US20120266986 A1, EP1846159 A2, US2012275972, WO11094577A, US2007292941A and EP1263533 B1.

Figure 1:
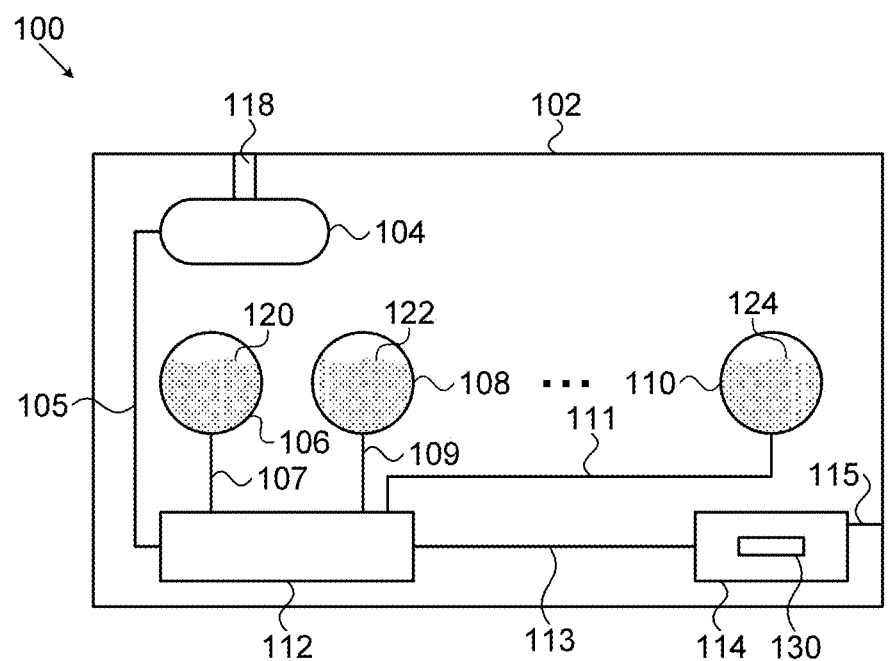

Reference is now made to FIG. 1, which is a simplified schematic illustration of an apparatus 100, which comprises a cartridge 102 for detecting a biological condition, in accordance with an embodiment of the present invention.

Apparatus 100 comprises cartridge 102 and a number of chemical/biochemical reactants termed herein, treatment compositions 120, 122, 124. The treatment compositions are adapted to react, at least in part, with biological specimen, such as a body specimen, to be introduced to the apparatus. The body specimen may be a bodily fluid such as, but not limited to, blood, serum, plasma, urine, saliva, cerebrospinal fluid (CSF), serous fluid, peritoneal fluid and synovial fluid. Additionally or alternatively, the body specimen may be a solid such as a hair, a tooth part, a bone part or a piece of cartilage.

Apparatus 100 comprises a specimen receiving element 118, adapted to transfer the specimen to a sample composition chamber 104. The sample composition chamber comprises one or more transfer elements 105, adapted to transfer the specimen from the sample composition chamber to one or more other locations in the cartridge. In the non-limiting example shown in FIG. 1, transfer element 105 is a conduit in fluid connection with a treatment chamber 112.

Additionally, the cartridge comprises a number of treatment composition chambers 106, 108, 110, adapted to respectively house a corresponding number of treatment compositions 120, 122, 124. These treatment compositions may be liquid, solid or combinations thereof. Apparatus 100 is typically sold commercially as a system with the treatment compositions disposed therein. In some cases, the apparatus 100 may be adapted for a one-off test and may be disposable. In other cases, the apparatus may be re-used. A re-usable apparatus may be adapted to receive additional external compositions (not shown) or may have a plurality of treatment compositions, wherein only a portion is used for each test.

The apparatus may be constructed and configured such that the treatment composition comprises proteins attached to a surface, such as to beads. A plurality of beads or other structural elements with proteins attached to their surfaces can be made by any one or more of the following methodologies:—

- simple attachment such as by adsorption via electrostatic or hydrophobic interactions with the surface, entrapment in immobilized polymers, etc.
- non-covalent or physical attachment;
- covalent bonding of the protein to the bead surface biological recognition (e.g., biotin/streptavidin).
- requires two steps: a first layer is formed by silane chemistry such that the surface presents a reactive group (for example epoxy, amino, thiol, etc.), and a second layer (e.g., the protein to be immobilized or a linker molecule) is covalently attached via the immobilized reactive groups.

covalent attachment to functionalized polymer coatings on the interior of the device or linkage to the free end of a self-assembled monolayer (SAM) on a gold surface.

The reaction type may include any one or more of antigen-antibody binding, sandwich (such as antibody-antigen-antibody), physical entrapment, receptor-ligand, enzyme-substrate, protein-protein, aptamers, covalent bonding or biorecognition.

Cartridge 102 further comprises at least one transfer element 107, 109, 111 in fluid communication with each respective of treatment composition chamber, each transfer element also being in fluid communication with treatment chamber 112. These elements are typically microfluidic channels and may be designed for mixing, such as being tortuous in shape.

Various methodologies for transferring the contents of the treatment composition chambers and the sample composition chamber via the transfer elements to the treatment chamber may be employed, some of which are known in microfluidics technologies. These include air blowing, suction, vacuuming, mechanical transfer, pumping and the like.

Cartridge 102 further comprises at least one transfer element 113 in fluid communication with treatment chamber 112 and with an evaluation chamber 114.

Optionally, evaluation chamber 114 is further in fluid communication with a transfer element 115, adapted to remove the contents of the evaluation chamber for disposal outside the cartridge. Alternatively, the evaluation chamber may have no external disposal means.

Table 1 shows some representative applications of apparatus 100 and methods of the present invention.

TABLE 1

Applications of the apparatus and methods of this invention.

| Application | Type of Test | Relevant Figures in this invention | Typical Prior Art Laboratory Turnaround time (TAT)- see references | This invention Turn-around time (TAT) | References |
|---|---|---|---|---|---|
| Application #1 - CD64 Infection & Sepsis | Surface Marker | FIGS. 1-2 and 3-5D | 4 hours | 10 minutes | U.S. Pat. No. 8,116,984, Davis, BH et al., (2006) |
| 1 - Fetal Hemoglobin Test | Plasma Protein | FIGS. 1-2 and 6-8D | 4 hours | 10 minutes | Dziegiel et al. (2006) |
| 2 - Low Platelet Count | Surface Marker | FIGS. 1-2 and 3-5D | 4 hours | 10 minutes | Segal, H. C., et al. (2005): |
| 3 - Resolving BLAST Flag for hematology Lab | Surface Marker | FIGS. 1-2 and 3-5D | 4 hours | 10 minutes | Guerti, K., et al. |
| 4 - CD34 Stem Cell Enumeration Assay | Surface Marker | FIGS. 1-2 and 3-5D | 4 hours | 10 minutes | Sutherland et al. (1996) |
| 5 - Platelets Activation Assay CD62 | Surface Marker | FIGS. 1-2 and 3-5D | 4 hours | 10 minutes | Graff et al. (2002) Divers, S. G., et al. (2003) |
| 6 - D-dimer (Bead based protein) | Plasma Protein | FIGS. 1-2 and 6-8D | 4 hours | 10 minutes | Stein et al. (2004) Rylatt, D. B., et al. (1983): |
| 7 - Chorioamnioitis CD64 | Surface Marker | FIGS. 1-2 and 3-5D | 4 hours | 10 minutes | Hillier et al. (1988) |
| 8 - CD20 Cell Quantitation (Therapy Monitoring) | Surface Marker | FIGS. 1-2 and 3-5D | 4 hours | 10 minutes | Rawstron et al. (2001) Cheson et al. (1996) |
| 9 - CD52 Cell quantitation (Therapy Monitoring) | Surface Marker | FIGS. 1-2 and 3-5D | 4 hours | 10 minutes | Rawstron et al. (2001) |
| 10 - Circulating Tumor Cells | Surface Marker | FIGS. 1-2 and 3-5D | 4 hours | 10 minutes | Cristofanilli et al. (2004 |
| 11 - Reticulated Platelet Assay | Surface Marker | FIGS. 1-2 and 3-5D | 4 hours | 10 minutes | Matic et al. (1998) Ault et al (1993) Wang et al. (2002) |
| 12 - Bacteria Detection in platelet packs | | | 4 hours | 10 minutes | Blajchman et al (2005) McDonald et al. (2005) |
| 13 - Platelet Associated Antibodies | Surface Marker | FIGS. 1-2 and 3-5D | 4 hours | 10 minutes | Michelson (1996) |
| 14 - Residual Leukocyte Count in blood products | Surface Marker | FIGS. 1-2 and 3-5D | 4 hours | 10 minutes | Bodensteiner, (2003) |
| 15 - CD4 HIV AIDS | Surface Marker | FIGS. 1-2 and 3-SD | 4 hours | 10 minutes | Rodriguez (2005). Dieye et al. (2005) |

TABLE 1-continued

Applications of the apparatus and methods of this invention.

| Application | Type of Test | Relevant Figures in this invention | Typical Prior Art Laboratory Turnaround time (TAT)- see references | This invention Turn-around time (TAT) | References |
|---|---|---|---|---|---|
| 16 - Leukemia Panels - Very complex | Surface Marker | FIGS. 1-2 and 3-5D | 4 hours | 10 minutes | Drexler et al (1986) |
| 17 - Bladder Cancer Screening in Urine - Urine sample | Surface Marker | FIGS. 1-2 and 3-5D | 4 hours | 10 minutes | Ramakumar et al (1999) Lotan et al. (2009) |
| 18 - HLA DR Sepsis and Immunosuppression | Surface Marker | FIGS. 1-2 and 3-5D | 4 hours | 10 minutes | Hershman et al. (2005) Perry et al (2003) |
| 19 - RECAF Protein for Canine and other Cancers | Plasma Protein | FIGS. 1-2 and 6-8D | 4 hours | 10 minutes | Moro et al. (2005). |
| 20 - CytoImmun - Cervical Screening | | | 4 hours | 10 minutes | Hilfrich et al. (2008) |
| 21 - Procalcitonin (Bead Based Protein) + Feasibility | Plasma Protein | FIGS. 1-2 and 6-8D | 4 hours | 10 minutes | Assicot et al. (1993) Christ-Crain et al. (2004) |

Figure 2:
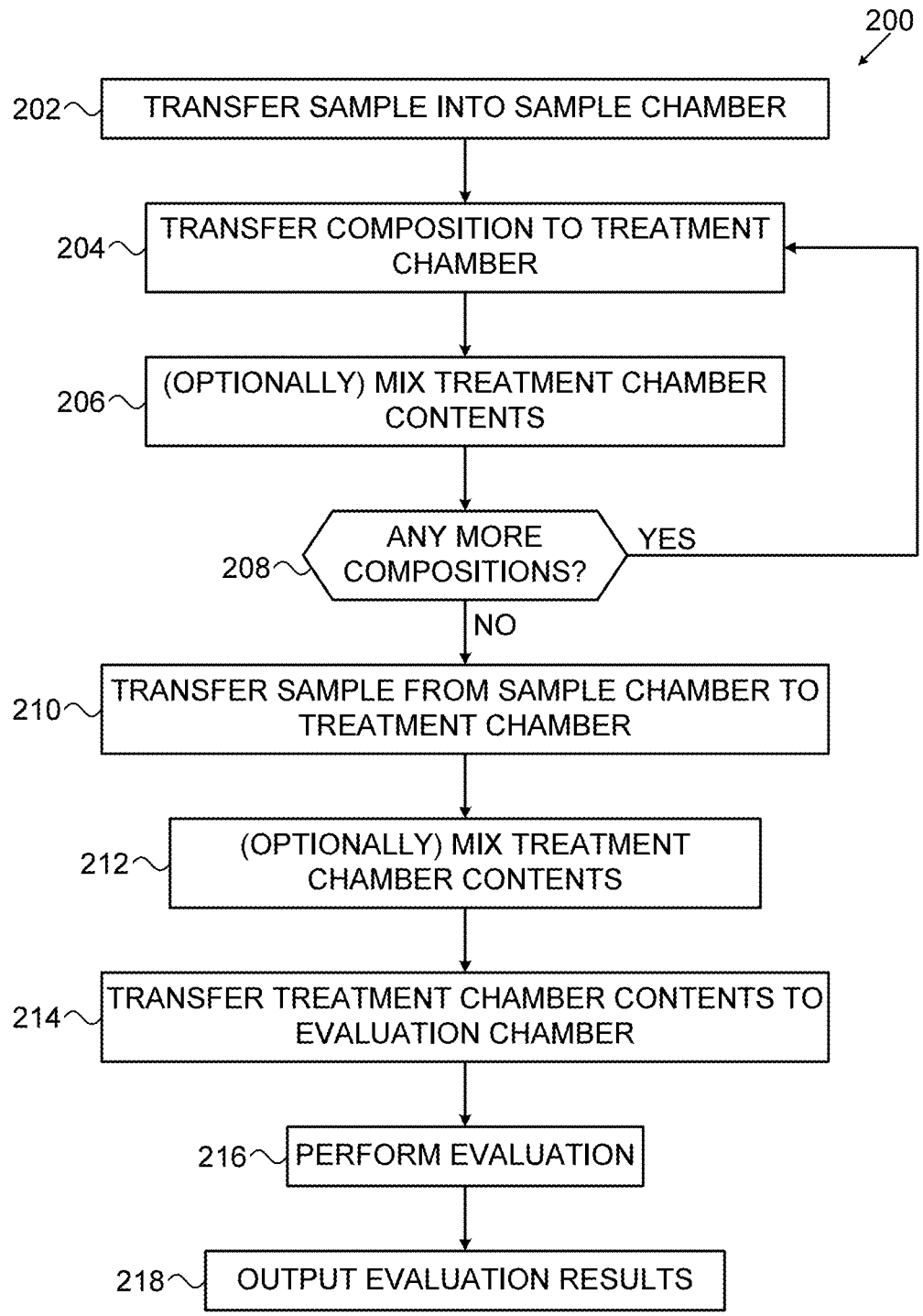

Reference is now made to FIG. 2, which is a simplified flow chart 200 of a method for detecting a biological condition, in accordance with an embodiment of the present invention.

It should be understood that each of the steps of the method may take a predetermined period of time to perform, and in between these steps there may be incubation and/or waiting steps, which are not shown for the sake of simplicity.

In a sample transferring step 202, a sample, such as a bodily specimen is transferred from outside apparatus 100 via receiving element 118 into sample composition chamber 104 and then to the treatment chamber 112. According to some embodiments, the volume of the specimen or sample is less than 200 µL, less than 100 µL, less than 50 µL, less than 25 µL or less than 11 µL.

Thereafter, treatment composition 120 is transferred via transfer element 107 to the treatment chamber in a composition transfer step 204. In some cases, there may be a treatment composition disposed in the treatment chamber.

Depending on the nature of the treatment composition and sample/specimen type, there may be a requirement to mix or agitate the treatment chamber contents in an optional mixing step 206. This may be performed by using a small stirbar (not shown) disposed in the chamber. Additionally or alternatively, this may be effected by the fluid dynamics of system. Additionally or alternatively, stirbars may be disposed in any of the other chambers in the apparatus.

Typically, the total sample volumes are in the range of 10 to 1000 µL, 100 to 900 µL, 200 to 800 µL, 300 to 700 µL, 400 to 600 µL, or 420 to 500 µL.

According to some embodiments, the volume of the treatment composition chambers 106, 108, 110 (also called blisters) is from about 1 µL to 1000 µL. According to other embodiments, the volume of the specimen is from about 10 µL to 200 µL. According to other embodiments, the volume of the specimen is about 1, 10, 20, 30, 40, 50, 60, 70, 80, 90, 100, 120, 140, 160, 180, 200, 250, 300, 350, 400, 450, or 500 µL.

According to some embodiments, the volume of the treatment compositions 120, 122, 124 is at most about 500 µL. According to other embodiments, the volume of the specimen is at most about 200 µL. According to other embodiments, the volume of the specimen at most about 500, 450, 400, 350, 300, 250, 200, 180, 160, 140, 120, 100, 90, 80, 70, 60, 50, 40, 30, 20, 10, or 1 µL.

According to some embodiments, the volume of a reactant is at least about 1 µL. According to other embodiments, the volume of the specimen is from about 10 µL. According to other embodiments, the volume of the specimen is at least about 1, 10, 20, 30, 40, 50, 60, 70, 80, 90, 100, 120, 140, 160, 180, 200, 250, 300, 350, 400, 450, or 500 µL.

The sequence of transfer of the various treatment compositions may be important to the reaction sequence and is typically predefined. Steps 204-206 may be performed, for example on treatment composition chamber 106, thereafter on treatment composition chamber 108 and thereafter on treatment composition chamber 110. In some cases, some of these steps may be performed concurrently.

In a checking step 208, it is ascertained whether all the compositions required for the sample treatment have been transferred to the treatment chamber. If any compositions remain, then steps 204-206 are performed on the subsequent treatment composition chamber(s). If no further treatment compositions require transfer, then the sample/specimen is transferred from chamber 104 into the treatment chamber.

Thereafter, in a second sample transfer step 210, the sample is transferred from the sample composition chamber into the treatment chamber.

According to some embodiments, step 210 may be performed before steps 204-208.

If required, an optional mixing step 212 to the contents of the treatment chamber may be performed.

In a transferring step 214, the contents of the treatment chamber are transferred to the evaluation chamber.

The evaluation chamber 114 is configured and constructed for one or more evaluation steps 216. These may include any of the following, or combinations thereof:

a) transfer of radiation there-through,
b) impinging radiation thereupon;
c) detecting reflected, refracted, and/or transmitted radiation,
d) detecting emitted radiation;
e) capturing one or more images thereof;
f) performing image analysis on the captured images;
g) measuring electrical characteristics of the treated specimen;
h) impinging sonic energy thereon;
i) detecting sonic energy therefrom; and
j) analyzing the outputs of any one or more of the above steps.

According to some embodiments, the cartridge is introduced into a system as described in International patent application publication no. WO2011/128893 to Kasdan et al., incorporated herein by reference.

The results of the evaluation step are then outputted in a results outputting step 218.

According to some embodiments; the apparatus may have on-board means for showing a result, such as a colorimetric strip (not shown). Additionally or alternatively, the results are displayed in a display unit, separate and remote from apparatus 100.

Figure 3:
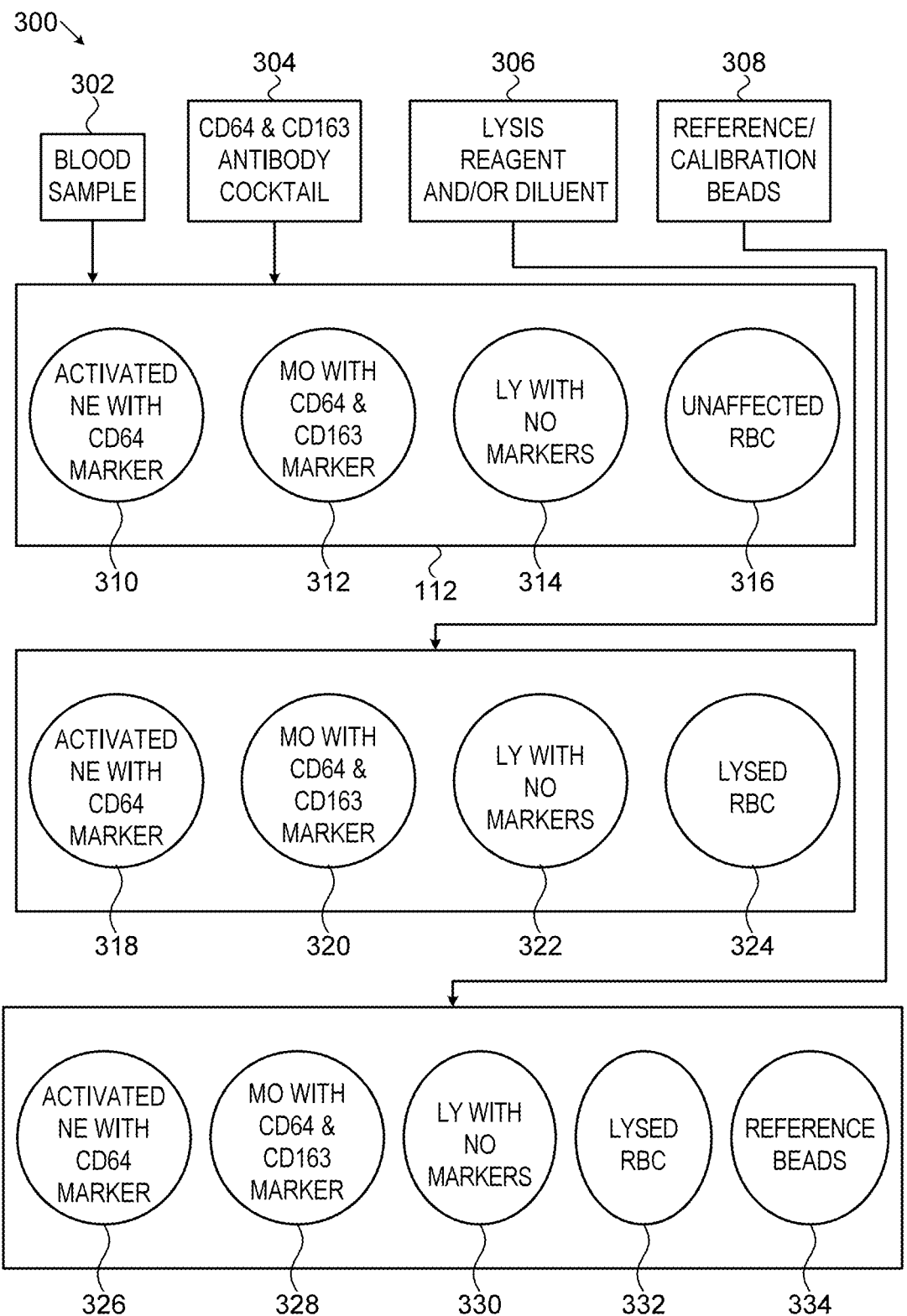

Reference is now made to FIG. 3, which is a simplified schematic illustration showing a methodology 300 for detecting a biological condition associated with a CD64 cell surface antigen, in accordance with an embodiment of the present invention.

According to some embodiments, the method is carried out in the apparatus shown in FIG. 1 and as described herein. A biological specimen, such as a blood sample, is aspirated via specimen receiving element 118 to sample composition chamber 104, and then to treatment chamber 112. The sample is typically of a volume in the range of 10-200 μL.

The blood sample is typically whole blood recently removed from a patient. The whole blood comprises mainly red blood cells (also called RBCs or erythrocytes), platelets and white blood cells (also called leukocytes), including lymphocytes and neutrophils. Increased number of neutrophils, especially activated neutrophils are normally found in the blood stream during the beginning (acute) phase of inflammation, particularly as a result of bacterial infection, environmental exposure and some cancers.

A cocktail 304 comprising antibodies to CD64 and antibodies to CD163 is introduced to the treatment chamber (see Davis et al. (2006)). Each antibody type is typically tagged by a specific fluorescent tag.

The contents of the chamber are incubated and/or mixed as is required to bind the activated blood neutrophils with the CD64 tagged antibody (also called a marker) to form activated neutrophils with CD64 marker 310, and/or monocyte with a CD64 tagged antibody and a CD163 tagged antibody 312. Lymphocytes with no markers 314 are present in the contents, as well as unaffected RBCs 316.

Thereafter, a lysis reagent or diluent 306 is introduced into treatment chamber 112. In the case of a lysis reagent, it is adapted to lyse red blood cells to form lysed red blood cells 324. Additionally, reference/calibration beads 308 are added to the treatment chamber. These are used to calibrate the outputs, as is explained with reference to FIGS. 5A-5D hereinbelow.

CD64 (Cluster of Differentiation 64) is a type of integral membrane glycoprotein known as an Fc receptor that binds monomeric IgG-type antibodies with high affinity. Neutrophil CD64 expression quantification provides improved diagnostic detection of infection/sepsis compared with the standard diagnostic tests used in current medical practice.

CD163 (Cluster of Differentiation 163) is a human protein encoded by the CD163 gene. It has also been shown to mark cells of monocyte/macrophage lineage.

Figure 4:
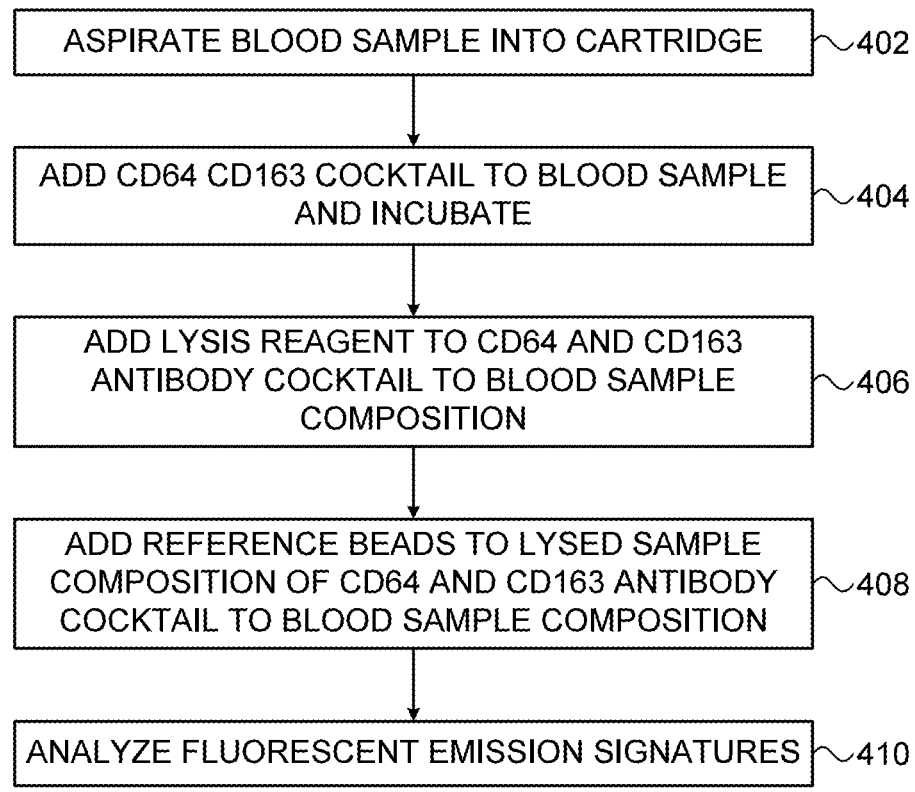

Reference is now made to FIG. 4, which is a simplified flow chart 400 of a method for detecting a biological condition associated with a CD64 cell surface antigen, in accordance with an embodiment of the present invention.

According to some embodiments, the method is carried out in the apparatus shown in FIG. 1 and as described herein. In a first transferring step 402, a biological specimen, such as a blood sample is aspirated via specimen receiving element 118 to sample composition chamber 104. The sample is typically of a volume in the range of 10-200 μL.

Typically, the total sample volumes are in the range of 10 to 1000 μL, 100 to 900 μL, 200 to 800 μL, 300 to 700 μL, 400 to 600 μL, or 420 to 500 μL.

According to some embodiments, the volume of the treatment composition chambers 106, 108, 110 (also called blisters) is from about 1 μL to 1000 μL. According to other embodiments, the volume of the specimen is from about 10 μL to 200 μL. According to other embodiments, the volume of the specimen is about 1, 10, 20, 30, 40, 50, 60, 70, 80, 90, 100, 120, 140, 160, 180, 200, 250, 300, 350, 400, 450, or 500 μL.

According to some embodiments, the volume of the treatment compositions 120, 122, 124 is at most about 500 μL. According to other embodiments, the volume of the specimen is at most about 200 μL. According to other embodiments, the volume of the specimen at most about 500, 450, 400, 350, 300, 250, 200, 180, 160, 140, 120, 100, 90, 80, 70, 60, 50, 40, 30, 20, 10, or 1 μL.

According to some embodiments, the volume of a reactant is at least about 1 μL. According to other embodiments, the volume of the specimen is from about 10 μL. According to other embodiments, the volume of the specimen is at least about 1, 10, 20, 30, 40, 50, 60, 70, 80, 90, 100, 120, 140, 160, 180, 200, 250, 300, 350, 400, 450, or 500 μL.

In an addition step 404, a cocktail of tagged antibodies to CD64 and to CD163 is added to the treatment chamber 112 and is incubated with the blood sample. In the incubation phase of this step, the antibodies bind activated neutrophils with CD64 marker 310, and/or monocytes activated with a CD64 tagged antibody and a CD163 tagged antibody 312.

In a lysis reagent addition step 406, the lysis reagent is added to the treatment chamber and thereby lyses at least some of the RBCs in the chamber.

At any suitable time, typically following lysis step 406, reference beads are added to the contents of the treatment chamber in a reference bead adding step 408.

After a predefined period of time, an analysis step 410 is performed to analyze the fluorescent emission signatures from the contents. This is described in further detail with reference to FIGS. 5A-5D. According to some examples, the evaluation chamber 114 is constructed and configured to allow cells to pass through a reading zone 130 such that each cell passing therethrough is analyzed individually. The assay sensitivity is around 86% and its specificity is around 87% (Hoffmann, 2011).

The time required to complete an assay using apparatus 100 of the present invention varies depending on a number of factors, with non-limiting examples that include described herein. In some embodiments, the time required to complete an assay is from about 0.5 to 100 minutes. In other embodiments, the time required to complete an assay is from about 1 to 20 minutes. In still other embodiments, the time required to complete an assay is from about 1 to 10 minutes. In some examples, the time required to complete an assay is from about 1, 2, 3, 4, 5, 6, 7, 8, 9, 10, 15, 20, 25, 30, 35, 40, 50, 60, 80, or 100 minutes.

Figure 5A:
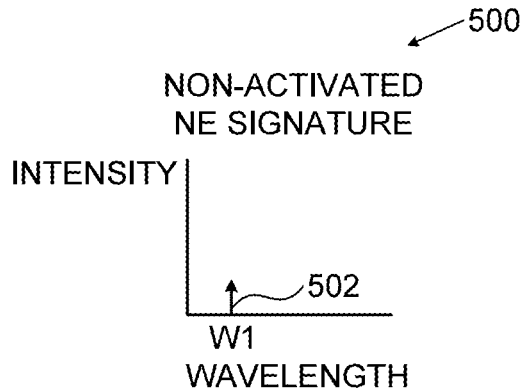

Reference is now made to FIG. 5A, which is a graphical output of a fluorescent detection assay of a non-activated neutrophil signature 500 associated with the method of FIGS. 3-4, in accordance with an embodiment of the present invention. The non-activated tagged neutrophils each emit a signal 502 at wavelength W1 of an intensity $I_1$. The wavelengths shown in FIGS. 5A-5D represent a peak wavelength of waveband outputs detected, as are shown in FIGS. 7-11.

Figure 5B:
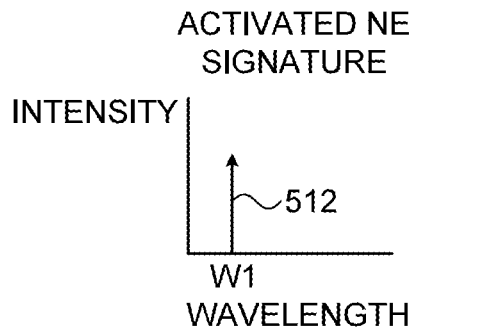

FIG. 5B shows a graphical output of a fluorescent detection assay of an activated neutrophil signature 510, associated with the method of FIGS. 3-4, in accordance with an embodiment of the present invention. Each activated tagged neutrophil emits an activated neutrophil signature 512 at wavelength W1 of an intensity $I_2$. Typically $I_2$ is greater than $I_1$. In some cases the difference in signatures 512 and 510 may be detected by an image analysis, a fluorescent emission radiation count or by other qualitative or quantitative methods known in the art. The current example is not meant to be limiting.

Figure 5C:
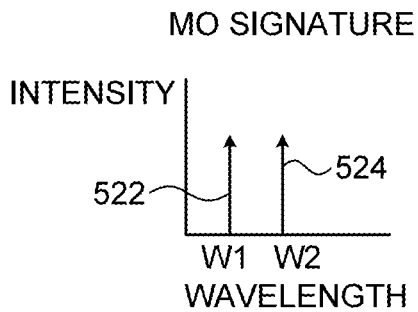

Turning to FIG. 5C, there can be seen a graphical output of a fluorescent detection assay of a monocyte signature 520, associated with the method of FIGS. 3-4, in accordance with an embodiment of the present invention. The monocyte signature comprises a first signal 522 at a first wavelength W1 of an intensity $I_3$ and a second signal 524 at a second wavelength W2 of an intensity $I_4$.

Figure 5D:
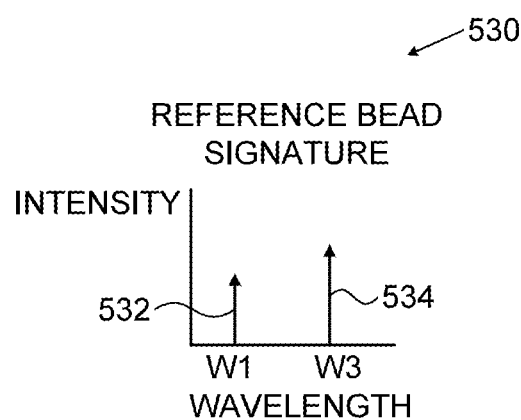

FIG. 5D shows a graphical output of a fluorescent detection assay of a reference bead signature 530, associated with the method of FIGS. 3-4, in accordance with an embodiment of the present invention. The reference bead signature comprises a first signal 532 at a first wavelength W1 of an intensity $I_1$ (similar or equal to non-activated tagged neutrophils' signal 502) and a second signal 534 at a second wavelength W3 of an intensity $I_5$.

This methodology enables the identification and quantification of activated neutrophils by intensity of signature 512 of the CD64 tag. Monocytes are identified by the double signal signature 522, 524, acting as a positive control. Reference beads are identified by the unique signal 534 at wavelength W3. The intensity of signal 532 at wavelength W1 provides a reference level of CD64 for the comparison of intensity of 512 of the neutrophils.

Lymphocytes with no markers 330 (FIG. 3) act as a negative control and should provide no fluor signature, but may be detected by their scattering or other characteristics. Further details of some embodiment of this assay procedure are described in U.S. Pat. No. 8,116,984 and in Davis, B H et al., (2006).

Figure 6:
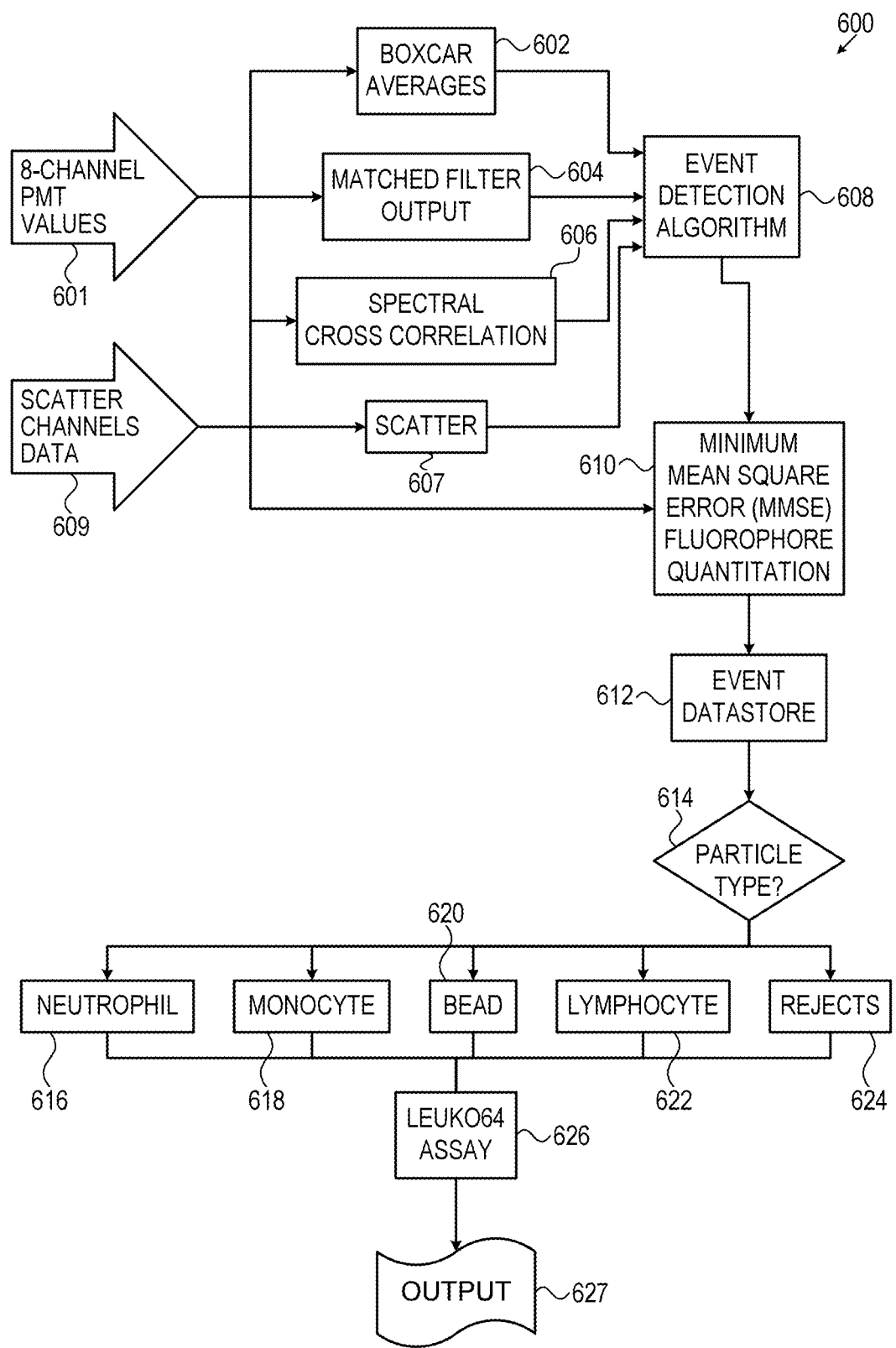

Reference is now made to FIG. 6, which is a simplified flow chart of a method 600 for differentiating between different particles, in accordance with an embodiment of the present invention.

The input to the processing is a time series from each of the channels in the eight channel photomultiplier array 601. In addition, data from multiple scatter channels 609 is introduced. Each fluorescent time series and scatter time series may be processed individually employing respective spectral cross-correlation algorithm 606 and scatter algorithm 607 to smooth it and minimize noise. Two possible processing methods are boxcar averaging algorithm 602 and matched filtering algorithm 604. In addition, groups of individual channels may be correlated to yield a multiple spectral cross-correlations 606. One or more of these derived time series may be used to determine event locations.

Once an event is located in the eight channel time series the composition of that event in terms of known fluorophore signatures is determined using a minimum mean square error fit 610. The event is now described in terms of its composition of known fluors. Each event thus described is stored in an event store, i.e. memory, together with the data from the eight time series for that event and its description 612. Based on the fluor composition for each event in the data store, it is possible to determine the type of particle. For example, a neutrophil 616 is characterized by the single fluor attached to the CD64 antibody shown in FIG. 5 as W1. Thus events that are preponderantly characterized by the single fluor attached to the CD64 antibody are identified as neutrophils.

Similarly, monocytes 618 are characterized by fluors W1 and W2 so that an event with both of these fluor signatures is identified as a monocyte. Similarly, a bead 620 is characterized by an event that has fluors W1 and W3. Lymphocytes 622 do not express significant fluorescence but are identified by their scatter as events. Events that do not match any of the known combinations of the fluorophores are identified as rejects 624.

Given the population of identified events, the median intensity of the neutrophil population and the median intensity of the bead population are determined. The ratio of the neutrophil median to the bead median is the desired Leuko64 index. The positive control value is determined as the median intensity of the CD64 fluorophore bound to monocytes divided by the median intensity of the same fluorophore on the bead population. The negative control value is determined by the median intensity of the CD64 fluorophore bound to lymphocytes. These are the key steps in performing the Leuko64 assay.

FIG. 7 is a graphical output 700 of fluorescence from reference beads in eight wavebands, in accordance with an embodiment of the present invention. This figure shows the smoothed signals from the eight channel PMT array for two reference beads. The amplitude for each waveband is shown on the same graph. The corresponding wavelength range is shown for each plot 702, 704, 708, 710, 712, 714, 716, 718 in the legend box. The two fluorophores signatures present in this plot are 702,704 and 708 for FITC, which is the fluorophore attached to the CD64 antibody and 710, 712 for Starfire Red, which is the fluorophore identifying the reference beads.

Reference is now made to FIG. 8, which is a graphical output 800 of data from FIG. 7 after a first mathematical manipulation, in accordance with an embodiment of the present invention. FIG. 8 shows the cross correlation of wave bands one two and three corresponding to wavelength 500 to 525, 525 to 550, and 552 to 575 nm. This cross correlation is computed by multiplying the boxcar smoothed time series corresponding to these wavelengths. This signal will have a high-value when an event containing the FITC fluorophore is present.

FIG. 9 is a graphical output 900 of data from FIG. 7 after a second mathematical manipulation, in accordance with an embodiment of the present invention. FIG. 9 shows the cross correlation of wave bands 3, 4 and 5 corresponding to wavelengths 550 to 575, 575 to 600, and 600 to 625 nm. This signal will have a high-value when an event containing the PE fluorophore is present.

FIG. 10 is a graphical output 1000 of data from FIG. 7 after a third mathematical manipulation, in accordance with an embodiment of the present invention. FIG. 10 shows the cross correlation of wave bands 7 and 8 corresponding to wavelengths 650 to 675, and 675 to 700 nm. This signal will have a high-value when an event containing the Starfire Red fluorophore is present.

FIG. 11 is a graphical output 1100 of an event locator, based on data from FIG. 8-10, in accordance with an embodiment of the present invention. FIG. 11 shows the event locations determined from the cross correlations computed in FIGS. 8, 9 and 10. The solid fill area 1102 corresponds to the region where any of the cross correlations 802, 902 and 1002 exceeded a predefined threshold. Similarly, the solid fill area 1104 corresponds to the region where any of the cross correlations 804, 904 and 1004 exceeded a predefined threshold. This then completes the event location process.

Reference is now made to FIG. 12, which is a scatterplot matrix 1200 of four fluor signatures 1210, 1220, 1230 and 1240, showing four distinct event groups, in accordance with an embodiment of the present invention.

Fluor signature 1210 is the group of reference beads that contain the reference level of the F488 fluorophore (F488 is the designation of a fluorophore with an emission spectrum identical to or equivalent to Fluorescein isothiocyanate (FITC)) and are identified by their Starfire Red™ (Starfire Red is the designation of a fluorophore or its emission spectrum, produced by Bangs Laboratory, 9025 Technology Dr. Fishers, Ind. 46038-2886, USA) embedded fluorophore. Fluor signature 1220 is the group of monocytes tagged with the phycoerythrin (PE) fluorophore identified by the signature name PE488 (exited by a laser at 488 nm). (PE488 is the designation of a fluorophore with an emission spectrum identical to or equivalent to phycoerythrin (PE)).

Fluor signature 1230 is the group of lymphocytes tagged with the PEAF488 (Alexa Fluor®610, Life Technologies Corporation, 3175 Staley Rd. Grand Island, N.Y. 14072 USA) fluorophore. Finally, fluor signature 1240 is the group of neutrophils tagged with the F488 (Alexa Fluor® 488 Life Technologies Corporation, 3175 Staley Rd. Grand Island, N.Y. 14072 USA) fluorophore, which is the primary target group for analysis.

Reference is now made to FIG. 13A, which is a flowchart 1300 of a specific implementation of an algorithm for selecting groups of data from a scatterplot, in accordance with an embodiment of the present invention.

The algorithm in FIG. 13A is a specific implementation of the general algorithm in FIG. 13B to select each of the groups 1210, 1220, 1230 and 1240 (FIG. 12) and determine specific parameter values in each of the groups.

In a first ordering signature step 1304 the Star Fire Red (SFR) signature is used to order (from smallest SFR signature to largest) the entire dataset of waveband and signature values 1302.

In a second step 1320, an analysis of a histogram of an SFR signature values as shown in FIG. 14A to select the group 1210. This is a small group 1404 at the upper end of group 1402 in the histogram 1400 in FIG. 14A. The next step is to remove this group from the overall dataset as shown in FIG. 13 Step 1322. The removed group is the bead dataset 1324.

A dataset of Waveband and Signature values with bead dataset removed 1340 is then manipulated as follows. In an ordering step 1342, the data is organized according to its PE (phycoerythrin) signature from smallest to largest PE (phycoerythrin) signature.

In an analyzing PE histogram set step, 1344, the data is manipulated to find a group corresponding to monocytes.

In an extracting monocytes dataset step 1346, a monocyte dataset of waveband and signature values 1348 is extracted. A dataset of waveband and signature values with beads and monocytes removed 1360 is then further processed as follows. Set 1360 is organized according to its PEAF (PEAF488) (see above for beads and PE) signature in an order according to PEAF signature ordering step 1362.

In an analyzing PEAF histogram to find a group corresponding to lymphocytes step 1364, set 1360 is analyzed to determine if any of the data have behavior corresponding to lymphocytes.

In an extraction step 1366, a lymphocyte dataset of waveband and signature values 1368 is extracted from set 1360 and the remaining dataset is a dataset of waveband and signature values with bead, monocytes and lymphocytes removed 1380.

In an order by Diodel signature step 1382, dataset 1380 is analyzed according to a Diodel signature (see above). Dataset 1380 is then analyzed in an analyzing step 1384 to find a group of data having properties of neutrophils.

In an extracting step 1386, a group of data having properties of non-neutrophils 1388 is removed. A remaining group 1391 (assumed to be neutrophils) is used in a computing step 1392 to compute desired metric from the group parameters.

Reference is now made to FIG. 13B, which is a flowchart of a general implementation of an algorithm 1350 for selecting groups of data from a scatterplot, in accordance with an embodiment of the present invention.

In a first ordering signature step 1305 a first signature is used to order the dataset of waveband and signature values 1303.

In a second step 1321, an analysis of a histogram of a 1st signature values to find the group corresponding to $1^{st}$ signature 1325, as exemplified in FIG. 14A to select the group 1210. This is a small group 1404 at the upper end of group 1402 in the histogram 1400 in FIG. 14A. It should be noted that this is but one way to select the group and other methods employing additional data set values in combination may be used. The next step is to remove this group from the overall dataset as shown in FIG. 13B Step 1323. A removed group is a 1st signature dataset 1325.

A dataset of Waveband and Signature values with 1st dataset removed 1341 is then manipulated as follows. In an ordering step 1343, the data is organized according to its 2nd signature.

In an analyzing $2^{nd}$ signature histogram set step, 1345, the data is manipulated to find a group corresponding to the $2^{nd}$ signature.

In an extracting $2^{nd}$ signature dataset step 1347, a $2^{nd}$ signature dataset of waveband and signature values 1349 is extracted. A dataset of waveband and signature values with $1^{st}$ and $2^{nd}$ signatures groups removed 1361 is then further processed as follows. Set 1361 is organized according to its $i^{th}$ signature in an order according to $i^{th}$ signature ordering step 1363.

In an analyzing $i^{th}$ histogram to find a group corresponding to $i^{th}$ signature step 1365, set 1361 is analyzed to determine if any of the data have behavior corresponding to the $i^{th}$ signature.

In an $i^{th}$ signature extraction step 1367, an $i^{th}$ signature dataset of waveband and signature values 1369 is extracted from set 1381 and the remaining dataset is a dataset of waveband and signature values with $1^{st}$ $2^{nd}$ and $i^{th}$ signature groups removed 1381.

In an order by $N^{th}$ signature step 1383, dataset 1381 is analyzed according to an $N^{th}$ signature. Dataset 1381 is then analyzed in an analyzing step 1385 to find a group of data having properties of not having Nth signature properties.

In an extracting step 1387, a group of data having properties of non-Nth signatures 1397 is removed. A remaining group 1395 (assumed to be Nth groups) is used in a computing step 1393 to compute desired metric from the group parameters.

FIG. 14A is a histogram 1400 of data of Starfire Red (SFR) signature values, in accordance with an embodiment of the present invention.

FIG. 14B shows a plot 1450 of a polynomial 1452 and first derivative thereof 1456 and second derivative thereof 1458 of histogram 1400 shown in FIG. 14A, in accordance with an embodiment of the present invention.

Referring to FIG. 14B, the method of determining an upper group 1404 in FIG. 14A is as follows. A polynomial 1452 of sufficient degree is fitted to the histogram data 1454 (as shown in FIG. 13A, set 1324) is shown in FIG. 14B. The first derivative 1456 and the second derivative 1458 of this polynomial are computed. A plurality of zeros 1460 of the first derivative are indicated by the square boxes along the zero line. A point where the polynomial is both maximum and has a zero derivative 1462 is indicated by the box with an X in it. This point in the histogram corresponds to the peak of the large group 1402 (FIG. 1402). A next zero 1464 of the derivative of the polynomial corresponds to the end of the large group in the histogram. All points in the histogram above this value are in the small group. Since the dataset has been ordered from smallest to largest based on the value of SFR488, and the histogram horizontal axis is also ordered from smallest to largest value of SFR488 the point at which the large group ends is the value of SFR488 above which records in the SFR488 ordered dataset are to be removed and identified as the bead dataset 1324 of waveband and signature values as indicated in FIG. 13A.

FIG. 15A is a histogram 1500 of data of PE488 signature values, in accordance with an embodiment of the present invention.

FIG. 15B shows a polynomial fitted to the histogram in FIG. 15A as well as a corresponding first derivative 1556 and a second derivative 1558, in accordance with an embodiment of the present invention.

The records remaining in the dataset are now reordered using the PE488 signature from smallest to largest. Histogram 1500 of the PE488 signature values 1502 is shown in FIG. 15A. Again in this case, there is a small group 1504 to the right of the large group 1502 which corresponds to the desired monocyte population. FIG. 15B shows the polynomial 1552 fitted to data 1554 of histogram 1500 in FIG. 15A as well as the corresponding first and second derivatives. The upper group 1504 is determined in the same way as the upper group of the SFR488 histogram as was described previously. It should be noted that while in both of these cases only a one dimensional histogram was analyzed and used as the basis for selecting the desired population, multiple fields from each record in the dataset may be used to effect a group selection. As noted in FIG. 15, the monocyte group 1504 is removed from the dataset which now contains primarily lymphocytes, neutrophils and other particles such as un-lysed erythrocytes and other debris.

FIG. 16A is a histogram 1600 of data 1602 of PEAF488 signature values, in accordance with an embodiment of the present invention.

FIG. 16B shows a polynomial 1652 fitted to histogram data 1654 from FIG. 16A as well as a corresponding first derivative 1656 and a second derivative 1658, in accordance with an embodiment of the present invention.

The records remaining in the dataset are now reordered using a PEAF488 signature corresponding to lymphocytes. A histogram 1600 of the PEAF488 signature is shown in FIG. 16A and the corresponding polynomial fit with its first and second derivatives are shown in FIG. 16B. The process outlined above is applied in this case as well to identify and remove a small group 1604 appearing at an upper end of the histogram, from a large group 1602. The lymphocyte group is now removed as shown in FIG. 13A leaving a dataset 1380 which now contains primarily neutrophils and other particles such as unlysed erythrocytes and other debris.

While neutrophils 1391 are tagged with a fluorophore with an F488 signature, other particles appear to express this signature because of the unbound fluorophore in solution. The other particles, however, are smaller than neutrophils, which now comprise the group with the largest forward scatter as measured by a Diode1 (forward scatter detector) channel. A histogram of the Diode1 channel is shown in FIG. 17A.

FIG. 17A is a histogram 1700 of data of Diode 1 channel signature values, in accordance with an embodiment of the present invention.

FIG. 17B shows a polynomial 1752 fitted to data 1754 from the histogram in FIG. 17A, as well as a corresponding first derivative 1756 and a second derivative 1758, in accordance with an embodiment of the present invention.

As described above, an upper group 1704 (FIG. 17A) corresponding to larger particles, which are the neutrophils is selected. This completes the decomposition of the original dataset 1302 into the four distinct event groups (1324, 1348, 1368, 1391) shown in FIG. 13A.

Within each group various parameters may be computed from the fields in the dataset. An example is shown in the following table.

| Observations | NAM | MEDUG | MEDF488 | MEDWaveband2 | MEDWaveband2N | INDEX488 | INDEXWaveband2 | INDEXWaveband2N |
|---|---|---|---|---|---|---|---|---|
| SFR488 | 166 | 978.72 | 3395.26 | 3062.00 | 503.80 | 1.00 | 1.00 | 1.00 |
| PE488 | 73 | 3851.88 | 5968.83 | 5843.50 | 723.66 | 1.76 | 1.91 | 1.44 |
| PEAF488 | 332 | 1164.38 | −4.36 | 37.00 | 4.63 | 0.00 | 0.01 | 0.01 |
| F488 | 620 | 379.98 | 379.98 | 361.00 | 37.92 | 0.11 | 0.12 | 0.08 |
| Diode1 | 59 | 7027.00 | −113.54 | −73.00 | −6.81 | −0.03 | −0.02 | −0.01 |

The observations column contains the name of the group. The NAM column is the number of events in the group. The MEDUG column is the median value of the signature for that group. For example in the SFR488 row the median SFR488 signature value is 978.72. The MEDF488 column contains the median value of the F488 signature for the specified group. The MEDWaveband2 column contains the median value of the Waveband2 values in the group. The MEDWaveband2N column contains the median value of the Waveband2N values in the group. The INDEX488 column contains the ratio of the MEDF488 value for the group to that of the SFR488 group. Similarly, INDEXWaveband2 and INDEXWaveband2N are the ratios of the Waveband2 and Waveband2N medians for the group to that of the SFR488 group.

Although, specific groups corresponding to leukocyte subsets and a specific algorithm to compute a specific index based on these groups has been illustrated, one skilled in the art can use this basic approach whenever it is necessary to select groups from a dataset and compute numeric values based on parameters associated with these groups as shown in the general diagram of figure X.

FIG. 18A-18N is a sequential set of schematic drawings of the operation of an apparatus 100 (FIG. 1) for detecting a biological condition, in accordance with an embodiment of the present invention.

In FIG. 18A, a blood sample 1801 enters a specimen receiving element 1818 and fills a chamber 1804. In FIG. 18B, a blister 1820 comprising a treatment composition 120 (FIG. 1) is pressed and antibody cocktail is mixed with 10 microliters of the blood sample.

In FIG. 18C, a mixing bellows 1815 is pressed and this effects mixing of the antibody cocktail and the 10 microliters of the blood sample in a first mixing chamber 1812 to form a first mixture 1803.

In FIG. 18D, the bellows is released and mixture 1803 is siphoned along a tortuous channel 1813 and into a second mixing chamber 1811. Upon release of the bellows, the first mixture returns from the second mixing chamber, back along the tortuous channel to the first mixing chamber. Every time the bellows is pressed the mixture moves towards the second chamber and every time it is released, it returns, wholly or in part to the first chamber. This mixing may be performed multiple times.

In FIGS. 18E-18G, a second composition blister 1822 is pressed, releasing a second composition 122 (FIG. 1), such as a lysis composition thereby forming a second mixture 1085. The second mixture is mixed by pressing of bellows 1815, the second mixture returns from the second mixing chamber, back along tortuous channel 1813 to the first mixing chamber. Every time the bellows is pressed the mixture moves towards the second chamber 1811 and every time it is released, it returns, wholly or in part to the first chamber 1812. This mixing may be performed multiple times.

In FIGS. 18H-18J, a third blister 1824 is released comprising a third composition 124 (FIG. 1), such as a control reference, into the second mixing chamber, thereby forming a third composition 1807. The third mixture is mixed by pressing of bellows 1815, the third mixture returns from the second mixing chamber, back along tortuous channel 1813 to the first mixing chamber. Every time the bellows is pressed the mixture moves towards the second chamber 1811 and every time it is released, it returns, wholly or in part to the first chamber 1812. This mixing may be performed multiple times.

In FIGS. 18J-18L, a reading bellows 1817 is pressed, which forces some of the third composition towards a reading cuvette 1830.

In FIGS. 18M-18N, particles 1860 from the third composition flow from the cuvette 1830 along a channel 1852 to a reading region 1850. The cells pass through the reading region and are excited by one or more lasers 1862, 1863. At least one excitation laser beam 1864 impinges on cell 1860 and an emission beam 1866 is detected by a detector 1870. In one example, this is cell emission fluorescence and detector 1870 is a spectrometer.

Reference is now made to FIG. 19, which is a simplified three dimensional front view of a system 1900 comprising a reader assembly 1901 and a cartridge 1911 for detecting a biological condition, in accordance with an embodiment of the present invention.

Shown in FIG. 19 are outer view of the reader assembly 1901 and an inner view 1902 and cartridge 1911. The cartridge is inserted in the reader assembly as shown. Once the cartridge is inserted in the reader assembly all assay pre-analytical processing and analysis are performed automatically. Results of the analysis are displayed on a user interface touch-screen 1915, which is also used to control operation of the reader.

The internal components of the reader assembly are seen in view 1902, FIG. 19. Reader assembly 1901 comprises an ITX computer, 1922, a Galil motor controller, 1924, an electronics power supply 1926, cartridge, 1911, inserted into a cartridge handling unit (CHU) 1928 and a forward scatter detector 1930. Not seen are the reader optics 1942, a data acquisition board 1944 and a general electronics printed circuit board 1946.

Example

Application No. 1—CD64 Infection & Sepsis

A cartridge 102 (FIG. 1) is prepared for receiving a blood sample. The cartridge comprises a number of treatment composition chambers 106, 108, 110, adapted to respectively house a corresponding number of treatment compositions 120, 122, 124. These compositions are described in further detail in U.S. Pat. No. 8,116,984 and in Davis, B H et al., (2006)), incorporated herein by reference. In brief, Reagent A comprises a mixture of murine monoclonal antibodies (contains buffered saline), Reagent B—10× Concentrated Trillium Lyse solution (contains ammonium chloride), Reagent C—suspension of 5.2 μm polystyrene beads labeled with Starfire Red and fluorescein isothiocyanate (FITC), (contains <0.1% sodium azide and 0.01% Tween 20).

In a sample transferring step 202 (FIG. 2), a 10 uL blood sample, is transferred from outside apparatus 100 via receiving element 118 into sample composition chamber 104 and then on to treatment chamber 112 in a transferring step 214.

An antibody composition (Reagent A) 120 comprising CD64 antibodies is transferred via transfer element 107 to the treatment chamber 112 in a composition transfer step 204.

These two steps combined with mixing step 206 take around four minutes using cartridge 102 of the present invention.

A lysis buffer (Reagent B) 122 is also added and mixed with the resultant mixed composition. This step and mixing all the compositions takes around three minutes using cartridge 102 of the present invention. Reference beads (Reagent C) 308 are added to the treatment chamber.

The evaluation chamber 114 is configured and constructed for one or more evaluation steps 216.

According to some embodiments, the cartridge is introduced into a system as described in International patent application publication no. WO2011/128893 to Kasdan et al., incorporated herein by reference. This system has software associated therewith for computing the CD64 and CD163 indices on leukocytes.

The results of the evaluation step are then outputted in a results outputting step 218. According to this example, the time taken from the introduction of the small blood sample to obtaining an indication of sepsis is less than 15 minutes, typically around 10 minutes.

From a user point of view, the following steps are performed:

1) The user adds drop of blood to the cartridge 102 and seals it. (10 µL are metered out by microfluidics).
2) Blister A (106) is pressed, releasing 100 µL of Reagent A. Mixing in the cartridge is controlled by the cartridge handling unit (CHU), followed by a 4-minutes incubation.
3) Blister B (108) is pressed, releasing ~250 µL of Reagent B. Mixing in the cartridge is controlled by the CHU, followed by a 3-5-minutes incubation.
4) Magnetic stirbar is activated, stirring the bead suspension (Reagent C).
5) Blister C (110) is pressed, releasing 100 µL of Reagent C. Mixing in the cartridge is controlled by the CHU. According to one example, Reagent A is a mixture of murine monoclonal antibodies-diluted 1:5 in buffered saline (PBS+0.5% BSA); Reagent B is a Trillium Lyse solution (at working concentration); Reagent C is a suspension of 5.2 µm polystyrene beads labeled with Starfire Red and FITC, diluted 1:100 in PBS+0.01% Tween 20.
6) The sample is read by the optoelectronics core, and collected to the reading below.
7) Data is analyzed automatically and result is presented.
8) The cartridge is disposed as biohazard.

TABLE 2

Comparison of Prior art methodology with the methodology of the present invention for detecting sepsis using CD64 and CD163 antibodies.
LeukoDx device-present invention

| Step | Description | Volume (uL) | Duration (min) | comments |
|---|---|---|---|---|
| 1 | Mixing blood and antibodies | Blood-10 Abs-50 | | |
| 2 | Adding RBC lysis buffer | 250 | 3 | Might require heating the buffer to 37 C. |
| 3 | Incubating, Vortexing | | 3 | |
| 4 | Adding normalization beads | 2 | Less than 1 | |
| 5 | Reading | | Less than 1 | |
| | Total | 312 | 10 | |

In the case of sepsis, by "normalization" is meant taking the ratio of the median of the target population fluorescence emission to the median of the reference bead population fluorescence emission.

According to some embodiments, the readout may comprise an optoelectronics core, which enables identification and detection of fluorescent signals. The CCD in the core, used for focusing, can also be used to read chemiluminescent signals. The readout to user may also indicate where the result falls relative to reference ranges.

The contents of these publications are incorporated by reference herein where appropriate for teachings of additional or alternative details, features and/or technical background. It is to be understood that the invention is not limited in its application to the details set forth in the description contained herein or illustrated in the drawings. The invention is capable of other embodiments and of being practiced and carried out in various ways. Those skilled in the art will readily appreciate that various modifications and changes can be applied to the embodiments of the invention as hereinbefore described without departing from its scope, defined in and by the appended claims.

REFERENCES

Assicot, Marcel, et al. "High serum procalcitonin concentrations in patients with sepsis and infection." *The Lancet* 341.8844 (1993): 515-518.
Aulesa, C., et al. "Validation of the Coulter LH 750 in a hospital reference laboratory." *Laboratory Hematology* 9.1 (2003): 15-28.Hawkins, Robert C. "Laboratory turnaround time." The Clinical Biochemist Reviews 28.4 (2007): 179.
Ault, Kenneth A. "Flow cytometric measurement of platelet function and reticulated platelets." *Annals of the New York Academy of Sciences* 677.1 (1993): 293-308.
Blajchman, Morris A., et al. "Bacterial detection of platelets: current problems and possible resolutions." *Transfusion medicine reviews* 19.4 (2005): 259-272.
Bodensteiner, David C. "A flow cytometric technique to accurately measure post-filtration white blood cell counts." *Transfusion* 29.7 (1989): 651-653.
Cheson, Bruce D., et al. "National Cancer Institute-sponsored Working Group guidelines for chronic lymphocytic leukemia: revised guidelines for diagnosis and treatment." *Blood* 87.12 (1996): 4990-4997.
Christ-Crain, Mirjam, et al. "Effect of procalcitonin-guided treatment on antibiotic use and outcome in lower respiratory tract infections: cluster-randomised, single-blinded intervention trial." *Lancet* 363.9409 (2004): 600-607.
Cristofanilli, Massimo, et al. "Circulating tumor cells, disease progression, and survival in metastatic breast cancer." *New England Journal of Medicine* 351.8 (2004): 781-791.
Davis, Bruce H., et al. "Neutrophil CD64 is an improved indicator of infection or sepsis in emergency department patients." Archives of pathology & laboratory medicine 130.5 (2006): 654-661.
Dieye, Tandakha Ndiaye, et al. "Absolute CD4 T-cell counting in resource-poor settings: direct volumetric measurements versus bead-based clinical flow cytometry instruments." *JAIDS Journal of Acquired Immune Deficiency Syndromes* 39.1 (2005): 32-37.
Divers, S. G., et al. "Quantitation of CD62, soluble CD62, and lysosome-associated membrane proteins 1 and 2 for evaluation of the quality of stored platelet concentrates." *Transfusion* 35.4 (2003): 292-297.
Drexler, Hans G., et al. "Diagnostic value of immunological leukemia phenotyping." *Acta haematologica* 76.1 (1986): 1-8.
Dziegiel, Morten Hanefeld, Leif Kofoed Nielsen, and Adela Berkowicz. "Detecting fetomaternal hemorrhage by flow cytometry." *Current opinion in hematology* 13.6 (2006): 490.
Fischer, Johannes C., et al. "Reducing costs in flow cytometric counting of residual white blood cells in blood products: utilization of a single platform bead free flow rate calibration method." Transfusion 51.7 (2011): 1431-1438.
Graff, Jochen, et al. "Close relationship between the platelet activation marker CD62 and the granular release of platelet-derived growth factor." *Journal of Pharmacology and Experimental Therapeutics* 300.3 (2002): 952-957.
Guerti, K., et al. "Performance evaluation of the PENTRA 60C+ automated hematology analyzer and comparison with the ADVIA 2120." *International journal of laboratory hematology* 31.2 (2009): 132-141.

Hershman, M. J., et al. "Monocyte HLA-DR antigen expression characterizes clinical outcome in the trauma patient." *British Journal of Surgery* 77.2 (2005): 204-207.

Hilfrich, Ralf, and Jalil Hariri. "Prognostic relevance of human papillomavirus L1 capsid protein detection within mild and moderate dysplastic lesions of the cervix uteri in combination with p16 biomarker." *Analytical and Quantitative Cytology and Histology* 30.2 (2008): 78-82.

Hillier, Sharon L., et al. "A case-control study of chorioamnionic infection and histologic chorioamnionitis in prematurity." New England Journal of Medicine 319.15 (1988): 972-978.

Hoffmann, Johannes JML. "Neutrophil CD64 as a sepsis biomarker." Biochemia Medica 21.3 (2011): 282-290.

Kibe, Savitri, Kate Adams, and Gavin Barlow. "Diagnostic and prognostic biomarkers of sepsis in critical care." Journal of Antimicrobial Chemotherapy 66.suppl 2 (2011): ii33-ii40.

LaRosa, Steven P., and Steven M. Opal. "Biomarkers: the future." Critical care clinics 27.2 (2011): 407.

Liu, N. I. N. G., A. H. Wu, and Shan S. Wong. "Improved quantitative Apt test for detecting fetal hemoglobin in bloody stools of newborns." Clinical chemistry 39.11 (1993): 2326-2329.

Lotan, Yair, et al. "Bladder cancer screening in a high risk asymptomatic population using a point of care urine based protein tumor marker." The Journal of urology 182.1 (2009): 52-58.

Masse, M., et al. "Validation of a simple method to count very low white cell concentrations in filtered red cells or platelets." *Transfusion* 32.6 (2003): 565-571.

Matic, Goran B., et al. "Whole blood analysis of reticulated platelets: improvements of detection and assay stability." *Cytometry* 34.5 (1998): 229-234.

McDonald, C. P., et al. "Use of a solid-phase fluorescent cytometric technique for the detection of bacteria in platelet concentrates." *Transfusion Medicine* 15.3 (2005): 175-183.

Michelson, Alan D. "Flow cytometry: a clinical test of platelet function." *Open Access Articles* (1996): 290.

Miller, E. M.; Freire, S. L. S.; Wheeler, A. R. "Proteomics in Microfluidic Devices" In *Encyclopedia of Micro-and Nanofluidics*; Li, D. Q., Ed.; Springer: Heidelberg, Germany, 2008; Vol. 3, pp 1749-1758."

Moro, Ricardo, et al. "A new broad-spectrum cancer marker." *Vitro Diagnostic Technology* (2005).

Perry, Sara E., et al. "Is low monocyte HLA-DR expression helpful to predict outcome in severe sepsis?." *Intensive care medicine* 29.8 (2003): 1245-1252.

Ramakumar, Sanjay, et al. "Comparison of screening methods in the detection of bladder cancer." *The Journal of urology* 161.2 (1999): 388-394.

Rawstron, Andy C., et al. "Quantitation of minimal disease levels in chronic lymphocytic leukemia using a sensitive flow cytometric assay improves the prediction of outcome and can be used to optimize therapy." *Blood* 98.1 (2001): 29-35.

Rodriguez, William R., et al. "A microchip CD4 counting method for HIV monitoring in resource-poor settings." *PLoS medicine* 2.7 (2005): e182.

Rylatt, D. B., et al. "An immunoassay for human D dimer using monoclonal antibodies." *Thrombosis research* 31.6 (1983): 767-778.

Sacks, David B., et al. "Guidelines and recommendations for laboratory analysis in the diagnosis and management of diabetes mellitus." Clinical Chemistry 48.3 (2002): 436-472.

Segal, H. C., et al. "Accuracy of platelet counting haematology analysers in severe thrombocytopenia and potential impact on platelet transfusion." *British Journal of Haematology* 128.4 (2005): 520-525.

Stein, Paul D., et al. "D-dimer for the exclusion of acute venous thrombosis and pulmonary embolism: a systematic review." *Annals of internal medicine* 140.8 (2004): 589.

Sutherland, D. Robert, et al. "The ISHAGE guidelines for CD34+ cell determination by flow cytometry." *Journal of hematotherapy* 5.3 (1996): 213-226.

Wang, Chao, et al. "Reticulated platelets predict platelet count recovery following chemotherapy." *Transfusion* 42.3 (2002): 368-374.

What is claimed is:

1. A flow cytometry system for determining a biological condition in a mammalian subject, the system comprising:
   a) a valveless stationary cartridge for performing an assay, the cartridge comprising:
      i. a sealable sample chamber;
      ii. a first blister comprising a first reagent;
      iii. optionally a second blister comprising a second reagent;
      iv. optionally a third blister comprising a third reagent;
      v. a first mixing chamber;
      vi. a second mixing chamber;
      vii. a first bellows;
   wherein
      i. the sample chamber, first blister and optionally the second blister are each connected to the first mixing chamber;
      ii. the first bellows is connected to the second mixing chamber;
      iii. the first mixing chamber is connected to the second mixing chamber;
   and wherein:
      said cartridge is valveless;
      said cartridge is a closed system after receiving said specimen and sealing said sample chamber;
   the system further comprising:
      a) a cartridge handling unit for insertion of said cartridge;
      b) a mechanical controller;
      c) a laser
      d) a forward scatter detector;
      e) a fluorescence detector;
      f) a processor;
      g) a user interface touch-screen;
   wherein:
      the cartridge is being adapted to receive a fluid specimen from said subject into said sample chamber, to seal said sample chamber such that said cartridge is a closed system after sealing, pass a predetermined quantity of said specimen into said first mixing chamber; transfer at least one reagent from said first blister into said first mixing chamber, operate said first bellows to transfer liquid back and forth between said first and said second mixing chambers, to form a reaction product; and
   wherein:
      the cartridge handling unit is adapted to receive said cartridge;

the mechanical controller is adapted to release said reagent(s) from said blister(s) and to operate said bellows;

the laser is adapted to excite said reaction product;

the forward scatter detector is adapted to detect forward scatter from said reaction product;

the fluorescence detector comprising a multichannel photomultiplier (PMT) array, and is adapted to detect fluorescent signals associated with said reaction product;

the processor is adapted to receive data from said fluorescence detector and from said forward scatter detector and to process said data;

the user interface touch-screen is adapted to control operation of said laser and said detectors and to automatically receive and display an assay result from said processor to determine said biological condition in said subject.

2. A system according to claim 1, wherein said system further comprises a memory for storing an output of a fluor composition detection for each event, using a minimum mean square error (MMSE) fluorophore quantitation.

3. A system according to claim 1, wherein the cartridge limits processing of the fluid specimen to a fixed volume that is a fraction of an input volume of said fluid specimen.

4. A system according to claim 1, wherein said reagent(s) comprises a plurality of on-board reagents and wherein said cartridge is adapted to contact plurality of on-board reagents with at least one of said specimen and said reaction product.

5. A system according to claim 4, wherein said cartridge is adapted to induce cascaded sequential reactions of said on-board reagents with at least one of said specimen and said reaction product.

6. A system according to claim 1, wherein said first mixing chamber is of a volume of 200 to 10000 microliters.

7. A system according to claim 1, further comprising a temperature control device external to said cartridge, said device being adapted to control a temperature of a reaction in said mixing chamber(s).

8. A system according to claim 1, wherein said cartridge has a shelf-life of 6 to 24 months.

9. A system according to claim 1, wherein said bellows comprises an inflatable deformable elastic chamber adapted to apply at least one of a negative pressure and a positive pressure to said mixing chamber(s).

10. A system according to claim 1, wherein said specimen comprise cells.

11. A system according to claim 1, wherein said cartridge comprises at least one of the following elements;
i. a reservoir;
ii. a pump;
iii. a conduit;
iv. a miniaturized flow cell;
v. a transport channel;
vi. a reading channel;
vii. a microfluidic element;
viii. a compressed gas holding element
ix. a compressed gas releasing element;
x. a nozzle element;
xi. a mixing element; and
xii. a bellows element.

12. A system according to claim 1, wherein said reagent(s) comprises at least one of:
i) at least one target antibody;
ii) at least one positive control identifying antibody; and
iii) at least one negative control identifying detection moiety.

13. A system according to claim 1, wherein said plurality of on-board reagents comprises at least one reference composition comprising at least one of:
i) a target signal reference composition; and
ii) a reference identifier composition.

14. A system according to claim 1, wherein said plurality of on-board reagents disposed in said cartridge comprises at least one of:
i) a positive control moiety; and
ii) a negative control moiety.

15. A system according to claim 1, wherein said plurality of on-board reagents disposed in said cartridge comprise at least one sepsis biomarker.

16. A system according to claim 15, wherein said at least one biomarker comprises at least one of CD64 and CD163.

17. A system according to claim 11, wherein said reading channel is configured to pass said cells in said reaction product one by one through a reading region.

18. A method for determining a biological condition in a subject, the method comprising:
i) incubating a specimen from said subject in the system of claim 1 for a predetermined period of time; and
ii) receiving an indication responsive to said at least one reporter element thereby providing the indication of the biological condition in said subject.

19. A system according to claim 1, wherein said reagent(s) comprises at least one of a diluent and a lysis reagent.

20. A system according to claim 1, wherein said multi-channel photomultiplier array comprises eight channels.

21. A method according to claim 18, wherein the biological condition is selected from blood diseases such as leukemia, thrombocytopenia, immune system disorders, local infections, urinary tract disorders, autoimmune diseases and sepsis.

22. A method according to claim 18, wherein said indication is quantitative.

23. A method according to claim 18, wherein the method is completed within twenty minutes.

24. A method according to claim 18, wherein said method is a flow cytometric method.

25. A method for determining a biological condition in a mammalian subject, the method comprising:
i) incubating a specimen from the subject with at least one composition in a system according to claim 1, for a predetermined period of time to form at least one reaction product, when said subject has said biological condition; and
ii) receiving an indication of said at least one reaction product responsive to at least one reporter element in said system thereby providing the indication of the biological condition in said subject.

26. An automated method of determining the presence or absence of sepsis in a subject, comprising:
i) contacting a blood sample from the subject with a fluorescently-labeled binding moiety specific to a sepsis marker in the system of claim 1, wherein the volume of the blood sample is 50 µL or smaller;
ii) detecting the presence, absence or level of the binding moiety in the sample, thereby determining the presence or absence of sepsis in the subject within twenty minutes.

27. The method of claim 26, wherein the sepsis marker is CD64.

28. The method of claim 26, wherein the sepsis marker is CD163.

29. The method of claim 26, further comprising contacting the blood sample with a second fluorescently-labeled binding moiety specific for a second sepsis marker.

30. The method of claim 29, wherein the sepsis marker is CD64 and the second sepsis marker is CD163.

* * * * *